US009260759B2

(12) United States Patent
Teixeira et al.

(10) Patent No.: US 9,260,759 B2
(45) Date of Patent: Feb. 16, 2016

(54) PYRAZOLOANTHRONE AND DERIVATIVES THEREOF FOR THE TREATMENT OF CANCERS EXPRESSING MISRII

(75) Inventors: Jose Teixeira, Boston, MA (US); Patricia K. Donahoe, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 203 days.

(21) Appl. No.: 13/328,387

(22) Filed: Dec. 16, 2011

(65) Prior Publication Data

US 2012/0141605 A1 Jun. 7, 2012

Related U.S. Application Data

(63) Continuation of application No. 12/532,533, filed as application No. PCT/US2008/057837 on Mar. 21, 2008, now abandoned.

(60) Provisional application No. 60/919,429, filed on Mar. 22, 2007.

(51) Int. Cl.
*A61K 38/00* (2006.01)
*A61K 31/415* (2006.01)
*A01N 59/00* (2006.01)
*C12Q 1/68* (2006.01)

(52) U.S. Cl.
CPC .................................. *C12Q 1/6886* (2013.01)

(58) Field of Classification Search
None
See application file for complete search history.

(56) References Cited

U.S. PATENT DOCUMENTS

| | | | |
|---|---|---|---|
| 5,661,126 A * | 8/1997 | Donahoe et al. | 514/19.3 |
| 6,673,352 B1 | 1/2004 | Donahoe | |
| 7,119,114 B1 | 10/2006 | Bennett et al. | |
| 7,351,729 B2 * | 4/2008 | Stein et al. | 514/381 |
| 7,781,568 B2 * | 8/2010 | Adams et al. | 530/387.3 |
| 2002/0004587 A1 | 1/2002 | Miller et al. | |
| 2004/0072888 A1 | 4/2004 | Bennett et al. | |
| 2004/0151693 A1 | 8/2004 | Maheswaran et al. | |
| 2006/0162026 A1 | 7/2006 | Oishi et al. | |
| 2006/0188440 A1 | 8/2006 | Adams et al. | |

FOREIGN PATENT DOCUMENTS

| | | | |
|---|---|---|---|
| EP | 0103381 A1 | 3/1984 | |
| EP | 0221761 A2 | 5/1987 | |
| EP | 0584287 | 10/1992 | |
| EP | 0700390 | 11/1994 | |
| WO | 92/18152 A1 | 10/1992 | |
| WO | 92/18153 A1 | 10/1992 | |
| WO | WO 94/00133 A1 | 1/1994 | |
| WO | 94/25441 A1 | 11/1994 | |
| WO | 2006/059121 A2 | 6/2006 | |
| WO | WO 2007125317 * | 8/2007 | G01N 33/50 |

OTHER PUBLICATIONS

Song et al. 2012. In J Oncology 40:2013-2021.*
Renaud et al. 2005. PNAS 102:111-116.*
Mekhail et al. 2002. Expert Opin Pharmacother. 3:755-766.*
Hurley. Nature Reviews Cancer. 2002. 2:190-200.*
Siddik 2003. Oncogene 22:7265-7279.*
Vignot et al. 2005. Annals of Oncology 16:525-537.*
Wang et al 2004. JBC 279:25535-25543.*
Von Bubnoff, A. et al., "Phylogenetic footprinting and genome scanning identify vertebrate BMP response elements and new target genes." Developmental Biology 281:210-226, 2005.
Clarke, T. R. et al., "Mullerian Inhibiting Substance Signaling Uses a Bone Morphogenetic Protein (BMP)-Like Pathway Mediated by ALK2 and Induces Smad6 Expression." Molecular Endocrinology 15:946-959, 2001.
Di Clemente, N. et al., "Components of the anti-Mullerian hormone signaling pathway in gonads." Molecular and Cellular Endocrinolody 211:9-14, 2003.
Ennis, B. W. et al., "Inhibition of Tumor Growth, Angiogenesis, and Tumor Cell Proliferation by a Small Molecule Inhibitor of c-Jun N-terminal Kinase." The Journal of Pharmacology and Experimental Therapeutics 313(1):325-332, 2005.
Gross, N. D. et al., "Inhibition of Jun NH2-Terminal Kinases Suppresses the Growth of Experimental Head and Neck Squamous Cell Carcinoma." Clin Cancer Res 13(19):5910-5917, 2007.
Josso, N. and Di Clemente, N., "Transduction pathway of anti-Mullerian hormone, a sex-specific member of the TGF-beta family," TRENDS in Endocrinology and Metabolism 14(2):91-97, 2003.
Katagiri, T. et al., "Identification of a BMP-responsive element in ID1, the gene for inhibition of myogenesis," Genes to Cells 7:949-960, 2002.
Korchynski, O. and Ten Dijke, P., "Identification and Functional Characterization of Distinct Critically Important Bone Morphogenetic Protein-specific Response Elements in the Id1 Promoter." J Bio Chem 277(7):4883-4891, 2002.

(Continued)

*Primary Examiner* — Shulamith H Shafer
(74) *Attorney, Agent, or Firm* — Nixon Peabody LLP

(57) ABSTRACT

Provided herein are pyrazoloanthrones or functional derivatives or analogs thereof to activate MIS receptor-mediated downstream effects in a cell. In particular, methods are provided to prevent and treat cancer that expresses MIS receptor type II (MISRII) by administering to a subject at least one pyrazoloanthrone or a functional derivative or analog thereof. Also provided herein are methods to lower plasma androgen levels in a subject, and/or for the treatment of a subject with a disease characterized by excess androgen, whereby the subject is administered at least one pyrazoloanthrone or a functional derivative or analog thereof. Also provided are methods to decrease the dose of a chemotherapeutic agent by administering the chemotherapeutic agent with a pyrazoloanthrone or a functional derivative or analog thereof that lowers the effective dose of the chemotherapeutic agent.

7 Claims, 6 Drawing Sheets

(56) References Cited

OTHER PUBLICATIONS

Leopold, W. R. et al., "Anthrapyrazoles, a New Class of Intercalating Agents with High-Level, Broad Spectrum Activity against Murine Tumors." Cancer Res 45:5532-5539, 1985.
Logeart-Avramoglou, D. et al., "An assay for the determination of biologically active bone morphogenetic proteins using cells transfected with an inhibitor of differentiation promoter-luciferase construct." Analytical Biochemistry 349:78-86, 2006.
Xia, H. H-X. et al., "Induction of apoptosis and cell cycle arrest by a specific c-Jun NH2-terminal kinase (JNK) inhibitor, SP-600125, in gastrointestinal cancers." Cancer Letters 241:268-274, 2006.
Accession No. AC024362, Birren et al., submitted Mar. 18, 2003.
Atfi et al., J. Biol. Chem., 272:1429-1432 (1997). "Evidence for a Role of Rho-like GTPases and Stress-activated Protein Kinase/c-Jun N-terminal Kinase (SAPK/JNK) in Transforming Growth Factor β-mediated Signaling."
Baarends et al., Development, 120:189-197 (1994). "A novel member of the transmembrane serine/threonine kinase receptor family is specifically expressed in the gonads and in mesenchymal cells adjacent to the mullerian duct."
Barbie et al., PNAS, 100(26):15601-15606 (2003). "Mullerian Inhibiting Substance inhibits cervical cancer cell growth via a pathway involving p130 and p107."
Behringer et al., Cell, 79:415-425 (1994). "Mullerian-Inhibiting Substance Function during Mammalian Sexual Development."
Bhalla, Oncogene, 22:9075-9086 (2003). "Microtubule-targeted anticancer agents and apoptosis."
Bowie et al., Science, 247(4948):1306-1310 (1990). "Deciphering the Message in Protein Sequences: Tolerance to Amino Acid Substitutions."
Clarke et al., Molecular Endocrinology, 15(6):946-959 (2001). "Mullerian Inhibiting Substance Signaling Uses a Bone Morphogenetic Protein (BMP)-Like Pathway Mediated by ALK2 and Induces Smad6 Expression."
Connolly et al., Cancer Res, 63:1389-1397 (2003). "Female Mice Chimeric for Expression of the Simian Virus 40 TAg under Control of the MISIIR Promoter Develop Epithelial Ovarian Cancer."
Dennler et al., The EMBO Journal, 17(11):3091-3100 (1998). "Direct binding of Smad3 and Smad4 to critical TGFβ-inducible elements in the promoter of human plasminogen activator inhibitor-type 1 gene."
Di Clemente et al., Molecular Endocrinology, 8:1006-1020 (1994). "Cloning, Expression, and Alternative Splicing of the Receptor for Anti-Mullerian Hormone."
Donahoe et al., Journal of Surgical Research, 23:141-148 (1977). "A Graded Organ Culture Assay for the Detection of Mullerian Inhibiting Substance."
Duan et al., Clin Cancer Res, 12:5055-5063 (2006). "Signal Transducers and Activators of Transcription 3 Pathway Activation in Drug-Resistant Ovarian Cancer."
Gupta et al., PNAS, 102(9):3219-3224 (2005). "Mullerian inhibiting substance suppresses tumor growth in the C3(1) T antigen transgenic mouse mammary carcinoma model."
Ha et al., The Journal of Biological Chemistry, 275(47):37101-37109 (2000). "Mullerian Inhibiting Substance Inhibits Ovarian Cell Growth through an Rb-independent Mechanism."
Hazzalin et al., Molecular and Cellular Biology, 18(4):1844-1854 (1998). "Anisomycin Selectively Desensitizes Signalling Components Involved in Stress Kinase Activation and fos and jun Induction."
He et al., Developmental Dynamics, 196:133-142 (1993). "Developmental Expression of Four Novel Serine/Threonine Kinase Receptors Homologous to the Activin/Transforming Growth Factor-62 Type II Receptor Family."
Hoshiya et al., Molecular and Cellular Endocrinology, 211:43-49 (2003). "Mullerian Inhibiting Substance induces NfkB signaling in breast and prostate cancer cells."
Jamin et al., Nature Genetics, 32:408-410 (2002). "Requirement of Bmpr1a for Mullerian duct regression during male sexual development."

Khatlani et al., Oncogene, 26:2658-2666 (2007). "c-Jun N-terminal kinase is activated in non-small-cell lung cancer and promotes neoplastic transformation in human bronchial epithelial cells."
Lemonnier et al., J. Biol. Chem., 279:259-264 (2004). "Protein Kinase C-independent Activation of Protein Kinase D Is Involved in BMP-2-induced Activation of Stress Mitogen-activated Protein Kinases JNK and p38 and Osteoblastic Cell Differentiation."
Lorenzo et al., Journal of Chromatography B, 766:89-98 (2001). "New approaches for high-yield purification of Mullerian inhibiting substance improve its bioactivity."
Massague et al., The EMBO Journal, 19(8):1745-1754 (2000). "Transcriptional control by the TGF-β/Smad signaling system."
Mishina et al., Genes Dev., 10:2577-2587 (1996). "Genetic analysis of the Mullerian-inhibiting substance signal transduction pathway in mammalian sexual differentiation."
Mosmann, Journal of Immunological Methods, 65:55-63 (1983). "Rapid Colorimetric Assay for Cellular Growth and Survival: Application to Proliferation and Cytotoxicity Assays."
Ngo et al., The Protein Folding Problem and Tertiary Structure Predication, Merz et al., eds Birkhauser, Boston, pp. 433-506 (1994).
Park et al., Oncogene, 22:4314-4332 (2003). "Transforming growth factor-β1 activates interleukin-6 expression in prostate cancer cells through the synergistic collaboration of the Smad2, p38-NF-κB, JNK, and Ras signaling pathways."
Perlman et al., Nature Cell Biology, 3:708-715 (2001). "TGF-β-induced apoptosis is mediated by the adapter protein Daxx that facilitates JNK activation."
Pieretti-Vanmarcke et al., Clin Cancer Res, 12(5):1593-1598 (2006). "Recombinant Human Mullerian Inhibiting Substance Inhibits Long-term Growth of MIS Type II Receptor-Directed Transgenic Mouse Ovarian Cancers In vivo."
Pieretti-Vanmarcke et al., PNAS, 103(46):17426-17431 (2006). "Mullerian Inhibiting Substance enhances subclinical doses of chemotherapeutic agents to inhibit human and mouse ovarian cancer."
Segev et al., The Journal of Biological Chemistry, 275(37):28371-28379 (2000). "Mullerian Inhibiting Substance Inhibits Breast Cancer Cell Growth through an NFκB-mediated Pathway."
Sowa et al., J. Biol. Chem., 277:36024-36031 (2002). "Activations of ERK1/2 and JNK by Transforming Growth Factor β Negatively Regulate Smad3-induced Alkaline Phosphatase Activity and Mineralization in Mouse Osteoblastic Cells."
Sriraman et al., J Androl, 22:750-758 (2001). "Mullerian Inhibiting Substance Inhibits Testosterone Synthesis in Adult Rats."
Stephen et al., Clin Cancer Res, 8:2640-2646 (2002). "Highly purified Mullerian Inhibiting Substance Inhibits Human Ovarian Cancer in Vivo."
Suzuki et al., Journal of Bone and Mineral Research, 21(5):674-683 (2006). "Enhanced Expression of the Inorganic Phosphate Transporter Pit-1 Is Involved in BMP-2-Induced Matrix Mineralization in Osteoblast-Like Cells."
Szotek et al., PNAS, 103(30):11154-11159 (2006). "Ovarian cancer side population defines cells with stem cell-like characteristics and Mullerian Inhibiting Substance responsiveness."
Takahashi et al., Biology of Reproduction, 35:447-453 (1986). "The Ontogeny of Mullerian Inhibiting Substance in Granulosa Cells of the Bovine Ovarian Follicle."
Teixeira et al., Endocrinology, 137(1):160-165 (1996). "Developmental Expression of a Candidate Mullerian Inhibiting Substance Type II Receptor."
Texeira et al., Endocrine Reviews, 22(5):657-674 (2001). "Mullerian Inhibiting Substance: An Instructive Developmental Hormone with Diagnostic and Possible Therapeutic Applications."
Tran et al., J Histochem Cytochem, 35:733-743 (1987). "Immunocytochemical Detection fo Anti-Mullerian Hormone in Sertoli Cells of Various Mammalian Species Including Human."
Tran et al., Molecular Endocrinology, 20:2382-2391 (2006). "Mullerian Inhibiting Substance Regulates Androgen-Induced Gene Expression and Growth in Prostate Cancer Cells through a Nuclear Factor-κB-Dependent Smad-Independent Mechanism."
Trbovich et al., PNAS, 98(6):3393-3397 (2001). "Mullerian Inhibiting Substance lowers testosterone in luteinizing hormone-stimulated rodents."

(56) References Cited

OTHER PUBLICATIONS

Visser et al., Molecular Endocrinology, 15(6):936-945 (2001). "The Serine/Threonine Transmembrane Receptor ALK2 Mediates Mullerian Inhibiting Substance Signaling."

Wang et al., The Journal of Biological Chemistry, 276(52):49213-49220 (2001). "A Single Amino Acid Determines Lysophospholipid Specificity of the S1P1 (EDG1) and LPA1 (EDG2) Phospholipid Growth Factor Receptors."

Wang et al., PNAS, 102(45):16421-16425 (2005). "Mullerian Inhibiting Substance acts as a motor neuron survival factor in vitro."

Wang et al., Genes to Cells, 11:983-992 (2006). "Growth suppression of human mast cells expressing constitutively active c-kit receptors by JNK inhibitor SP600125."

Wang et al., Oncogene, 25:4857-4866 (2006). "Paclitaxel (Taxol) upregulates expression of functional interleukin-6 in human ovarian cancer cells through multiple signaling pathways."

Wells, Biochemistry, 29(37):8509-8517 (1990). "Additivity of Mutational Effects in Proteins."

Zhang et al., Int. J. Cancer, 118:2072-2081 (2006). "Inactivation of Id-1 in prostate cancer cells: A potential therapeutic target in inducing chemosensitization to taxol through activation of JNK pathway."

* cited by examiner

SEQUENCE LISTING

<160> NUMBER OF SEQ ID NOS: 5

<210> SEQ ID NO 1
<211> LENGTH: 1629
<212> TYPE: DNA
<213> ORGANISM: Mus musculus

<400> SEQUENCE: 1

```
agagaccctg tctcaaggtg aggccaggtg ctgcacacct ttagtcccag cactggggag      60
gagaccagcc tggtctacac agcaagttct aggacagcca gggctacaca aagaaagctc     120
atcttgaaca acaaacaaa caaacaaaca acaaccagt ggaatggatg cctgcagagg       180
cctagtacct gaggctggcc tgtaatatct ccacacacgc atgctattgc attttaagac     240
```

```
cttggacgag tccagtgttg agcgggagtg agtctaaact gaagatttgc ctggaaattt      300
ctgcctggat atgccactgg agggctttgg gaaattttat ttcttcctta gacctcaatt      360
tccccatctg caaaagaaag ggactgaatc cgagcctgtg tcatatctat gtgttctcat      420
gtttcattgt ctgttgttct cagcccaagc aatggagact cacaagggtg aggtaacgtg      480
ctgttctgtc tccagcacca gcggctgtaa cagtggctgt tttctacaga cagacgctca      540
ccaacctgta aaatgccctt ctgggccaga cagtgggtgc ccacgaataa ggcaaagctg      600
ggacagcatg taagaaaacc acagtgcacc acctaccgtg acttaggaag gcctgcccca      660
cagaaacaat caagatggct aactctgaag tcttcttgtg tgtccggtca agccctgtgc      720
cttggtacca gttttctcat ctcaactcag tccctacccc ctcctcagta gatgctttca      780
cagatgaaca tgctaggcta aaagagccta agaaatagac ccaaggccag ttcgactcag      840
ccactgtcaa gaggcatcct ggaggggctg cctgaattat atggccgagg aaactaaaca      900
tggcgagagg agagggtcca agttcaagat actgtgatag taacagcaaa tactactttt      960
gctgtgggtc ttccagtcct tgaggatcag agtagacatt gaactggggg gttggaagcc     1020
ctgcgggtta gtaaggtgaa gaaaccacac ccgggacctc agtcagtagg cagatcaact     1080
tcacttaggg taattggagg cttataaagt cttgggggc tgaggtagg gacatccaag       1140 atgggcaaag gtcattggct ggggacttag ggtacctgga ctgcctcatt agcacaggga     1200
agcctcttag gaatcttaga tgctggctga tcaggttccc acattttgct aagggcaagg     1260
tactgtgttc taggtacttt ctgcaggaaa cgtgttaagt cctccaagct ggtgatgtca     1320
tcaccatgcc agtttttaaa atgtatttct ttatttactt tatatcctga ttgcagcttc     1380
ccctccctcc tctccccca gtccctccct ctcccctcc ttcctgcaat tcctcctcct       1440
tttctcctcc tcggagggga ggtctcccac gggtatcaac ccgccttggc agtagggctg     1500
ggtgcatctt ctcctattga gcctaaacaa ggcagttcag ttaggggaga gaggtttaaa     1560
ggcagacaac aaagtccgag acaaccctgc tccagttatt atgggtccca cacgaagacc     1620
aagctacac                                                             1629

<210> SEQ ID NO 2
<211> LENGTH: 2065
<212> TYPE: DNA
<213> ORGANISM: Homo sapiens

<400> SEQUENCE: 2
gcatgttgac acatcaggcc cagctctatc actgggagg gagataggct gccagggaca       60
gaaagggctc tttgagaagg ccactctgcc tggagtgggg gcgccgggca ctgtccccca     120
aggtcgcggc agaggagata ggggtctgtc ctgcacaaac accccacctt ccactcggct     180
cacttaaggc aggcagccca gcccctggca gcacccacga tgcgggacct gcctctcacc     240
agcctggccc tagtgctgtc tgccctgggg gctctgctgg ggactgaggc cctcagagca     300
gaggagccag ctgtgggcac cagtggcctc atcttccgag aagacttgga ctggcctcca     360
ggcagcccac aagagcctct gtgcctggtg gcactgggcg gggacagcaa tggcagcagc     420
tcccccctgc gggtggtggg ggctctaagc gcctatgagc aggccttcct gggggccgtg     480
cagagggccc gctggggccc ccgagacctg gccaccttcg ggtctgcaa caccggtgac      540 aggcaggctg ccttgcccte tctacggcgg ctgggggcct ggctgcggga ccctgggggg     600
cagcgcctgg tggtcctaca cctggaggaa gtgacctggg agccaacacc ctcgctgagg     660
ttccaggagc cccgcctgg aggagctggc ccccagagc tggcgctgct ggtgctgtac       720
```

```
cctgggcctg gccctgaggt cactgtgacg agggctgggc tgccgggtgc ccagagcctc      780
tgcccctccc gagacacccg ctacctggtg ttagcggtgg accgccctgc gggggcctgg      840
cgcggctccg ggctggcctt gaccctgcag ccccgcggag aggactcccg gctgagtacc      900
gcccggctgc aggcactgct gttcggcgac gaccaccgct gcttcacacg gatgaccccg      960
gccctgctcc tgctgccgcg gtccgagccc gcgccgctgc ctgcgcacgg ccagctggac     1020
accgtgccct tccgccgcc caggccatcc gcggaactcg aggagtcgcc acccagcgca      1080
gaccccttcc tggagacgct cacgcgcctg gtgcgggcgc tgcgggtccc ccggcccgg      1140 gcctccgcgc cgcgcctggc cctggatccg gacgcgctgg ccggcttccc gcagggccta     1200
gtcaacctgt cggaccccgc ggcgctggag cgcctactcg acggcgagga gccgctgctg     1260
ctgctgctga ggcccactgc ggccaccacc ggggatcctg cgcccctgca cgaccccacg     1320
tcggcgccgt gggccacggc cctggcgcgc cgcgtggctg ctgaactgca agcggcggct     1380
gccgagctgc gaagcctccc gggtctgcct ccggccacag cccgctgct ggcgcgcctg      1440 ctcgcgctct gcccaggtgg ccccggcggc ctcggcgatc ccctgcgagc gctgctgctc     1500
ctgaaggcgc tgcagggcct gcgcgtggag tggcgcgggc gggatccgcg cgggccgggt     1560
cgggcacagc gcagcgcggg ggccaccgcc gccgacgggc cgtgcgcgct gcgcgagctc     1620
agcgtagacc tccgcgccga gcgctccgta ctcatccccg agacctacca ggccaacaat     1680
tgccagggcg tgtgcggctg gcctcagtcc gaccgcaacc cgcgctacgg caaccacgtg     1740
gtgctgctgc tgaagatgca ggcccgtggg gccgccctgg cgcgccacc ctgctgcgtg      1800 cccaccgcct acgcgggcaa gctgctcatc agcctgtcgg aggagcgcat cagcgcgcac     1860
cacgtgccca acatggtggc caccgagtgt ggctgccggt gacccctgcg ccgcgcggac     1920
tcctgccccg agggtccgga cgcgcccag ctcgcgcccc ttcccatatt tattcggacc      1980
ccaagcatcg ccccaataaa gaccagcaag caaccggcaa aaaaaaaaa aaaaaaaaa       2040 aaaaaaaaaa aaaaaaaaaa aaaaa                                           2065

<210> SEQ ID NO 3
<211> LENGTH: 3100
<212> TYPE: DNA
<213> ORGANISM: Homo sapiens

<400> SEQUENCE: 3
cacatcaggc ccagctctat cactggggag ggagataggc tgccagggac agaaagggct       60
ctttgagaag gccactctgc ctggagtggg ggcgccgggc actgtccccc aaggtcgcgg      120
cagaggagat aggggtctgt cctgcacaaa caccccacct tccactcggc tcacttaagg      180
caggcagccc agccctggc agcacccacg atgcgggacc tgcctctcac cagcctggcc      240
ctagtgctgt ctgccctggg ggctctgctg gggactgagg ccctcagagc agaggagcca      300
gctgtgggca ccagtggcct catcttccga gaagacttgg actggcctcc aggcatccca     360
caagagcctc tgtgcctggt ggcactgggc ggggacagca atggcagcag ctcccccctg     420
cgggtggtgg gggctctaag cgcctatgag caggccttcc tggggccgt gcagagggcc      480 cgctggggcc cccgagacct ggccaccttc ggggtctgca acaccggtga caggcaggct     540
gccttgccct ctctacggcg gctggggggcc tggctgcggg acctggggg gcagcgcctg      600 gtggtcctac acctggagga aggtatgtgg ggcccagccc caagcttggc accgcgtct       660 tccttcaggt gggccgggtc ctcctaggga agatcagggg ctggcagagc ccccacccctg     720
```

```
ggcagggagg ctgtggtctt gttcctagga ctgggttgcg ggtccgtggc ctggaaggtg    780
ggcaccacac tctgtcctgt ccccgaagcc cagctcttag acttgcccct gcctcggtgc    840
cagggagaga gctgctgcct ctccccaccc cctgaagacg acgcagggct cggggccagt    900
ggaacccttc ttcccacagc cccagcctgt tctcagggcc gctggcctaa gatactccct    960
gcggggaagg ggcttcatcg ggcaccccaa cccagagacc caggggcggc agccccaccc   1020
acagcctcag acgcagcccc tgcctgcccc tgccgtcacc gctccctggc tgcaggaagg   1080
cagctaagag gggcacccct tgtccccgct tgaggtcccc tgcacagtgg ccagagcggc   1140
agggacagat cccaaagatt cccgggggt gtggccttca atggctcagg cgtccctgc   1200 tgtcccggct gcagtgacct gggagccaac accctcgctg aggttccagg agccccgcc   1260 tggaggagct ggccccccag agctggcgct gctggtgctg taccctgggc ctggccctga   1320
ggtcactgtg acgagggctg ggctgccggg tgcccaggta ccagggagtt gcatggggca   1380
gtgcccgggc cgtggcgggg ggcatgaatt tgttgcaggg tctgcagtac tgagaacagc   1440
gtagaaccag tggcgatggg aggaagggga ccggtagagc ggggctgggt aagcctccat   1500
ccagccgggc tgagccctgg tctccgcaga gcctctgccc ctcccgagac acccgctacc   1560
tggtgttagc ggtggaccgc cctgcggggg cctggcgcgg ctccgggctg gccttgaccc   1620
tgcagccccg cggagagggt aggtccgcgt ggagagggac ggggagccgg gtcgactgcc   1680
cccgggcccc cagcccctga ccagccgcg tgcccaccca ccgcagactc ccggctgagt   1740
accgcccggc tgcaggcact gctgttcggc gacgaccacc gctgcttcac acggatgacc   1800
ccggccctgc tcctgctgcc gcggtccgag cccgcgccgc tgcctgcgca cggccagctg   1860
gacaccgtgc ccttcccgcc gcccaggtgc gcgcaggcac cgggacacgg ggcaggagcg   1920
ggcgggggcg cgtggcctc gtggccgctc tcaactcctc caattgcggg ttccaggcca   1980
tccgcggaac tcgaggagtc gccacccagc gcagacccct tcctggagac gctcacgcgc   2040
ctggtgcggg cgctgcgggt ccccccgcc cgggcctccg cgccgcgcct ggccctggat   2100
ccggacgcgc tggccggctt cccgcagggc ctagtcaacc tgtcggaccc cgcggcgctg   2160
gagcgcctac tcgacggcga ggagccgctg ctgctgctgc tgaggcccac tgcggccacc   2220
accggggatc ctgcgcccct gcacgacccc acgtcggcgc cgtgggccac ggccctggcg   2280
cgccgcgtgg ctgctgaact gcaagcgcg gctgccgagc tgcgaagcct cccgggtctg   2340
cctccggcca cagccccgct gctggcgcgc ctgctcgcgc tctgcccagg aggccccggc   2400
ggcctcggcg atcccctgcg agcgctgctg ctcctgaagg cgctgcaggg cctgcgcgtg   2460
gagtggcgcg ggcgggatcc gcgcgggccg ggtcgggcac agcgcagcgc ggggggccacc   2520 gccgccgacg ggccgtgcgc gctgcgcgag ctcagcgtag acctccgcgc cgagcgctcc   2580
gtactcatcc ccgagaccta ccaggccaac aattgccagg gcgtgtgcgg ctggcctcag   2640
tccgaccgca acccgcgcta cggcaaccac gtggtgctgc tgctgaagat gcaggcccgt   2700
ggggccgccc tggcgcgccc accctgctgc gtgcccaccg cctacgcggg caagctgctc   2760
atcagcctgt cggaggaacg catcagcgcg caccacgtgc ccaacatggt ggccaccgag   2820
tgtggctgcc ggtgacccct gcgcgcgcg gactcctgcc ccgagggtcc ggacgcgccc   2880
cagctcgcgc cccttcccat atttattcgg accccaagca tcgccccaat aaagaccagc   2940
aagcaaccgg ctggggtgtc cgtgcgtgtt aggggggccg tgggacctcc cttgccgtct   3000
ctcctcgcgc acgcccggg tccgccctgt agcgctcgct gtctctcccc tgcctgaagc   3060
gccccaccac cgtctttcag gccccggact tggtgccggg                          3100
```

<210> SEQ ID NO 4
<211> LENGTH: 1855
<212> TYPE: DNA
<213> ORGANISM: Homo sapiens

<400> SEQUENCE: 4

```
atctgaagaa agatttggcc aggggcagct gtgctggctt atgctcttct ccttctgctg      60
ctgccatcct ccagcaagat gctagggtct ttggggcttt gggcattact tcccacagct     120
gtggaagcac ccccaaacag gcgaacctgt gtgttctttg aggcccctgg agtgcgggga     180
agcacaaaga cactgggaga gctgctagat acaggcacag agctcccag agctatccgc      240
tgcctctaca gccgctgctg ctttgggatc tggaacctga cccaagaccg ggcacaggtg     300
gaaatgcaag gatgccgaga cagtgatgag ccaggctgtg agtccctcca ctgtgaccca     360
agtccccgag cccacccccag ccctggctcc actctcttca cctgctcctg tggcactgac     420
ttctgcaatg ccaattacag ccatctgcct cctccaggga ccctgggac tcctggctcc      480
cagggtcccc aggctgcccc aggtgagtcc atctggatgg cactggtgct gctgggctg      540
ttcctcctcc tcctgctgct gctgggcagc atcatcttgg ccctgctaca gcgaaagaac     600
tacagagtgc gaggtgagcc agtgccagag ccaaggccag actcaggcag ggactggagt     660
gtggagctgc aggagctgcc tgagctgtgt ttctcccagg taatccggga aggaggtcat     720
gcagtggttt gggccgggca gctgcaagga aaactggttg ccatcaaggc cttcccaccg     780
aggtctgtgg ctcagttcca agctgagaga gcattgtacg aacttccagg cctacagcac     840
gaccacattg tccgatttat cactgccagc cgggggggtc ctggccgcct gctctctggg     900
cccctgctgg tactggaact gcatcccaag ggctccctgt gccactactt gacccagtac    960
accagtgact ggggaagttc cctgcggatg gcactgtccc tggcccaggg cctggcattt    1020
ctccatgagg agcgctggca gaatggccaa tataaaccag gtattgccca ccgagatctg    1080
agcagccaga atgtgctcat tcgggaagat ggatcgtgtg ccattggaga cctgggcctt    1140
gccttggtgc tccctggcct cactcagccc cctgcctgga cccctactca accacaaggc    1200
ccagctgcca tcatggaagc tggcacccag aggtacatgg caccagagct cttggacaag    1260
actctggacc tacaggattg gggcatggcc ctccgacgag ctgatattta ctctttggct    1320
ctgctcctgt gggagatact gagccgctgc ccagatttga ggcctgacag cagtccacca    1380
cccttccaac tggcctatga ggcagaactg ggcaataccc ctacctctga tgagctatgg    1440
gccttggcag tgcaggagag gaggcgtccc tacatcccat ccacctggcg ctgctttgcc    1500
acagaccctg atgggctgag ggagctccta gaagactgtt gggatgcaga cccagaagca    1560
cggctgacag ctgagtgtgt acagcagcgc ctggctgcct tggccatcc tcaagagagc    1620
cacccctttc cagagagctg tccacgtggc tgccccacctc tctgcccaga agactgtact    1680
tcaattcctg ccccctaccat cctcccctgt aggcctcagc ggagtgcctg ccacttcagc    1740
gttcagcaag gcccttgttc caggaatcct cagcctgcct gtaccctttc tcctgtgtaa    1800
atatgcagtt tatgtgtcat caatgtacat gccaacataa atatggcgat tgtat          1855
```

<210> SEQ ID NO 5
<211> LENGTH: 1846
<212> TYPE: DNA
<213> ORGANISM: Homo sapiens

```
<400> SEQUENCE: 5
ggcacgaggg cagctgtgct ggcttatgct cttctccttc tgctgctgcc atcctccagc      60
aagatgctag ggtctttggg gctttgggca ttacttccca cagctgtgga agcaccccca     120
aacaggcgaa cctgtgtgtt ctttgaggcc cctggagtgc ggggaagcac aaagacactg     180
ggagagctgc tagatacagg cacagagctc cccagagcta tccgctgcct ctacagccgc     240
tgctgctttg ggatctggaa cctgacccaa gaccgggcac aggtggaaat gcaaggatgc     300
cgagacagtg atgagccagg ctgtgagtcc ctccactgtg acccaagtcc ccgagcccac     360
cccagccctg gctccactct cttcacctgc tcctgtggca ctgacttctg caatgccaat     420
tacagccatc tgcctcctcc agggagccct gggactcctg gctcccaggg tccccaggct     480
gccccaggtg agtccatctg gatggcactg gtgctgctgg ggctgttcct cctcctcctg     540
ctgctgctgg gcagcatcat cttggccctg ctacagcgaa agaactacag agtgcgaggt     600
gagccagtgc cagagccaag gccagactca ggcagggact ggagtgtgga gctgcaggag     660
ctgcctgagc tgtgtttctc ccaggtaatc cgggaaggag gtcatgcagt ggtttgggcc     720
gggcagctgc aaggaaaact ggttgccatc aaggccttcc caccgaggtc tgtggctcag     780
ttccaagctg agagagcatt gtacgaactt ccaggcctac agcacgacca cattgtccga     840
tttatcactg ccagccgggg gggtcctggc cgcctgctct ctgggcccct gctggtactg     900
gaactgcatc ccaagggctc cctgtgccac tacttgaccc agtacaccag tgactgggga     960
agttccctgc ggatggcact gtccctggcc cagggcctgg catttctcca tgaggagcgc    1020
tggcagaatg gccaatataa accaggtatt gcccaccgag atctgagcag ccagaatgtg    1080
ctcattcggg aagatggatc atgtgccatt ggagacctgg gccttgcctt ggtgctccct    1140
ggcctcactc agcccctgc ctggacccct actcaaccac aaggcccagc tgccatcatg    1200
gaagctggca cccagaggta catggcacca gagctcttgg acaagactct ggacctacag    1260
gattggggca tggccctccg acgagctgat atttactctt tggctctgct cctgtgggag    1320
atactgagcc gctgcccaga tttgaggcct gacagcagtc caccacccct ccaactggcc    1380
tatgaggcag aactgggcaa taccccctacc tctgatgagc tatgggcctt ggcagtgcag    1440
gagaggaggc gtccctacat cccatccacc tggcgctgct ttgccacaga ccctgatggg    1500
ctgagggagc tcctagaaga ctgttgggat gcagacccag aagcacggct gacagctgag    1560
tgtgtacagc agcgcctggc tgccttggcc catcctcaag agagccaccc ctttccagag    1620
agctgtccac gtggctgccc acctctctgc ccagaagact gtacttcaat tcctgcccct    1680
accatcctcc cctgtaggcc tcagcggagt gcctgccact tcagcgttca gcaaggccct    1740
tgttccagga atcctcagcc tgcctgtacc ctttctcctg tgtaaatatg cagtttatgt    1800
gtcatcaatg tacatgccaa cataaatatg gcgattgtat agctgt                   1846
```

PYRAZOLOANTHRONE AND DERIVATIVES THEREOF FOR THE TREATMENT OF CANCERS EXPRESSING MISRII

CROSS REFERENCED APPLICATIONS

This application is a Continuation Application under 35 U.S.C. §120 of co-pending U.S. application Ser. No. 12/532,533, filed May 12, 2010, which claims benefit of International Application PCT/US2008/057837, filed 21 Mar. 2008, which claims benefit under 35 U.S.C. 119(e) of U.S. Provisional Application Ser. No. 60/919,429, filed on Mar. 22, 2007 the contents of which are incorporated herein in their entirety by reference

GOVERNMENT SUPPORT

This application was made with government support under Grant No CA017393-30S1 awarded by the National Institutes for Health (NIH). The Government of the United States has certain rights in the invention.

BACKGROUND OF THE INVENTION

Cancer is characterized by uncontrolled growth, proliferation, and migration of cells. Cancer is the second leading cause of death with 500,000 deaths and an estimated 1.3 million new cases in the United States in 1996. The role of signal transduction pathways contributing to cell transformation and cancer is a generally accepted concept.

Müllerian Inhibiting Substance (MIS) is a glycoprotein hormone secreted by the newly differentiating testis during the fetal period where it is responsible for regression of the Müllerian ducts in males, which would otherwise develop into the internal female reproductive tract tissues (Reviewed in (Teixeira, 2001)). However, MIS is also produced during postnatal life in both male and female gonads (Takahashi, 1986, Tran, 1987). As a member of the transforming growth factor-β (TGF-α) family, MIS signaling requires a set of membrane bound serine/threonine kinase receptors (Baarends, 1994, Clarke, 2001a, di Clemente, 1994, He, 1993, Jamin, 2002, Teixeira, 1996, Visser, 2001). After the type II receptor for MIS (MISRII) binds the MIS ligand, it recruits, phosphorylates, and activates one of three possible, activin-like kinase type I receptors (Alk2 or 3), which in turn activates the Smad 1/5/8 pathway in concert with the common Smad4. The Smad complex will translocate into the nucleus and bind to promoter regions to activate transcription of MIS-responsive genes (Massague and Wotton, 2000).

In addition to its role during male fetal development, the continuous production of this hormone in both male and females after birth indicates a function in the adult. One of the activities that has been ascribed to postnatal MIS has been as a inhibitor of tumor cell proliferation, including cells from breast (Gupta, 2005, Segev, 2000), prostate (Hoshiya, 2003, Tran, 2006), cervical (Barbie, 2003), endometrial (Renaud, 2005) and ovarian (Ha, 2000, Stephen, 2002) cancers. Since, the type II receptor for MIS is highly expressed only in the gonads and other reproductive tract organs, targeting this receptor should give rise to a selective agent and minimize side effects associated with other systemic therapy. MISRII is expressed in motor neurons (Wang, 2005) but the effect is salutary rather than inhibitory as in tumors.

However, the production of large quantities of purified, biologically active MIS sufficient to be used therapeutically is challenging. Therefore, it would be desirable to have a simple molecule that could mimic the effect of MIS by selectively activating the MISRII-mediated downstream signaling pathway.

SUMMARY OF THE INVENTION

The inventors have discovered that pyrazoloathrones or derivatives thereof act as a MIS mimetic. The present invention relates to the use of pyrazoloathrones or derivatives thereof to activate MIS receptor-mediated downstream effects that result in the inhibition of tumor cell proliferation, for example inhibition of MISRII positive tumors.

The present invention is based on the discovery that pyrazoloathrone or functional derivative thereof can mimic the effect of MIS by selectively activating the MIS type II receptor (MISRII)-mediated downstream signaling pathway. The inventors have also discovered that in the presence of pyrazoloathrone or derivative thereof, a lower effective concentration of MIS and/or other agents can be used in the treatment of cancers expressing MIS receptors, for example cancer expressing MISRII. Examples of such agents are, for example but not limited to, chemotherapy agents such as paclitaxel for the treatment of cancers expressing MIS receptors, for example cancer expressing MISRII. In other embodiments, the agent is a MIS mimetic. In some embodiments the cancer expressing MIS receptors, for example cancer expressing MISRII is, for example, ovarian cancer and cervical cancer.

Accordingly, one aspect of the present invention relates to methods for the treatment of cancers expressing MIS receptors, for example cancer expressing MISRII. In some embodiments, the subject is at risk of developing, or has a cancer expressing MIS receptors, for example the subject is at risk of developing or has a cancer expressing MISRII. The present invention provides methods to treat cancer expressing MIS receptors, for example cancer expressing MISRII by administering to the subject a pharmaceutical composition comprising a pyrazoloathrone or derivative or analogue thereof. The present invention relates to a method to treat cancers expressing MIS receptors, for example cancer expressing MISRII, the method comprising contacting a cell with a pyrazoloathrone or derivative or analogue thereof. In some embodiments the pyrazoloathrone is antra(1,9-cd)pyrazol-6(2H)-one or an analogue or derivative thereof. In some embodiments, the cell, for example a cancer cell expressing MISRII is also contacted with agents in addition to the pyrazoloathrone or derivative or analogue thereof, and in some embodiments, the agents are therapeutic agents and/or chemotherapeutic agents. The cell expressing MIS receptors or MISRII can be any cell of any type. In some embodiments, the cell is a cancer cell expressing MIS receptors, for example a cancer cell expressing MISRII.

In another embodiment, a biological sample is obtained from the subject and assessed for the expression of a MIS receptor, for example for the expression of MISRII, and if the presence of expression and/or activity of the MIS receptor, for example MISRII is detected, the subject is administered a pharmaceutical composition comprising a pyrazoloathrone or derivative or analogue thereof. In another embodiment, the pharmaceutical composition comprising pyrazoloathrone or derivative or analogue thereof are administered with additional agents. Additional agents include, for example but not limited to, therapeutic agents and/or chemotherapeutic agents or MIS itself.

In another aspect of the present invention, the methods relate to the use of pyrazoloathrone and functional derivatives thereof for the treatment of any disorder where administration of the MIS protein or a nucleic acid encoding MIS protein or activation of MISRII is whole, or part, of the therapeutic regime. In some embodiments, the pyrazoloathrone is SP600125, as disclosed in U.S. patent application Ser. No. 7,119,114 which is specifically incorporated herein in its entirety by reference. In other embodiments, the pyrazoloathrone is a derivative of pyrazoloathrone, for example substituted antra(1,9-cd)pyrazol-6(2H)-one, and anthrapyrazolone functional derivatives as disclosed in European Patent EP0103381 and EP0700390, which are incorporated herein in their entirety by reference.

In some embodiments, the pyrazoloanthrone, for example antra(1,9-cd)pyrazol-6(2H)-one (herein also referred to as SP600125 or Compound I). In alternative embodiments, the pyrazoloanthrone is a functional derivative of a pyrazoloanthrone, and may generally be classified as "pyrazoloanthrone derivatives" having the following structure (I), also referred to herein as Compound (II):

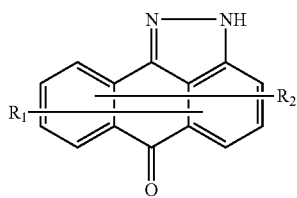

wherein $R_1$ and $R_2$ are as defined below, including pharmaceutically acceptable salts thereof. Pyrazoloanthrone, for example antra(1,9-cd)pyrazol-6(2H)-one (herein also referred to as SP600125 or Compound II) and pyrazoloanthrone derivatives (having the structure (I) are disclosed in U.S. patent application Ser. No. 7,119,114 which is incorporated in its entirety herein by reference.

In some embodiments, the disorder is a proliferative disease where the proliferative disease is associated with cells expressing MIS receptors, for example cells expressing MISRII. One example of such a proliferative disease is, for example a cancer expressing MIS receptors or a cancer expressing MISRII. In some embodiments, the cancer is also a MIS-responsive cancer, for example but not limited ovarian cancer and cervical cancer. In some embodiments, the cancer expresses MISRII, for example but not limited ovarian cancer and cervical cancer. In some embodiments, the disorder is a disorder associated with excess androgen states, for example as disclosed in U.S. Pat. No. 6,673,352, which is incorporated in its entirety herein by reference. In some embodiments, the methods of the present invention are used in the treatment of prostatic cancer, polycysic ovarian disease, benign prostatic hypertrophy and precocious puberty.

The present invention is also directed towards methods for treating cancers expressing MIS receptors, for example cancer expressing MISRII by administering an effective amount of the pyrazoloathrone and functional derivatives thereof to a subject in need thereof. Accordingly the compounds of the present invention are useful in treatment of cancers expressing the MIS type II receptor (MISRII), for example ovarian cancers. The compounds of the present invention are also useful in treatment of other cancers expressing MIS receptors, for example other cancer expressing MISRII, for example cervical, breast, and prostate cancer. In some embodiments, the cancer is a cancer cell expressing MIS receptors, for example cancer expressing MISRII. In some embodiments, the cancer cell expressing MIS receptors and/or MISRII is an ovarian cancer cell, vulvar epidermal carcinoma cell, cervical carcinoma cell, endometrial adenocarcinoma cell and ovarian adenocarcinoma.

In alternative embodiments, the cancer expressing MIS receptors, for example cancer expressing MISRII is, for example but not limited to breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, osteosarcomas, thyroid cancer, prostate cancer, colon cancer, prostate cancer, skin cancer, stomach cancer, testis cancer, tongue cancer, or uterine cancer.

Accordingly, one aspect of the present invention relates to a method for treating a cancer in a subject, the method comprising administering to the subject an effective amount of a pharmaceutical composition comprising a pyrazoloanthrone or a functional derivative or a functional analogue thereof, wherein the subject is determined to have a cancer expressing a Mullerian Inhibiting Substance (MIS) receptor. In some embodiments, the pyrazoloanthrone is anthra[1,9-cd]pyrazol-6(2H)-one or functional derivative or functional analogue thereof, and the cancer expresses the MIS Type II receptor (MISRII) or a homologue or functional fragment thereof.

In some embodiments, a biological sample is harvested from the subject to determine if the cancer expresses MIS receptor, and in some embodiments, the biological sample is a tissue sample, for example a cancer or tumor tissue sample or a cancer cell or tumor cell, or a biopsy tissue sample.

In some embodiments, the methods to treat a cancer as disclosed herein are useful for the treatment where the cancer comprises, for example but not limited to, an ovarian cancer cell, a vulvar epidermal carcinoma cell, a cervical carcinoma cell, an endometrial edenocarinaoma cell and/or an ovarian adenocarcinoma cell. In alternative embodiments, the methods to treat a cancer as disclosed herein are useful for the treatment of cancers such as, but not limited to, breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, gum cancer, kidney cancer, liver cancer, nasopharynx cancer, ovarian cancer, prostate cancer, skin cancer, stomach cancer, testis cancer, tongue cancer, or uterine cancer. In some embodiments, the cancer is a multi-drug resistant cancer, for example, a paclitaxel-resistant cancer.

In some embodiments in the methods to treat a cancer as disclosed herein, one can measure the expression of the nucleic acid gene product or protein or polypeptide gene product of the MIS receptor.

In some embodiments in the methods to treat a cancer as disclosed herein, one can administer the pyrazoloanthrone or a functional derivative or a functional analogue thereof by intravenous, intradermal, intramuscular, intraarterial, intralesional, percutaneous, subcutaneous, or by aerosol. In some embodiments, the administering is prophylactic administration, and alternative embodiments, the administering is therapeutic administration.

In some embodiments in the methods to treat a cancer as disclosed herein, the subject is a mammal, such as for example but not limited to, a human.

In some embodiments in the methods to treat a cancer as disclosed herein, one or more additional agents can be administered to the subject in addition to the pyrazoloanthrone or a functional derivative or a functional analogue thereof, for example, where the agents are therapeutic agents such as chemotherapeutic agents. In some embodiments, the chemotherapeutic agents include, but are not limited to, paclitaxel, cisplatin, doxorubicin or rapamycin. In alternative embodiments, an additional agent can be, for example, Mullerian Inhibiting Substance (MIS) or a functional derivative or variant thereof, such as recombinant human MIS (rhMIS). In some embodiments, the additional agent is a radiotherapeutic agent.

In some embodiments in the methods to treat a cancer as disclosed herein, one can administer the pyrazoloanthrone or a functional derivative or a functional analogue thereof more than once. In some embodiments, a pyrazoloanthrone or functional derivative or functional analogue can be administered before, after or at the same time as the additional agent, and in some embodiments, an additional therapeutic agent can be administered more than once via any route commonly know by persons of ordinary skill in the art, such as intravenous, intradermal, intramuscular, intraarterial, intralesional, percutaneous, subcutaneous, or by aerosol administration.

Another aspect of the present invention relates to a pharmaceutical composition comprising at least one pyrazoloathrone or at least one functional derivatives thereof, which can can be used alone or in combination with additional agents. In alternative embodiments, the pharmaceutical composition comprising pyrazoloathrone and functional derivatives thereof can be used in combination with other therapeutic agents and additional therapies. In some embodiments, the additional therapies are, for example but not limited to chemotherapy, radiotherapy, thermotherapy, immunotherapy, hormone therapy, surgery and laser therapy.

In some embodiments, the present invention relates to a pharmaceutical composition comprising an activator of MIS-RII and a pharmaceutical acceptable carrier, for example where the activator of MISRII is a pyrazoloanthrone or a functional derivative or functional analogue thereof, such as for example, a anthra[1,9-cd]pyrazol-6(2H)-one or a functional derivative or functional analogue thereof. In some embodiments, the pharmaceutical composition can further comprise one or more additional agents, such as therapeutic agents for example, chemotherapeutic agents and/or a radiotherapeutic agent. In some embodiments, a chemotherapeutic agents which can be included in the pharmaceutical composition can be, for example but are not limited to, paclitaxel, cisplatin, doxorubicin or rapamycin or analogues or functional derivatives thereof. In some embodiments, an additional agent which can be added to the pharmaceutical compositions as disclosed herein can be, for example, Mullerian Inhibiting Substance (MIS) or a functional derivative or functional variant thereof, such as recombinant human MIS (rhMIS). Other examples of therapeutic agents which can be added or administered to the subject in addition to the pharmaceutical compositions as disclosed herein can be, but are not limited to, are paclitaxel, cisplatin, and any other or combination of chemotherapy agents commonly known by person of ordinary skill in the art. In some embodiments, the therapeutic agent is MIS and/or recombinant or modified version of MIS, for example rhMIS, or a functional derivatives of MIS, as disclosed in International Patent Application WO92/18152, which is incorporated herein in its entirety by reference. In some embodiments, the other therapeutic agent is in interferon, for example as disclosed in U.S. Patent Application 2004/0151693, which is incorporated herein in its entirety by reference.

Accordingly, the methods of the present invention are directed to use of pyrazoloathrone and functional derivatives thereof with other therapeutic agents, for example chemotherapy agents, wherein the chemotherapy agents, for example paclitaxel and/or MIS can be used at a lower dose as compared to when they are used in the absence of the pyrazoloathrone or functional derivative thereof. Accordingly, where the chemotherapeutic, such as paclitaxel or MIS are used at a lower dose, this often results in decreased side effects associated with use of such chemotherapeutics such as paclitaxel or MIS.

Another aspect of the present invention relates to methods of increasing the sensitivity of a tumor cell to chemotherapeutic agent, the method comprising administering to the cell a therapeutically effective amount of a pyrazoloanthrone or functional derivative or functional analogue thereof. A similar aspect of the present invention relates to a method of decreasing the dose of a chemotherapeutic agent for the treatment of cancer, the method comprising administering to the subject a therapeutically effective amount of a pyrazoloanthrone or functional derivative or functional analogue thereof and a chemotherapeutic agent, wherein the therapeutically effective dose of the chemotherapeutic agent in the presence of the pyrazoloanthrone or functional derivative or functional analogue is lower or at a decreased dose as compared to the therapeutically effective dose of the chemotherapeutic agent when used alone or in the absence of the pyrazoloanthrone or functional derivative or functional analogue thereof. In some embodiments, the a pyrazoloanthrone which is used to increase the sensitivity of a tumor cell, and/or decrease the dose of a chemotherapeutic agents is anthra[1,9-cd]pyrazol-6(2H)-one or derivative or analogue thereof. In some embodiments, such a chemotherapeutic agent is, for example, but not limited to, paclitaxel, cisplatin, doxorubicin, rapamycin or functional derivatives thereof. In alternative embodiments, the chemotherapeutic agent is Mullerian Inhibiting Substance (MIS) or a functional derivative or variant thereof, such as, for example but not limited to, recombinant human MIS (rhMIS). In some embodiments, the pyrazoloanthrone or functional derivative or functional analogue thereof can be administered to the subject or to the tumor cell at the same time, or prior to, or following the administration of a chemotherapeutic agent, as disclosed herein.

In some embodiments, the present invention provides methods for manufacture of a medicament for reducing cancer where the cancer is a MIS-responsive cancer, where the medicament comprises a pharmaceutical composition of pyrazoloathrone and functional derivatives thereof, with or without additional therapeutic agents, as discussed above.

In another aspect, the present invention is directed to methods of screening for agents or molecules that function as a mimetic of MIS or activate the MISRII or activate MISRII-mediated signaling. In some embodiments, the present invention provides methods an assay, wherein the agent is contacted with a cell comprising a nucleic acid construct comprising a BMP-responsive element operatively linked to a nucleic acid encoding a reporter gene. In some embodiments, the reporter gene encodes a protein with fluorescent activity and/or chromogenic activity, for example but not limited to fluorescent proteins, for example green fluorescent protein (GFP) or variants thereof or bioluminescent proteins, for example luciferase or variants thereof. In some embodiments, the cell also comprises a nucleic acid construct comprising MISRII. In some embodiments, the agent is a small molecule, nucleic acid, nucleic acid analogue, aptamer, ribosome, peptide, protein, antibody or variants or fragments thereof. An agent that functions as a MIS mimetic or functional derivative of MIS or activates MISRII-mediated signaling will result in a change in the signal from the reporter gene, where the change is a result of contacting the cell with agent compared to when the cell is not contacted with the agent.

In some embodiments, the present invention provides methods of identify an agent that modulates MISRII-mediated signal transduction in a cell, the methods comprising; (a) providing a cell containing a nucleic acid construct comprising a nucleic acid sequence encoding a BMP-responsive element (BME) or fragment thereof, which is operatively linked to a nucleic acid sequence encoding a reporter gene; and (b) contacting the cell or an extract of the cell with an agent; and (c) measuring the signal from the reporter gene, whereby a change in the signal from the reporter gene in the presence of the agent compared to the signal from the reporter gene in the absence of the agent indicates the agent modulates MISRII-mediated signal transduction. In some embodiments, where the change is an increase in the signal in step (c) indicates the agent activates and/or increases MISRII mediated signal transduction, whereas where the change is a decrease in the signal in step (c) indicates the agent inhibits and/or decreases MISRII mediated signal transduction. In some embodiments, the method to identify an agent that modulates MISRII-mediated signal transduction in a cell further comprises introducing a nucleic acid construct into the cell, where the nucleic acid sequence encodes MISRII or a homologue or fragment thereof, wherein the nucleic acid sequence encoding MISRII is operatively linked to a promoter, such as, for example a constitutive or inducible or tissue-specific promoter.

In some embodiments, the BMP-responsive element used in the method to identify an agent that modulates MISRII-mediated signal transduction is SEQ ID NO: 1 or a functional fragment thereof. In some embodiments, the reporter gene in the method to identify an agent that modulates MISRII-mediated signal transduction encodes a protein with fluorescent and/or chromogenic activity or variants or functional fragments thereof, for example, a chromogenic protein can be a bioluminescent protein or functional variants thereof, such as but not limited to a luciferase or functional fragments or modified functional versions thereof.

In some embodiments, an agent used to identify an agent that modulates MISRH-mediated signal transduction is a small molecule, nucleic acid, nucleic acid analogue, aptamer, ribosome, peptide, protein, antibody, or variants and functional fragments thereof. In some embodiments, an antibody can be, for example but not limited to, a recombinant antibody, humanized antibody, chimeric antibody, modified antibody, monoclonal antibody, polyclonal antibody, miniantibody, dimeric miniantibody, minibody, diabody or tribody or functional variants, functional analogues or functional modified versions thereof. In some embodiments, a nucleic acid is DNA, RNA, nucleic acid analogue, peptide nucleic acid (PNA), pseudo-complementary PNA (pcPNA), locked nucleic acid (LNA) or functional analogues thereof, where an RNA can be, for example but not limited to, a small inhibitory RNA, siRNA, microRNA, shRNA, miRNA and functional analogues and homologues and functional variants thereof.

Prior to administration, the pyrazoloathrone and functional derivatives thereof as disclosed herein can be formulated as a pharmaceutical composition which contains an effective dosage amount of one or more pyrazoloathrone and functional derivatives thereof in combination with one (or more) pharmaceutically acceptable carrier(s). Conditions that may be treated with the pyrazoloathrone and functional derivatives thereof of this invention, or a pharmaceutical composition containing the same and addition of other therapeutic agents, include any condition which may benefit from administration of MIS, and are particularly useful for the prevention and/or treatment of various diseases, for example proliferative diseases, for example cancers expressing MIS receptors, for example cancer expressing MISRII. Examples of such cancers are for example, but not limited to, ovarian cancer, vulvar epidermal carcinoma, cervical carcinoma, endometrial edenocarinaoma and ovarian adenocarcinoma. In alternative embodiments, the cancer expressing MIS receptors, for example cancers expressing MISRII are, for example but not limited to, breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, osteosarcomas, thyroid cancer, prostate cancer, colon cancer, prostate cancer, skin cancer, stomach cancer, testis cancer, tongue cancer, or uterine cancer.

Another aspect of the present invention relates to the use of a pyrazoloanthrone or derivative or analogue thereof for the manufacture of a medicament for treating cancer, wherein the cancer expresses a Mullerian Inhibiting Substance (MIS) receptor. In such embodiments, a pyrazoloanthrone or functional derivative or functional analogue thereof is anthra[1,9-cd]pyrazol-6(2H)-one or a functional derivative or functional analogue thereof. In some embodiments, a cancer cell expresses a MIS type II receptor or a homologue or functional fragment thereof.

Another aspect of the present invention relates to an article of manufacture comprising packaging material and a pharmaceutical composition of claim 48, wherein the packaging material comprises a label which indicates the pharmaceutical composition may be administered, for a sufficient term at an effective dose, for treating or reducing the risk of cancer which expresses a Mullerian Inhibiting Substance (MIS) receptor.

Another aspect of the present invention relates to a method of treating a subject affected with cancer, the method comprising assessing the expression and/or activity of Mullerian Inhibiting Substance Receptor II (MISRII) in a biological sample obtained from the subject, wherein a clinician reviews the results and if the results indicate the presence of expression and/or activity of MISRII, the clinician directs the subject to be treated with pharmaceutical composition as disclosed herein. In some embodiments, a biological sample obtained from the subject is a tissue sample, for example a cancer or tumor tissue sample or a cancer cell or tumor cell, such as a biopsy tissue sample. In some embodiments, the cancer tissue sample comprises an ovarian cancer cell, a vulvar epidermal carcinoma cell, a cervical carcinoma cell, an endometrial edenocarinaoma cell and/or an ovarian adenocarcinoma cell. In some embodiments, the cancer tissue sample is from a cancer, such as, but not limited to, breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, gum cancer, kidney cancer, liver cancer, nasopharynx cancer, ovarian cancer, prostate cancer, skin cancer, stomach cancer, testis cancer, tongue cancer, or uterine cancer.

Another aspect of the present invention relates to the use of a pyrazoloanthrone or derivative or analogue thereof to decrease the plasma serum levels of one or more androgens, such as but not limited to, testosterone, in a subject in need thereof. In some embodiments, the pyrazoloanthrone or derivative or analogue thereof is anthra[1,9-cd]pyrazol-6 (2H)-one or a derivative or analogue thereof.

In some embodiments, the subject in need of the pyrazoloanthrone or derivative or analogue thereof has benign prostic hypertrophy. In alternative embodiments, the subject has prostate cancer, and in some embodiments, the subject has ovarian disease and/or precocious puberty. In alternative embodiments, a subject in need of the pyrazoloanthrone or derivative or analogue thereof can have a disease or disorder selected from the group consisting of; BPH, prostate carcinoma, testicular cancer, androgen dependent acne, male pattern baldness, precocious puberty, hyperandrogenism, hirsutism, virilization, POCS, HIAR-AN syndrome, ovarian hyperthecosis, follicular maturation arrest, atresia, anovulation, dysmenorrheal, dysfunctional uterine bleeding, infertility and androgen-producing tumors.

Another embodiment of the present invention relates to methods to treat a disease or disorder characterized by androgenic dependency, comprising administering to a subject an effective amount of the pharmaceutical composition comprising a pyrazoloanthrone or derivative or analogue as disclosed herein, for example SP600125, wherein the pharmaceutical composition reduces the level of at least one androgen in the plasma serum of the subject and results in a decrease in at least one symptom of a disease or disorder characterized by androgenic dependency.

Another embodiment of the present invention relates to methods to decrease the plasma level of one or more androgens in a subject, the method comprising administering an effective amount of a pyrazoloanthrone or derivative or analogue as disclosed herein, for example but not limited to, SP600125, wherein the pyrazoloanthrone or derivative or analogue thereof decreases the plasma serum levels of one or more androgens in the subject. In some embodiments, the pyrazoloanthrone or derivative or analogue thereof is anthra [1,9-cd]pyrazol-6(2H)-one or a derivative or analogue thereof as disclosed herein. In some embodiments, the subject has a disease or disorder characterized by androgenic dependency, for example but no limited to BPH, prostate carcinoma, benign prostic hypertrophy, testicular cancer, androgen dependent acne, male pattern baldness, precocious puberty, hyperandrogenism, hirsutism, virilization, POCS, HIAR-AN syndrome, ovarian hyperthecosis, follicular maturation arrest, atresia, anovulation, dysmenorrheal, dysfunctional uterine bleeding, infertility and androgen-producing tumors.

These and other aspects of this invention will be apparent upon reference to the following detailed description. To that end, certain patent and other documents are cited herein to more specifically set forth various aspects of this invention. Each of these documents are hereby incorporated by reference in their entirety.

BRIEF DESCRIPTION OF FIGURES

FIG. 2A shows COS7 cells were treated with MIS in combination with increasing doses of SP600125 or JNK inhibitor III and BRE-Luciferase response was measured after 24 h treatment. The results represent the mean values from three independent experiments performed in triplicates (Error bars represent SEM).*P<0.05, P<0.01. FIG. 2B shows transiently transfected COS7 cells that were treated with increasing doses of JNK Inhibitor VIII with or without MIS. The results represent the mean values from three different independent experiments. FIG. 2C shows COS7 cells transiently transfected with MISRII, BRE-Luciferase and phRLCMV were treated with 0.5 µg/ml and/or 10 µM SP600125 for 1, 6, 24 and 48 h. Luciferase activity was measured and normalized to phRL-CMV activity. The results show the relative light units (RLU) and represent the mean values from three independent experiments. a, p<0.05 MIS+SP600125 vs. DMSO, b, p<0.05 MIS and SP600125 vs. DMSO, p<0.01 MIS+SP600125 vs. MIS alone, c, p<0.05 MIS vs. DMSO, P<0.01 MIS+SP600125 vs. MIS. FIG. 2D shows COS7 cells that were transfected with either MIS or BMP type II receptor together with BRE-Luciferase reporter and treated with the respective ligand with or without MIS for 24 h. Results shown represent the mean values form three independent experiments. FIG. 2E shows MOVCAR7 cells transfected with the BRE-luciferase and phRL-CMV were treated for 24 h after which the cells were lysed and luciferase activity was measured and normalized to phRL-CMV. The figure shows the fold induction of BRE over untreated cells. The results shown are the mean values from three independent experiments. (Error bars represent SEM, *p<0.001).

FIG. 3A shows MOVCAR7 cells treated with either 5 µg/ml MIS or 500 nM Anisomycin for 30 min before harvesting and subjecting the lysates to immunoblots recognizing the phosphorylated forms of JNK. FIG. 3B shows phosphorylation of c-jun induced by 500 nM Anisomycin. Cells were pre-treated with the indicated doses of SP600125 induced activation of ph-c-jun was inhibited by 25 µM SP600125 or JNK inhibitor VIII (25 µM). The results are representative of several experiments.

FIG. 4A shows the effect of SP600125 on cell proliferation and survival by comparing cell-lines expressing MISRII (MOVCAR7 cells), and COS7 cells that do not express MISRII. FIG. 4B shows increasing doses of a known ovarian cancer drug, paclitaxel (PTX), was used in combination with SP600125. FIG. 4C shows the effect of 2 µM SP600125, 10 µg/MIS, and 3 nM paclitaxel alone or in combination on another MIS-responsive mouse ovarian cancer cell line, 4306. The results shown are the mean values from three independent experiments. (Error bars represent SEM, *p<0.001). Significant differences at SP600125 concentrations between each treatment group (in FIG. 4B) were determined by two-way factorial ANOVA, *, P<0.001. Significant differences (P<0.05) in FIG. 4C were determined by one-way factorial ANOVA. If any give pair of bars shares the same letter, it is not significantly different.

DETAILED DESCRIPTION

Figure 1:
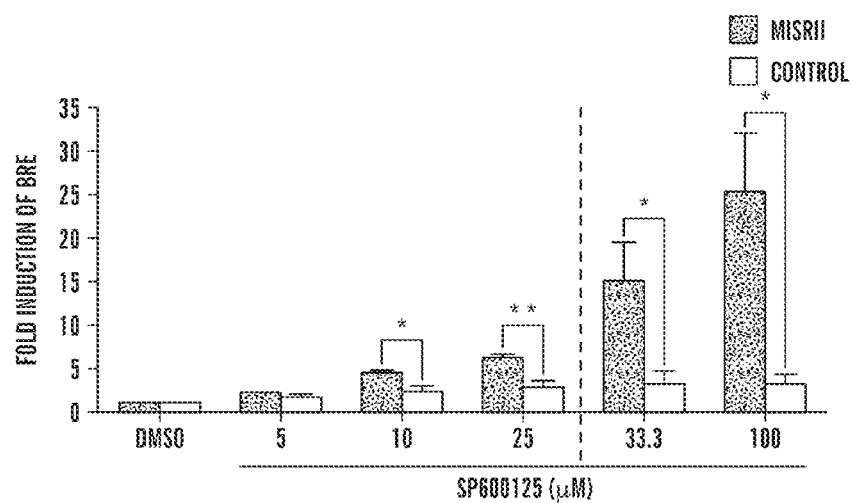
FIG. 1 shows SP600125 induces MISRII dependent BRE-luciferase reporter expression in COS7 cells and increases the MIS response in these cells. COS7 cells were transiently transfected with MISRH, BRE-Luciferase and phRL-CMV. The cells were treated with increasing doses of SP600125 for 24 h. Control cells were transfected with a control plasmid (EGFP-N1 plasmid) instead of the receptor plasmid to keep the total DNA transfected constant. The results shown are the fold-induction over vehicle treated cells and normalized to phRL-CMV expression to correct for variations in cell number and transfection efficiency. Bars shown to the right of the dashed line indicate that the expression of Renilla luciferase was lower, demonstrating that toxic effects to the cells. The results represent the mean values from three independent experiments performed in triplicates (Error bars represent SEM, *p<0.05, **p<0.001).

As discussed herein, the present invention provides a method for treating a variety of conditions by administering an effective amount of a pyrazoloathrone and functional derivatives thereof of the invention to a subject in need thereof. Conditions that may be treated by the compounds of this invention, or a pharmaceutical composition containing the same, include any condition which is treated or reduces the symptoms by administration of MIS or activation of MIS signaling or activation of MISRII, and thereby benefit from administration of a pyrazoloathrone and functional derivatives thereof. Representative conditions in this regard include, for example, but not limited to, cancers that express MIS receptors, for example cancer that express MISRII, for example, but not limited to ovarian, cervical and endometrial cancer. Other conditions which can be treated with MIS or activation of MIS signalling reduces the symptoms are, for example, rheumatoid arthritis, proliferative diseases such as cancer, treatment of prostatic cancer, polycysic ovarian disease, benign prostatic hypertrophy and precocious puberty and other hyperandrogen disorders such as testitoxicosis.

DEFINITIONS

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "Mullerian Inhibiting Substance" and "MIS" are used interchangeably herein and is also known as anti-Müllerian hormone or AMH, refer to compounds and materials which are structurally similar to MIS. Examples of such intended substances are for example, salts, functional derivatives and aglycone forms of MIS. Additionally, the present invention is intended to include mutant forms of MIS which have substantially the same biological activity as MIS. Examples of such mutant MIS molecules carrying a deletion, insertion, or alteration in amino acid sequence. MIS can be obtained from any mammalian source or from non-mammalian sources through the use of recombinant DNA technology, or from chemical synthesis of the MIS protein. For reference purposes only, the human MIS nucleic acid corresponds to ReSeq No: NM_000479 (SEQ ID NO:2) and GenBank No: KO3474 (SEQ ID NO:3), which are incorporated herein by reference.

The term "Mullerian Inhibiting Substance type II receptor" or "MISRII" are used interchangeably herein refer to the type II receptor for MIS. The term MISRII is intended to encompass all MIS receptors substantially homologous to MISRII and functional derivatives of MISRII. MISRII is also known by the alias as AMHR2, and for reference purposes, the nucleic acid sequence of human MISRII corresponds to NM_020547 (SEQ ID NO:4) and GenBank No: AF172932 (SEQ ID NO:5) which are incorporated herein by reference The term "functional derivative" and "mimetic" are used interchangeably herein, and refers to compounds which possess a biological activity (in particular functional biological activity) that is substantially similar to the biological activity of the entity or molecule for which it's a functional derivative of. The term functional derivative is intended to include the fragments, variants, analogues or chemical derivatives of a molecule. In certain embodiments, functional derivatives and functional analogues of pyrazoloathrones can be assessed for their biological activity using the assay as disclosed herein, where derivatives and analogues which activate MIS RII signalling using the assay as disclosed in the Examples would be considered as functional derivatives or functional analogues of pyrazoloathrone.

The term "analog" as used herein refers to an agent that retains the same, or a substantially similar biological function (i.e., binding to a receptor, such as MIS RII) and/or structure as the molecule or chemical or polypeptide it is an analogue of. Examples of analogs include peptidomimetics (a peptide analog), peptide nucleic acids (a nucleic acid analog), small and large organic or inorganic compounds, as well as derivatives and variants of a polypeptide or nucleic acid herein.

The term "substantially similar", when used to define the biological activity of a derivative or analogue of pyrazoloathrone as compared to the biological activity of the pyrazoloathrone to which it is a derivative or analogue of, means that a particular derivative or analogue differs from the initial pyrazoloathrone in chemical structure, by one or more groups or elements, including substitutions, deletions, or additions of groups of elements, the net effect of which is to retain at least some of the biological activity found in the initial pyrazoloathrone with respect to the biological activity of pyrazoloathrone with respect to activation of the MISRII signalling pathyway. Such biological activity can be assessed by one of ordinary skill in the art using the assay as disclosed herein. As such, derivative or analogue of pyrazoloathrones having lesser degrees of structural similarity but a substantially similar or comparable biological activity of the original pyrazoloathrone from which is based with respect to activation of MISRII signalling are considered to be equivalents. Substantially similar derivatives or analogues of pyrazoloathrone will typically have at least about 60%, or at least about 70% or at least about 80% or at least about 90% or at least about 95%, or at least about 100% the biological activity of MISRII activation as compared to the pyrazoloathrone it is a derivative or analogue of, or at least at least 2-fold, or at least about 3-fold, or at least about a 4-fold, or at least about a 5-fold or at least about a 10-fold, or any increase between 2-fold and 10-fold or greater the biological activity of MISRII activation as compared to the pyrazoloathrone are to be considered a functional derivative or a functional analogue of the pyrazoloathrone they are based on, as can be assayed using the methods as disclosed herein.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the term "subject" refers to any living organism which can be administered to the pharmaceutical compositions of the present invention and in which cancer or a proliferative disorder can occur. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, as well as fetuses, whether male or female, are intended to be covered. The term "subject" is also intended to include living organisms susceptible to conditions or disease states as generally disclosed, but not limited to, throughout this specification. Examples of subjects include humans, dogs, cats; cows, goats, and mice. The term subject is further intended to include transgenic species. As used herein, the terms "subject" and "individual" are used interchangeably and are intended to refer to an animal, for example a human, to whom treatment, including prophylactic treatment, with the pharmaceutical composition according to the present invention, is provided, including, but not limited to humans and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "tissue" is intended to include intact cells, blood, blood preparations such as plasma and serum, bones, joints, muscles, smooth muscles, and organs.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, amlady, disorder, sickness, illness, complaint, inderdisposion, affection.

The term "malignancy" and "cancer" are used interchangeably herein, refers to diseases that are characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

The terms "subject" and "individual" are used interchangeably herein, and refer to an animal, for example a human, to whom treatment, including prophylactic treatment, with a pharmaceutical composition as disclosed herein, is provided. The term "subject" as used herein refers to human and non-human animals. The term "non-human animals" and "non-human mammals" are used interchangeably herein and includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

As used herein, the term "tumor" refers to a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and showing a high degree of anaplasia. Anaplasia is the reversion of cells to an immature or a less differentiated form, and it occurs in most malignant tumors.

The term "therapy resistant cancer" as used herein refers to a cancer present in a subject which is resistant to, or refractory to at least two different anti-cancer agents such as chemotherapy agents, which means, typically a subject has been treated with at least two different anti-cancer agents that did not provide effective treatment as that term is defined herein.

The term 'sensitize' or 'sensitizes' used interchangeably herein, refers to making the cell sensitive, or susceptible to other secondary agents, for example other pro-drugs or other environmental effects such as radiation etc.

The term "cell" used herein refers to any cell, prokaryotic or eukaryotic, including plant, yeast, worm, insect and mammalian. Mammalian cells include, without limitation; primate, human and a cell from any animal of interest, including without limitation; mouse, hamster, rabbit, dog, cat, transgenic animal domestic animals, such as equine, bovine, murine, ovine, canine, feline, etc. The cells may be a wide variety of tissue types without limitation such as; hematopoietic, neural, mesenchymal, cutaneous, mucosal, stromal, muscle spleen, reticuloendothelial, epithelial, endothelial, hepatic, kidney, gastrointestinal, pulmonary, T-cells etc. Stem cells, embryonic stem (ES) cells, ES-derived cells and stem cell progenitors are also included, including without limitation, hematopoeitic, stromal, muscle, cardiovascular, hepatic, pulmonary, gastrointestinal stem cells, etc. Yeast cells may also be used as cells in this invention. Cells also refer not to a particular subject cell but to the progeny or potential progeny of such a cell because of certain modifications or environmental influences, for example differentiation, such that the progeny may not, in fact be identical to the parent cell, but are still included in the scope of the invention.

The cells used in the invention can also be cultured cells, e.g. in vitro or ex vivo. For example, cells cultured in vitro in a culture medium. Alternatively, for ex vivo cultured cells, cells can be obtained from a subject, where the subject is healthy and/or affected with a disease. Cells can be obtained, as a non-limiting example, by biopsy or other surgical means know to those skilled in the art. Cells used in the invention can be present in a subject, e.g. in vivo. For the invention on use on in vivo cells, the cell is preferably found in a subject and display characteristics of the disease, disorder, or malignancy pathology As used herein, the terms "treat" or "treatment" or "treating" refers to both therapeutic treatment and prophylactic or preventative measures, wherein the object is to prevent or slow the development of the disease, such as slow down the development of a tumor, the spread of cancer, or reducing at least one effect or symptom of a condition, disease or disorder associated with inappropriate proliferation or a cell mass, for example cancer. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer, as well as those likely to develop secondary tumors due to metastasis.

The term "effective amount" as used herein refers to the amount of therapeutic agent of pharmaceutical composition, such as the pharmaceutical composition comprising at least one pyrazoloanthrones as disclosed herein, to alleviate at least one or more symptom of the disease or disorder, and relates to a sufficient amount of pharmacological composition to provide the desired effect. The phrase "therapeutically effective amount" as used herein, e.g., a pharmaceutical composition comprising at least one pyrazoloanthrones as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylacticly significant reduction in a symptom or clinical marker associated with a cancer or a cancer-mediated condition.

A therapeutically or prophylatically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

With reference to the treatment of a subject with a cancer with a pharmaceutical composition comprising at least one pyrazoloanthrones as disclosed herein, the term "therapeutically effective amount" refers to the amount that is safe and sufficient to prevent or delay the development and further growth of a tumor or the spread of metastases in cancer patients. The amount can thus cure or cause the cancer to go into remission, slow the course of cancer progression, slow or inhibit tumor growth, slow or inhibit tumor metastasis, slow or inhibit the establishment of secondary tumors at metastatic sites, or inhibit the formation of new tumor metastases. The effective amount for the treatment of cancer depends on the tumor to be treated, the severity of the tumor, the drug resistance level of the tumor, the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of cancer and tumor, for example treatment of a rodent with a cancer, and any treatment or administration of the compositions or formulations that leads to a decrease of at least one symptom of the cancer, for example a reduction in the size of the tumor or a slowing or cessation of the rate of growth of the tumor indicates effective treatment. In embodiments where the compositions are used for the treatment of cancer, the efficacy of the composition can be judged using an experimental animal model of cancer, e.g., wild-type mice or rats, or preferably, transplantation of tumor cells. When using an experimental animal model, efficacy of treatment is evidenced when a reduction in a symptom of the cancer, for example a reduction in the size of the tumor or a slowing or cessation of the rate of growth of the tumor occurs earlier in treated, versus untreated animals. By "earlier" is meant that a decrease, for example in the size of the tumor occurs at least 5% earlier, but preferably more, e.g., one day earlier, two days earlier, 3 days earlier, or more.

As used herein, the term "treating" when used in reference to a cancer treatment is used to refer to the reduction of a symptom and/or a biochemical marker of cancer, for example a reduction in at least one biochemical marker of cancer by at least about 10% would be considered an effective treatment. Examples of such biochemical markers of cancer include CD44, telomerase, TGF-α, TGF-β, erbB-2, erbB-3, MUC1, MUC2, CK20, PSA, CA125 and FOBT. A reduction in the rate of proliferation of the cancer cells by at least about 10% would also be considered effective treatment by the methods as disclosed herein. As alternative examples, a reduction in a symptom of cancer, for example, a slowing of the rate of growth of the cancer by at least about 10% or a cessation of the increase in tumor size, or a reduction in the size of a tumor by at least about 10% or a reduction in the tumor spread (i.e. tumor metastasis) by at least about 10% would also be considered as affective treatments by the methods as disclosed herein. In some embodiments, it is preferred, but not required that the therapeutic agent actually kill the tumor.

As used herein, the terms "administering," and "introducing" are used interchangeably herein and refer to the placement of the pharmaceutical compositions of the present invention comprising the pyrazoloanthrones of the present invention into a subject by a method or route which results in at least partial localization of the pyrazoloanthrones at a desired site. The compounds of the present invention can be administered by any appropriate route which results in an effective treatment in the subject.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. The phrases "systemic administration," "administered systemically", "peripheral administration" and "administered peripherally" as used herein mean the administration of the pharmaceutical compositions of the present invention comprising pyrazoloanthrones and optionally other agents or material other than directly into the central nervous system, such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The terms "composition" or "pharmaceutical composition" used interchangeably herein refer to Compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) *Remington: The Science and Practice of Pharmacy with Facts and Comparisons,* 21st Ed.

The term "agent" or "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, or any organic or inorganic molecule, including modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof. For example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "vectors" used interchangeably with "plasmid" refer to a nucleic acid molecule capable of transporting another nucleic acid to which it has been linked. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors may integrate into the host's genome or replicate autonomously in the particular cell. Other forms of expression vectors known by those skilled in the art which serve the equivalent functions can also be used. Expression vectors comprise expression vectors for stable or transient expression encoding the DNA.

As used herein, a "promoter" or "promoter region" or "promoter element" used interchangeably herein refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, an optional operate sequence to control transcription, a sequence encoding suitable mRNA ribosomal binding sites, and sequences to control the termination of transcription and/or translation. Regulatory sequences are selected for the assay to control the expression of split-biomolecular conjugate in a cell-type in which expression is intended.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

The term "operatively linked" or "operatively associated" are used interchangeably herein, and refer to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined.

The term "oncogene" as used herein refers to a nucleic acid sequence encoding, or polypeptide, of a mutated and/or overexpressed version of a normal gene that in a dominant fashion can release the cell from normal restraints on growth and thus alone or in concert with other changes, contribute to a cells tumorigenicity. Examples of oncogenes include; gp40 (v-fms); p21 (ras); p55 (v-myc); p65 (gag-jun); pp 60 (v-src); v-abl; v-erb; v-erba; v-fos etc. A proto-oncogene refers to the normal expression of a nucleic acid expressing the normal, cellular equivalent of an oncogene, typically these genes are usually a gene involved in the signaling or regulation of cell growth.

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Compositions of Pyrazoloathrone and Derivatives

As mentioned above, the present invention is directed to compounds which have activity as selective inhibitors of JNK, as well as to compositions and methods relating to the same. The

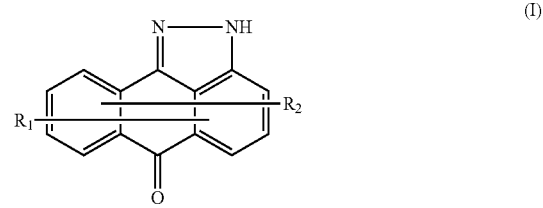

compounds of this invention have the following structure (I), also known herein as Compound (II):
and pharmaceutically acceptable salts thereof, wherein:

$R_1$ and $R_2$ are optional substituents that are the same or different and independently represent alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono- or di-alkylaminoalkoxy, or a group represented by formula (a), (b), (c) or (d):

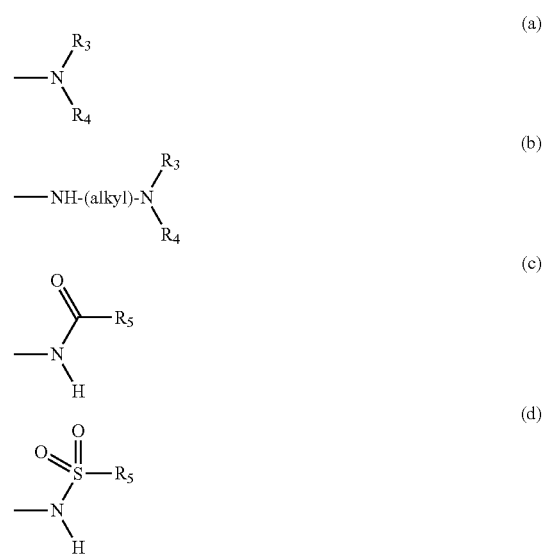

$R_3$ and $R_4$ taken together represent alkylidene or a heteroatom-containing alkylidene, or $R_3$ and $R_4$ are the same or different and independently represent hydrogen, alkyl, cycloalkyl, aryl, arylalkyl, cycloalkylalkyl, aryloxyalkyl, alkoxyalkyl, alkoxyamino, or alkoxy(mono- or di-alkylamino); and $R_5$ represents hydrogen, alkyl, cycloalkyl, aryl, arylalkyl, cycloalkylalkyl, alkoxy, amino, mono- or di-alkylamino, arylamino, arylalkylamino, cycloalkylamino, or cycloalkylalkylamino.

As used herein, the terms used above having following meaning.

"Alkyl" means a straight chain or branched, saturated or unsaturated alkyl chain having from 1 to 8 carbon atoms, such as methyl, ethyl, n-propyl, iso-propyl, n-butyl, iso-butyl, tert-butyl, propylenyl, 1-butenyl, propynyl, and the like.

"Halogen" means fluorine, chlorine, bromine or iodine.

"Trifluoromethyl" means —$CF_3$.

"Sulfonyl" means —$SO_3H$.

"Carboxyl" means —COOH.

"Alkoxy" means —O-(alkyl), such as methoxy, ethoxy, n-propyloxy, iso-propyloxy, n-butyloxy, iso-butyloxy, and the like.

"Alkoxyalkoxy" means —O-(alkyl)-O-(alkyl), such as —$OCH_2CH_2OCH_3$, and the like.

"Alkoxycarbonyl" means —C(IO)O-(alkyl), such as —C(=O)$OCH_3$, —C(=O)$OCH_2CH_3$, and the like.

"Alkoxyalkyl" means -(alkyl)-O-(alkyl), such as —$CH_2OCH_3$, —$CH_2OCH_2CH_3$, and the like.

"Aryl" means a carbocyclic or heterocyclic aromatic group containing from 5 to 10 ring atoms. The ring atoms of a carbocyclic aryl group are all carbon atoms, and includes phenyl and naphthyl. The ring atoms of a heterocyclic aryl group contains at least one heteroatom selected from nitrogen, oxygen and sulfur, and include pyridinyl, pyrimidinyl, furanyl, thienyl, imidazolyl, thiazolyl, pyrazolyl, pyridazinyl, pyrazinyl, triazinyl, tetrazolyl, and indolyl.

"Aryloxy" means —O-(aryl), such as —O-phenyl, —O-pyridinyl, and the like.

"Arylalkyl" means -(alkyl)-(aryl), such as benzyl (i.e., —$CH_2$-phenyl), —$CH_2$-pyrindinyl, and the like.

"Arylalkyloxy" means —O-(alkyl)-(aryl), such as —O-benzyl, —O—$CH_2$-pyridinyl, and the like.

"Cycloalkyl" means a cyclic alkyl having from 3 to 7 carbon atoms, such as cyclopropyl, cyclopentyl, cyclohexyl, and the like.

"Cycloalkyloxy" means —O-(cycloalkyl), such as —O-cyclohexyl, and the like.

"Cycloalkylalkyloxy" means —O-(alkyl)-(cycloalkyl, such as —$OCH_2$cyclohexyl, and the like.

"Alkylidene" means the divalent radical —$C_nH_{2n}$—, wherein n is an integer from 1 to 8, such as —$CH_2$—, —$CH_2CH_2$—, —$CH_2$—$CH_2$—$CH_2$—, —$CH_2CH_2CH_2CH_2$—, —$CH_2CH_2CH_2CH_2CH_2$—, and the like.

"Heteroatom-containing alkylidene" means an alkylidene wherein at least one carbon atom is replaced by a heteroatom selected from nitrogen, oxygen or sulfur, such as —$CH_2CH_2OCH_2CH_2$—, and the like.

"Aminoalkoxy" means —O-(alkyl)-$NH_2$, such as —$OCH_2NH_2$, —$OCH_2CH_2NH_2$, and the like.

"Mono- or di-alkylamino" means —NH(alkyl) or —N(alkyl)(alkyl), respectively, such as —$NHCH_3$, —$N(CH_3)_2$, and the like.

"Mono- or di-alkylaminoalkoxy" means —O-(alkyl)-NH(alkyl) or —O-(alkyl)-N(alkyl)(alkyl), respectively, such as —$OCH_2NHCH_3$, —$OCH_2CH_2N(CH_3)_2$, and the like.

"Arylamino" means —NH(aryl), such as —NH-phenyl, —NH-pyridinyl, and the like.

"Arylalkylamino" means —NH-(alkyl)-(aryl), such as —NH-benzyl, —$NHCH_2$-pyridinyl, and the like.

"Alkylamino" means —NH(alkyl), such as —$NHCH_3$, —$NHCH_2CH_3$, and the like.

"Cycloalkylamino" means —NH-(cycloalkyl), such as —NH-cyclohexyl, and the like.

"Cycloalkylalkylamino" —NH-(alkyl)-(cycloalkyl), such as —$NHCH_2$-cyclohexyl, and the like.

In the embodiment wherein $R_1$ and $R_2$ are not present, compounds of this invention have the following structure (II) (also referred to herein as "Compound (I)"):

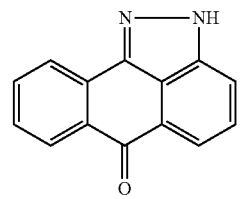

(II)

This compound is commercially available from Pfaltz-Bauer (Conn., U.S.) and also StressGen Bioreagents, (MI, U.S), also referred to as SP600125 and/or anthra[1,9-cd]pyrazol-6(2H)-one.

In the embodiment wherein only one of $R_1$ and $R_2$ is present, compounds of this invention

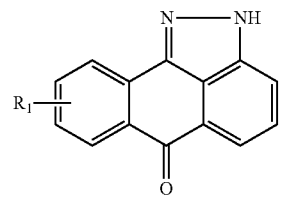

(III)

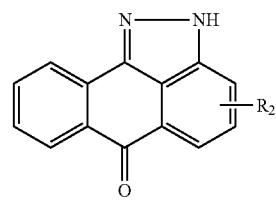

(IV)

In the embodiment wherein both $R_1$ and $R_2$ are present, compounds of this invention have one of the following structures (V), (VI) or (VII):

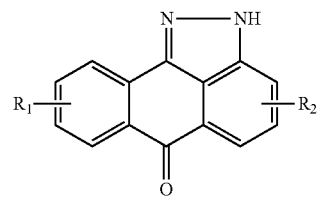

(V)

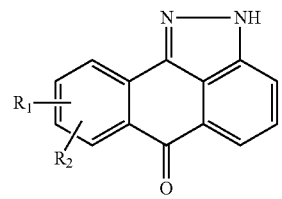

(VI)

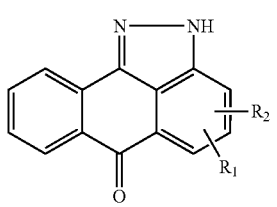

(VII)

The compound Andra[1,9cd]pyrazol-6(2H)-one ("Compound I" or "SP600125") is a yellow solid and is synthesized by the addition of anhydrous hydrazine to a solution of 2-chloroanthraquinone (Aldrich) in 10 ml pyridine, and the mixture heated at 100° C. for 16 hours. The mixture is cooled and the solvent is evaporated in vacuo. The residue is taken in hot 6N HCl, and the solid is collected by filtration. Flash chromatography of the crude material on silica gel affords anthra[1,9cd]pyrazol-6(2H)-one ("Compound I") as yellow solids. For example, the reaction scheme is:

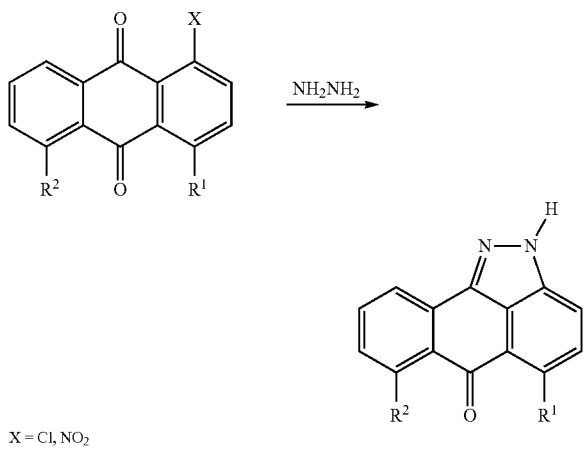

X = Cl, NO₂

The above reaction yields Anthra[1,9cd]pyrazol-6(2H)-one ("Compound (I)" or "SP600125"):

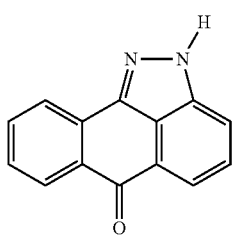 [SMILES: O=C1c2ccccc2-c2n[nH]c3cccc1c23]

Purification of Anthra[1,9cd]pyrazol-6(2H)-one ("Compound (I)" or "SP600125") can be performed as previously described in the methods disclosed in U.S. Pat. No. 7,119,114, which is incorporated herein in its entirety by reference.

Pharmaceutically acceptable salts of compounds of structure (I) or structure (II) are also within the scope of this invention. To this end, the compound may generally be utilized as the free base. Alternatively, the compounds may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of a compound of structure (I) is intended to encompass any and all acceptable salt forms.

The compounds of the present invention may generally be made by organic synthesis techniques known to those skilled in the art, as well as by the methods disclosed in U.S. Pat. No. 7,119,114, which is incorporated herein in its entirety by reference.

Method of Treatment of a Subject

The present invention relates generally to a method of treating a proliferative disease or disorder in a subject, where the proliferative disease or disorder is associated with cells that express a MIS receptor, for example cells expressing MISRII. In some embodiments, the proliferative disease or disorder is cancer, where the cancer or cancer cells express at least one MIS receptor, for example cancer or cancer cells expressing MISRII. The method of the present invention comprises the administration of an effective amount of Compound I of the invention or analogue or derivative thereof to a subject in with a proliferative disorder, where the cells associated with the proliferative disorder express at least one MIS receptors, for example the cells express MISRII. For example, an effective amount of Compound I of the invention or analogue or derivative thereof is administered to a subject with a cancer expressing at least one MIS receptors, for example expressing MISRII. Thus, by using the methods of the present invention, one can intervene in the proliferative disease, for example cancer, ameliorate the symptoms, and in some cases cure the disease.

Examples of such diseases where proliferation of cells expressing at least one MIS receptors, for example expressing MISRII is the cause of disease are cancers, for example cervical cancer and ovarian cancer. In some embodiments, the cancer expressing at least one MIS receptor, for example MISRII is a cancer cell. In some embodiments, such a cancer cell expressing at least one MIS receptors, for example expressing MISRII is, for example but not limited to, an ovarian cancer cell, vulvar epidermal carcinoma cell, cervical carcinoma cell, endometrial edenocarinaoma cell, ovarian adenocarcinoma.

In alternative embodiments, the cancer expressing at least one MIS receptor, for example cancers expressing MISRII are for example but not limited to; breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, osteosarcomas, thyroid cancer, prostate cancer, colon cancer, prostate cancer, skin cancer, stomach cancer, testis cancer, tongue cancer, or uterine cancer.

In alternative embodiments, the present invention relates to the use of pyrazoloathrone and functional derivatives thereof for the treatment of any disorder where administration of the MIS protein or a nucleic acid encoding MIS protein or activation MISRII is whole or part of the therapeutic regime.

In some embodiments, the cancer is a MIS-responsive cancer, for example but not limited ovarian cancer and cervical cancer. In some embodiments, the cancer expresses MISRII, for example but not limited ovarian cancer and cervical cancer. In some embodiments, the disorder is a disorder associated with excess androgen states, for example as disclosed in U.S. Pat. No. 6,673,352, which is incorporated in its entirety herein by reference. In some embodiments, the methods of the present invention are used in the treatment of prostatic cancer, polycysic ovarian disease, benign prostatic hypertrophy and precocious puberty.

In a related embodiment, a tissue to be treated is a tumor tissue expressing at least one MIS receptor, for example expressing MISRII of a subject, for example the tumor tissue is, but not limited to a solid tumor, a metastases, a skin cancer, a breast cancer, an ovarian cancer, an cervical cancer, a hemangioma or angiofibroma and the like cancer. Typical solid tumor tissues treatable by the pharmaceutical composition of the invention, includes for example, but not limited to tumors of the lung, pancreas, breast, colon, laryngeal, ovarian, and the like tissues. In some embodiment, the solid tumor tissue treatable by the present methods include thyroid, and the cancer type is medullary thyroid cancer.

In a related embodiment, the invention contemplates the practice of the method in conjunction with other therapies such as conventional chemotherapy directed against solid tumors and for control of establishment of metastases. The administration of the compounds described herein is typically conducted prior to and/or at the same time and/or after chemotherapy, although it is also encompassed within the present invention to inhibit cell proliferation after a regimen of chemotherapy at times where the tumor tissue will be responding to the toxic assault by inducing angiogenesis to recover by the provision of a blood supply and nutrients to the tumor tissue. In addition, the pharmaceutical compositions of the invention for the treatment of proliferative disorders, for example cancer, can be administrated prophylatically and/or before the development of a tumor, if the subject has been identified as to have a risk of developing cancer, for example to subjects that are positive for biomarkers of cancer cells or tumors. Insofar as the present methods apply to inhibition of cell proliferation, the methods can also apply to inhibition of tumor tissue growth, to inhibition of tumor metastases formation, and to regression of established tumors.

The presence of MISRII in fluids such as blood may be indicative of the presence of cancer. The presence of MISRII in fluids or sites not near a tumor may be indicative of metastasis. In some such embodiments, the compounds of the present invention are administered to the subject, and in some embodiments the compounds of the present invention are administered to the subject in a pharmaceutical composition comprising one or more additional therapies.

The inventive methods disclosed herein provide for the parenteral and oral administration of the compounds of the present invention, in combination with other pharmaceutical compositions to subjects in need of such treatment. Parenteral administration includes, but is not limited to, intravenous (IV), intramuscular (IM), subcutaneous (SC), intraperitoneal (IP), intranasal, and inhalant routes. In the method of the present invention, the resolvins and/or protectins or analogs thereof are preferably administered orally. IV, IM, SC, and IP administration may be by bolus or infusion, and may also be by slow release implantable device, including, but not limited to pumps, slow release formulations, and mechanical devices. The formulation, route and method of administration, and dosage will depend on the disorder to be treated and the medical history of the subject. In general, a dose that is administered by subcutaneous injection will be greater than the therapeutically-equivalent dose given intravenously or intramuscularly. Preferably, the dose of compounds of the present invention will be administered at doses from about 0.1 mg to about 250 mg of body weight. In some embodiments, the dose of compounds of the present invention will be from about 1 mg to about 60 mg.

The methods of the present invention for treating cancer expressing at least one MIS receptor, for example expressing MISRII are useful for treatment of proliferation-related diseases or cancer, which is associated with cells expressing at least one MIS receptor, for example MISRII, comprising contacting a tissue in which proliferation is occurring, or is at risk for occurring, with the compositions of the present invention comprising a therapeutically effective amount of Compound (I) and/or Compound (II) or functional derivatives thereof.

In some embodiments, the subject treated by the methods of the present invention in its many embodiments is a human subject, although it is to be understood that the principles of the invention indicate that the invention is effective with respect to all mammals. In this context, a mammal is understood to include any mammalian species in which treatment of diseases associated with cancer or a proliferative-related disorder is desirable, particularly agricultural and domestic mammalian species, as well as transgenic animals.

Administration of Pharmaceutical compositions

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

After formulation with an appropriate pharmaceutically acceptable carrier in a desired dosage, the pharmaceutical compositions of this invention can be administered to a subject. The pharmaceutical compositions of this invention can be administered to a subject using any suitable means. In general, suitable means of administration include, but are not limited to, topical, oral, parenteral (e.g., intravenous, subcutaneous or intramuscular), rectal, intracisternal, intravaginal, intraperitoneal, ocular, or nasal routes.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

When the compounds of the present invention, for example Compound (I) and/or Compound (II) are administered as pharmaceuticals, to humans and mammals, they can be given per se or as a pharmaceutical composition containing, for example, 0.1 to 99.5% (more preferably, 0.5 to 90%) of active ingredient, i.e., at least one Compound I and/or Compound (II) and/or derivative thereof, in combination with a pharmaceutically acceptable carrier.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects; will range from about 0.1 mg to about 250 mg per kilogram of body weight per day, more preferably from about 1 mg to about 60 mg per kg per day.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the present invention, or functional derivatives thereof. An "effective amount" is the amount as defined herein in the definition section and refers to an amount effective, at dosages and for periods of time necessary, to achieve the desired therapeutic result, e.g., a diminishment or prevention of effects associated with proliferative disease states or conditions, such as cancer, wherein the cancer expresses a MIS receptor. A therapeutically effective amount of the pyrazoloanthrone compounds of the present invention or functional derivatives thereof may vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylatically or therapeutically effective amount is also one in which any toxic or detrimental effects of the compound are outweighed by the beneficial effects.

The term "synergy" or "synergistic" as used herein, refers to the interaction of two or more agents so that their combined effect is greater than each of their individual effects at the same dose alone.

Dosage regimens may be adjusted to provide the optimum desired response (e.g. a therapeutic or prophylactic response). For example, a single bolus may be administered, several divided doses may be administered over time or the dose may be proportionally reduced or increased as indicated by the exigency of the therapeutic situation. It is especially advantageous to formulate parenteral compositions in dosage unit form for ease of administration and uniformity of dosage. Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the patient.

The term "dosage unit" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound, for example Compound (I) and/or Compound (II) and/or derivative thereof and the particular therapeutic or prophylactic effect to be achieved, and (b) the limitations inherent in the art of compounding such an active compound for the treatment of sensitivity in individuals.

In some embodiments, therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is sufficient to reduce or inhibit cell proliferation in a subject suffering from a proliferative disorder, for example cancer. In some embodiments, the therapeutically effective amount is sufficient to eliminate the proliferative cells, for example eliminate the cancer cells and/or tumor in a subject suffering cancer and/or a proliferative disease.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of Compound (I) and/or Compound (II) or functional derivatives thereof, and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more of Compound (I) and/or Compound (II) or functional derivatives thereof are optionally tested in one or more appropriate in vitro and/or in vivo animal models of disease, such as models of cancer, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of Compound (I) and/or Compound (H) or functional derivatives thereof at various concentrations, e.g., as applied to the mass and overall health of the patient. Administration can be accomplished via single or divided doses.

In vitro models can be used to determine the effective doses of Compound (I) and/or Compound (II) or functional derivatives thereof as a potential cancer treatment. Suitable in vitro models include, but are not limited to, proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., I J. Natl. Can. Inst., 52: 921-30 (1974), mobility and invasive potential of tumor cells in Boyden Chamber assays as described in Pilkington et al., Anticancer Res., 17: 4107-9 (1997), and angiogenesis assays such as induction of vascularization of the chick chorioallantoic membrane or induction of vascular endothelial cell migration as described in Ribatta et al., Intl. J. Dev. Biol., 40: 1189-97

(1999) and Li et al., Clin. Exp. Metastasis, 17:423-9 (1999), respectively. Suitable tumor cells lines are available, e.g. from American Type Tissue Culture Collection catalogs.

In vivo models are the preferred models to determine the effective doses of Compound (I) and/or Compound (II) or functional derivatives thereof as disclosed herein as potential cancer treatments. Suitable in vivo models include, but are not limited to, mice that carry a mutation in the KRAS oncogene (Lox-Stop-Lox K-RasGi2D mutants, Kras24TYj) available from the National Cancer Institute (NCI) Frederick Mouse Repository. Other mouse models known in the art and that are available include but are not limited to models for breast cancer, gastrointestinal cancer, hematopoietic cancer, lung cancer, mammary gland cancer, nervous system cancer, ovarian cancer, prostate cancer, skin cancer, cervical cancer, oral cancer, and sarcoma cancer (see http://emice.nci.nih.gov/mouse_models/).

In determining the effective amount of Compound (I) and/or Compound (II) or functional derivatives thereof to be administered in the treatment or prophylaxis of disease the physician evaluates circulating plasma levels, formulation toxicities, and progression of the disease.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. In some embodiments, the compounds of the present invention have an $ED_{50}$ value ranging from 0.01-10 µM in an assay for JNK. The compound (I) as a $IC_{50}$ of about 0.11 µM for JNK1 and JNK2, and about 0.15 µM for JNK3 according to the assay as disclosed in U.S. patent application Ser. No. 7,119,114, which is incorporated herein in its entirety by reference.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

An exemplary, non-limiting range for a therapeutically or prophylactically effective amount of the compounds of the present invention, for example Compound (I) and/or Compound (II) and/or functional derivatives thereof of the invention is 0.1-250 mg/kg, and in some embodiments, the dosage is 1-60 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The invention features an article of manufacture that contains packaging material and compounds of the present invention, for example Compound (I) and/or Compound (II) and/or functional derivatives thereof in a formulation contained within the packaging material. This formulation contains an at least one of the compounds of the present invention, for example Compound (I) and/or Compound (II) and/or functional derivatives thereof and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable compounds of the present invention, for example Compound (I) and/or Compound (II) and/or functional derivatives thereof are described herein.

More specifically, the invention features an article of manufacture that contains packaging material and at least one of the compounds of the present invention, for example Compound (I) or functional derivatives thereof contained within the packaging material. The packaging material contains a label or package insert indicating that the formulation can be administered to the subject to alleviate a proliferative disorder, for example cancer in an amount, at a frequency, and for a duration effective treat or prevent symptoms associated with such disease states or conditions discussed throughout this specification.

Pharmaceutical Compositions

In another embodiment of the invention, pharmaceutical compositions containing one or more compounds of this invention are disclosed. For purpose of administration, a compound of structure (I) and/or structure (II) is preferably formulated as a pharmaceutical composition. Pharmaceutical compositions of the present invention comprise a compound of this invention and a pharmaceutically acceptable carrier, wherein the compound is present in the composition in an amount which is effective to treat the condition of interest. Preferably, the pharmaceutical compositions of the present invention include a compound of structure (I) and/or structure (H) in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in *Remington's Pharmaceutical Sciences*, Gennaro, Ed., Mack Publishing Co., Easton, Pa. 1990.

While it is possible for compounds of the present invention, for example Compound (I) and/or Compound (H) and/or functional derivatives thereof, to be administered alone, it is preferable to administer the compound as a pharmaceutical composition.

Formulations of the invention can be prepared by a number or means known to persons skilled in the art. In some embodiments the formulations can be prepared by combining (i) at least Compound (I) and/or and/or Compound (II) and/or functional derivatives thereof in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

The compositions of the present invention can be in any form. These forms include, but are not limited to, solutions, suspensions, dispersions, ointments (including oral ointments), creams, pastes, gels, powders (including tooth powders), toothpastes, lozenges, salve, chewing gum, mouth sprays, pastilles, sachets, mouthwashes, aerosols, tablets, capsules, transdermal patches, that comprise one or more of the compounds of the present invention, and/or their functional derivatives thereof for oral or subcutaneous administration.

In certain embodiments, the compounds of the present invention, for example Compound (I) and functional derivatives thereof are administered to a subject as a pharmaceutical composition with a pharmaceutically acceptable carrier. In certain embodiments, these pharmaceutical compositions optionally further comprise one or more additional therapeutic agents. In certain embodiments, the additional therapeutic agent or agents are anti-cancer agents. In some embodiments, the therapeutic agents are chemotherapeutic agents, for example but not limited to, cisplatin, paxicital etc. In some embodiments, the therapeutic agents are radiotherapeutic agents. Examples of chemotherapeutic agents in the pharmaceutical compositions of this invention are, for example nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon, platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective and encompassed for use in the methods of the present invention. Of course, other chemotherapeutic agents which are known to those of ordinary skill in the art can readily be substituted as this list should not be considered exhaustive or limiting.

In some embodiments the pharmaceutical composition comprises compounds of the present invention, for example Compound (I) and/or Compound (II) and/or functional derivatives thereof, alone or in any plurality of combinations. In other embodiments, the pharmaceutical compositions optionally further comprise one or more additional therapeutic agents including but not limited to paxicital, functional derivatives of paxicital, cisplatin and functional derivatives of cisplatin, and interferons.

In some embodiments, the pharmaceutical composition comprising Compound (I) and/or Compound (II) or derivatives thereof as disclosed herein can supplement the treatment of any known additional therapy, including, but not limited to, antibody administration, vaccine administration, administration of cytotoxic agents, natural amino acid polypeptides, nucleic acids, nucleotide analogues, and biologic response modifiers. In some embodiments, additional therapy is, for example, surgery, chemotherapy, radiotherapy, thermotherapy, immunotherapy, hormone therapy and laser therapy. In some embodiments, the additional therapy is chemotherapy. Two or more combined compounds may be used together or sequentially with the pharmaceutical composition comprising Compound (I) and/or Compound (II) or derivatives thereof. In some embodiments, Compound (I) and/or Compound (II) or derivatives thereof can be administered before the additional therapy, after the additional therapy or at the same time as the additional therapy. In some embodiments, the Compound (I) and/or Compound (II) or functional derivatives thereof are administered a plurality of times, and in other embodiments, the additional therapies are also administered a plurality of times.

In some embodiments, Compound (I) and/or Compound (II) or functional derivatives thereof can also be administered in therapeutically effective amounts as a portion of an anti-cancer cocktail. An anti-cancer cocktail is a mixture, for example at least one of compound (I) and/or Compound (II) or functional derivatives thereof is combined with one or more additional anti-cancer agents in addition to a pharmaceutically acceptable carrier for delivery. The use of anti-cancer cocktails as a cancer treatment is routine. Anti-cancer agents that are well known in the art and can be used as a treatment in combination with Compound (I) and/or Compound (II) or functional derivatives thereof as disclosed herein include, but are not limited to: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Flosuridine, S-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Ockeotide, Paclitaxel; Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate, and analogues thereof.

In certain embodiments, the pharmaceutical compositions comprising compound (I) and/or compound (II) or functional derivatives thereof can optionally further comprise one or more additional therapies or agents. In certain embodiments, the additional agent or agents are anti-cancer agents. In some embodiments, the therapeutic agents are chemotherapeutic agents, for example cisplatin, paxicital etc. In some embodiments, the therapeutic agents are radiotherapeutic agents. Examples of chemotherapeutic agents in the pharmaceutical compositions of this invention are, for example nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon, platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective. Of course, other chemotherapeutic agents which are known to those of ordinary skill in the art can readily be substituted as this list should not be considered exhaustive or limiting.

In some embodiments, compound (I) and/or Compound (II) or functional derivatives thereof is administered to a subject with other anti-cancer therapies, for example cancer therapies to which the cancer was previously resistant or refractory.

In some embodiments, the methods of the present invention are directed to use of pyrazoloathrone and functional derivatives thereof with other therapeutic agents, for example chemotherapy agents, wherein the chemotherapy agents, for example paclitaxel or MIS can be used at a lower dose that results in decreased side effects.

In some embodiments, the chemotherapeutic agent is MIS, for example recombinant human MIS (rhMIS). In such embodiments, MIS or rhMIS can be prepared and administered, in any form, by any method known by persons of ordinary skill in the art, for example as disclosed in International Patent Application WO92/18152 and European Patent EP584287 and also disclosed in patent Applications WO94/00133 and EP221761, which are incorporated herein in their entity by reference.

In certain embodiments, the endogenous compounds are isolated and/or purified or substantially purified by one or more purification methods described herein or known by those skilled in the art. Generally, the purities are at least 90%, in particular 95% and often greater than 99%. In certain embodiments, the naturally occurring compound is excluded from the general description of the broader genus.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. The term "pharmaceutically acceptable carriers" is intended to include all solvents, diluents, or other liquid vehicle, dispersion or suspension aids, surface active agents, isotonic agents, thickening or emulsifying agents, preservatives, solid binders, lubricants and the like, as suited to the particular dosage form desired. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its functional derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention.

These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use. These compounds include the zwitterionic forms, where possible, of compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "prodrug" refers to compounds that are rapidly transformed in vivo to yield the compounds of the invention, for example the pyrazoloathrone and functional derivatives thereof of the invention, by hydrolysis in blood. A thorough discussion is provided in T. Higachi and V. Stella, "Pro-drugs as Novel Delivery Systems," Vol. 14 of the A.C.S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. The prodrug may be designed to alter the metabolic stability or the transport characteristics of a compound, to mask side effects or toxicity, to improve the flavor of a compound or to alter other characteristics or properties of a compound. By virtue of knowledge of pharmacodynamic processes and drug metabolism in vivo, once a pharmaceutically active compound is identified, those of skill in the pharmaceutical art generally can design prodrugs of the compound (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

In other embodiments of the present invention, the pyrazoloathrone and functional derivatives thereof are conjugated or covalently attached to another targeting agent to increase the specificity of a pyrazoloathrone and functional derivatives thereof targeting the cell, for example a cancer cell. Targeting agents can include, for example without limitation, antibodies, cytokines and receptor ligands. In some embodiments, the targeting agent is overexpressed on the cells to be targeted, for example the cancer cells as compared to normal cells. In alternative embodiments, the pyrazoloathrone and functional derivatives thereof can be conjugated or covalently attached to compounds that elicit an immune response, such as for example but without limitation, cytokines.

In some embodiments, the pyrazoloathrone and functional derivatives thereof of the present invention can be conjugated to, by covalent linkage or any other means, to another agent, for example a chemotherapy agent, or MIS or functional derivatives and analogues thereof. In some embodiments, the pyrazoloathrone and functional derivatives thereof of the present invention can be conjugated to a targeting moiety, for example a cancer cell targeting moiety to target the compounds of the present invention to a cancer cell. Such targeting moieties and methods are well known by persons of ordinary skill in the art and are encompassed for use in the methods of the present invention. The conjugation may be a permanent or reversible conjugation.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. In one aspect, a solution of resolvin and/or protectin or precursor or analog thereof can be administered as eye drops for ocular neovascularization or ear drops to treat otitis.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some instances, pharmaceutical compositions comprising the resolvins and protectins of the invention for the administration of angiogenesis may be in a formulation suitable for rectal or vaginal administration, for example as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore release the active compound. Suitable carriers and formulations for such administration are known in the art.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compounds (resolvins and/or protectins and/or precursors or analogues thereof) of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

More specifically, the invention features an article of manufacture that contains packaging material and at least one compound of the present invention, for example Compound (I) and/or Compound (H) and/or functional derivatives thereof are contained within the packaging material. The packaging material contains a label or package insert indicating that the formulation can be administered to the subject with neovascularization in an amount, at a frequency, and for a duration effective treat or prevent symptoms associated with such disease states or conditions discussed throughout this specification. In some embodiments, the proliferative disorder is a cancer. In some embodiments, the cancer is for example a MIS-responsive cancer and/or expresses MISRII, for example ovarian cancer.

Remington's Pharmaceutical sciences Ed. Germany, Merk Publishing, Easton, Pa., 1995 (the contents of which are hereby incorporated by reference), discloses various carriers used in formulating pharmaceutical compositions and known techniques for the preparation thereof. Some examples of materials which can serve as pharmaceutically acceptable carriers include, but are not limited to, sugars such as lactose, glucose and sucrose; starches such as corn starch and potato starch; cellulose and its functional derivatives such as sodium carboxymethyl cellulose, ethyl cellulose and cellulose acetate; malt; gelatin; talc; excipients such as cocoa butter and: suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; water; isotonic saline; Ringer's solution, ethyl alcohol, and phosphate buffer solutions, as well as other non-toxic compatible lubricants such as sodium lauryl sulfate and magnesium sulfate, as well as coloring agents, releasing agents, coating agents, sweetening, flavoring and perfuming agents, preservatives and antioxidants can also be present in the composition, according to the judgment of the formulator.

Uses

In another embodiment, the present invention provides a method for treating a variety of conditions by administering an effective amount of a pyrazoloathrone and functional derivatives thereof of the invention to a subject in need thereof. Conditions that may be treated by the compounds of this invention, or a pharmaceutical composition containing the same, include any condition which is treated or reduces the symptoms by administration of MIS or activation of MIS signaling or activation of MISRII, and thereby benefit from administration of a pyrazoloathrone and functional derivatives thereof. Representative conditions in this regard include, for example, but not limited to, cancers that express MIS receptors, for example cancer that express MISRII, for example, but not limited to ovarian, cervical and endometrial cancer. Other conditions which can be treated with MIS or activation of MIS signalling reduces the symptoms are, for example, rheumatoid arthritis, proliferative diseases such as cancer, treatment of prostatic cancer, polycysic ovarian disease, benign prostatic hypertrophy and precocious puberty and other hyperandrogen disorders such as testitoxicosis.

Accordingly, the present invention relates to the use of pyrazoloathrone and functional derivatives thereof for the treatment of any disorder where administration of the MIS protein or a nucleic acid encoding MIS protein or a functional derivative of MIS or activation MISRII is whole, or part, of the therapeutic regime. In some embodiments, the pyrazoloathrone is SP600125 (or compound 1 herein), as disclosed in U.S. Pat. No. 7,119,114 which is incorporated in its entirety herein by reference. In other embodiments, the pyrazoloathrone is a derivative of pyrazoloathrone, for example substituted antra(1,9-cd)pyrazol-6(2H)-one, and anthrapyrazolone derivatives as disclosed in European Patent EP 0103381 and EP0700390, which are incorporated in their entirety herein by reference.

In some embodiments, the methods of the present invention are directed to use of pyrazoloathrone and functional derivatives thereof with other therapeutic agents, for example chemotherapy agents, wherein the chemotherapy agents, for example paclitaxel or MIS can be used at a lower dose that results in decreased side effects.

Uses of Pyrazoloanthrone or Functional Derivatives or Analogues Thereof for the Treatment of Excess Androgen States Another embodiment, the pyrazoloanthrone or functional derivatives or analogues thereof, such as SP600125 can be used for the treatment of a disorder associated with excess androgen production in a subject. The inventors have previously demonstrated that the administration of MIS protein and/or MIS nucleic acid decreases levels of androgen in a subject, and decreases serum levels of androgen in a subject, as disclosed in U.S. Pat. No. 6,673,352 and U.S. patent application Ser. No. 10/683,346, which are incorporated herein in their entirety by reference. Transgenic mice that overexpress MIS have also shown to have decreased serum testosterone concentrations, and administration of MIS results in decreased serum testosterone levels (Sriraman et al., J. Androl. 2001, 22(5):750-8 and Trbovich et al., PNAS, 2001 Mar. 13; 98(6):3393-7). MIS has also been demonstrated to suppress both androgen-stimulated growth and androgen-independent survival of cells, and MIS regulates prostate growth by suppressing testicular testosterone synthesis also direct regulates androgen-induced gene expression and growth in the prostate at the cellular level (Trann et al, Mol. Endocrinol. 2006, 20(10):2382-91). Accordingly, in another embodiment, the present invention also relates to methods to use the Androgen stimulates or controls the development and maintenance of masculine characteristics in vertebrates by binding to androgen receptors. Androgens are also known as androgenic hormones or testoids, and are also the precursor of all estrogens, the female sex hormones. The primary and most well-known androgen is testosterone.

Without wishing to be bound by theory, excessive androgen production by the adrenal glands and/or the ovary, results in androgen excess and can result from increased local tissue sensitivity to circulating androgens. Androgen excess affects different tissues and organ systems, causing clinical conditions ranging from acne to hirsutism to frank virilization.

Hyperandrogenism, which refers to the excess production and secretion of androgens and precursors, is a common and sometimes serious endocrinopathy for women of reproductive age. The excess androgens and precursors originate from the adrenal glands and ovaries in various proportions and manifest in varying effects depending on the amount of excess androgen. Clinical manifestations range from hirsutism (excessive hair growth of male pattern, sometimes accompanied by acne) to virilization (clitorimegaly, temporal balding, deepening of voice, or enhanced musculature).

Hyperandrogenism occurs as part of a wide spectrum of disease manifestations, including polycystic ovary syndrome (PCOS) which is a variable combination of hirsutism, infertility, obesity, insulin resistance and polycystic ovaries, the HAIR-AN syndrome (hyperandrogenism, insulin resistance and acanthosis nigricans), ovarian hyperthecosis (HAIR-AN with hyperplasia of luteinized theca cells in ovarian stroma), and other manifestations of high intraovarian androgen concentrations (e.g., follicular maturation arrest, atresia, anovulation, dysmenorrhea, dysfunctional uterine bleeding, infertility), androgenproducing tumors (virilizing ovarian or adrenal tumors).

Hirsutism is excessive recognizable hair growth characterized by an increase in the number and length of terminal hairs in androgen-sensitive areas. Racial, familial, genetic, and ethnic differences all affect the occurrence of hirsutism. Hirsutism is difficult to quantitate. The entire body needs to be inspected and the findings must be documented carefully. Particular attention should be directed to the chin, lip, sideburns, breasts, and sternum, the midline between the umbilicus and the pubis and the thigh.

Ferriman and Gallwey published a rating scale for grading hirsutism and is commonly known by persons of ordinary skill in the art. This scale allows the physician to measure a response to therapy objectively. This system is the most widely used and evaluates body areas for absent-to-severe hirsutism with scores of 0-4, respectively. Scores of 8 and higher are consistent with a diagnosis of hirsutism. This scale does not measure the thickness of the hair, which is another way of objectively assessing excess hair. Scoring systems are a useful aid in quantifying hirsutism and in evaluating treatment response. Even with scores greater than 8, the patient provides the definition. From a clinical standpoint, the patient can determine if he or she notices a difference. Photographs are helpful for documentation and for following the progress of therapy.

Virilization is relatively uncommon; it occurs with extreme hyperandrogenism. Virilization is characterized by temporal balding, breast atrophy, androgenic muscle development, clitoral hypertrophy, amenorrhea, deepening of the voice, and extreme hirsutism.

Current medical therapies for women are directed against the adrenals, the ovaries or the androgen receptor. Glucocorticoid therapy is directed against the adrenal glands but is limited, in some cases, by unwanted suppression of cortisol synthesis. GnRH therapy is directed against the ovaries, but is expensive, and its long-term effects are unknown. Further, therapy using oral contraceptives may be unsuitable because most contain progestins with androgenic activity.

Because the abnormal production of androgens is implicated in the pathways of many diseases and/or disorders for which there are no acceptable treatments, a need exists to find small molecules to inhibit the production of gonadotropins and/or androgens in mammals for their treatment and/or prophylaxis.

Accordingly, in one embodiment, the pyrazoloanthrone or functional derivatives or analogues thereof, such as SP600125 can be used for the treatment of a disorder associated with excess androgen production in a subject.

The term "androgen" is used herein to mean steroids that encourage the development of male sex characteristics and include the steroid derivatives of androstane including, testosterone, androstenedione, and analogs.

As used herein, a disease state or disorder characterized by "androgenic dependency" is a disease state which is exacerbated by, or caused by, insufficient, excessive, inappropriate or unregulated androgen production. Examples of such diseases in men include, but are not limited to, BPH, metastatic prostatic carcinoma, testicular cancer, androgen dependent acne, male pattern baldness and precocious puberty in boys. Examples of such diseases in women include, but are not limited to, hyperandrogenism, hirsutism, virilization, POCS, HAIR-AN syndrome, ovarian hyperthecosis, follicular maturation arrest, atresia, anovulation, dysmenorrhea, dysfunctional uterine bleeding, infertility, androgen-producing tumors.

As used herein, "androgen inhibiting" refers to an effective amount of an the pyrazoloanthrone or functional derivatives or analogues thereof as defined herein, such as SP600125, which will cause a decrease in the in vivo levels of the androgen to normal or sub-normal levels, when administered to a subject for the prophylaxis or treatment of a disease state which is exacerbated by, or caused by, excessive or unregulated androgen production.

In some embodiments, the pyrazoloanthrone or functional derivatives or analogues thereof as disclosed herein, such as SP600125, can be used to treat prostate cancer. The impact of androgens on prostate carcinoma is known, as is the treatment of prostate cancer by androgen deprivation, including androgen blockade and inhibition of androgen synthesis (Huggins et al., Archs. Surg., Vol. 43, pp. 209-223 (1941)). J. Steroid Biochem. Molec. Biol., Vol. 37, pp. 349-362 (1990)). In addition, steroid hormones are widely used as contraceptives. Anti-spermatogenic agents are male contraceptives that inhibit spermatogenesis, the process leading to mature spermatazoa. Drugs that interfere in this process include androgens and anti-androgens. Since the anti-androgenic effects of the pyrazoloanthrone or functional derivatives or analogues thereof as disclosed herein, such as SP600125, are reversible, the compounds can also be used as a male contraceptive agent. Korolkovas, A., Essentials Of Medicinal Chemistry, Second Edition, pp. 1032 (1988).

In some embodiments, other agents can be used in combination with the pharmaceutical compositions comprising pyrazoloanthrone or functional derivatives or analogues thereof as disclosed herein for the treatment of excess androgen in a subject. In some embodiments, the agents function to lower the serum-free androgen levels and blocking the peripheral androgen action. Examples of such agents include, but are not limited to, suppression of ovarian androgens by administration of estrogens and/or progestins (i.e., contraceptive pill) or GnRH agonist and add-back estrogen therapy; suppression of adrenal androgens by administration of glucocorticoids (such as dexamethasone, prednisolone), antiandrogens (such as spironolactone, flutamide, cyproterone acetate), 5α-reductase inhibitor (such as finasteride), bromocriptine, and insulin-sensitizing drugs (such as metformin, thiazolidinediones).

Subjects amenable to treatment of the pyrazoloanthrone or functional derivatives or analogues thereof by the methods as disclosed herein are subjects that have been identified with a disease or disorder associated with excess androgen levels, such as, for example disorders such as, but not limited to BPH, prostate carcinoma, benign prostic hypertrophy, testicular cancer, androgen dependent acne, male pattern baldness, precocious puberty, hyperandrogenism, hirsutism, virilization, POCS, HIAR-AN syndrome, ovarian hyperthecosis, follicular maturation arrest, atresia, anovulation, dysmenorrheal, dysfunctional uterine bleeding, infertility and androgen-producing tumors.

In some embodiments, subjects amenable to treatment of the pyrazoloanthrone or functional derivatives or analogues thereof by the methods as disclosed herein are subjects with congenical adrenal hyperplasma (CAH), which can be commonly identified by one of ordinary skill in the art. CAH is most typically an autosomal recessive disorder where the enzyme 21-hydrolase is missing or functionally deficent. Alternatively subjects with CAH can have a loss and/or reduction in the function of 11α-hydroxylase enzyme and/or a 3α-hydroxy-steroid dehydrogenase enzyme. When these enzymes are missing or functioning at low levels, the body cannot make adequate amounts of the adrenal steroid hormones cortisol and aldosterone. High levels of ACTH that stimulate adrenal hyperplasia and hypersecretion of androgen precursors for cortisol and aldosterone synthesis ensue. CAH can appear in utero or develop postnatally. Pseudohermaphroditism may be present at birth.

The 21-hydroxylase deficiency is the most common autosomal-recessive disorder (more common than cystic fibrosis) and manifests itself with elevated levels of 17-hydroxyprogesterone. The 11a-hydroxylase deficiency is characterized by elevated levels of 11-deoxy-cortisol (compound S) and results in elevated levels of deoxycorticosterone (DOC), a mineralocorticoid. Hypertension and hypokalemia can be a prominent feature of 11a-hydroxylase deficiency. Another form of CAH, 3a-hydroxy-steroid dehydrogenase deficiency, results in elevated levels of pregnenolone, 17-hydroxy-pregnenolone, and DHEA. This condition is lethal if not detected because no corticosteroids are synthesized.

A partial defect in the above enzymes that manifests after puberty results in elevated levels of adrenal steroids via the same mechanism. The elevations are not as marked as they are with the congenital condition and this condition is referred to as nonclassical (maturity-onset or late-onset) CAH. Accordingly, in some embodiments, subjects amenable to treatment of the pyrazoloanthrone or functional derivatives or analogues thereof by the methods as disclosed herein are subjects with nonclassical (maturity-onset or late onset) CAH.

In some embodiments, subjects amenable to treatment of the pyrazoloanthrone or functional derivatives or analogues thereof by the methods as disclosed herein are female subjects with testosterone levels about or exceeding 2.0 ng/mL (200 ng/dL, 8.92 nmol/L) or at least about 2.5 times the upper limit of the reference range. In some embodiments, such subjects have Sertoli-Leydig cell tumors, hilus cell tumors, and lipoid cell (adrenal rest) tumors are the most common. Sertoli-Leydig cell tumors reach palpable size at the time of clinical diagnosis, whereas hilar cell and lipoid cell tumors are difficult to detect by any means because of their small size.

In some embodiments, subjects amenable to treatment of the pyrazoloanthrone or functional derivatives or analogues thereof by the methods as disclosed herein are subjects with tumors of the adrenal glands (adenomas, carcinomas), which secrete elevated levels of androgens. In such embodiments, such subjects amenable to treatment by the methods as disclosed herein can be identified by having a DHEAS level of about or exceeding 7 µg/mL (18 mmol/L).

Other subjects that are amenable to the methods of treatment of excess androgen states as disclosed herein include, for example, classical and nonclassical (late-onset) CAH, cushing syndrome, where subjects with Cushing syndrome secrete elevated androgens, Hyperandrogenic, insulin resistance, and acanthosis nigricans (HAIR-AN) syndrome. In some embodiments, other subjects amenable to the methods of treatment of excess androgen states as disclosed herein include, for example, subjects with mild androgenic disorders, such as, but not limited to, Ovulatory PCOS (Ovulatory hyperandrogenic subjects with polycystic ovary at ultrasonography), Idiopathic hyperandrogenism (an oOvulatory hyperandrogenic subject but with normal ovaries at ultrasonography); Idiopathic hirsutism (subjects with an androgenic phenotype with normal androgens).

Reference testosterone levels and DHEAS levels are commonly known by persons of ordinary skill in the art, and are disclosed in Guay et al, International Journal of Impotence Research (2004) 16, 112-120, which is incorporated herein in its entirety by reference. Briefly, normal androgen levels in women between the ages of 20 and 49 years range between; DHEAS; about 195.6-140.4 ug/dl; serum testosterone about 51.5-33.7 ng/dl and free testosterone 1.51-1.03 pg/ml. Accordingly, subjects amenable to the treatment of the pyrazoloanthrone or functional derivatives or analogues thereof by the methods as disclosed herein have at least about a 20%, or at least about a 30% or at least about a 40% or at least about a 50%, or at least about a 60% or at least about a 70%, or at least about a 80%, or at least about a 90%, or at least about a 100% or greater increase in DHEAS or serum testosterone, or free testosterone levels as compared to the highest range value of the normal value for DHEAS (195.6 µg/dl), serum testosterone (51.5 ng/dl), free testostereone (1.51 pg/ml). In some embodiments, subjects amenable to the treatment of the pyrazoloanthrone or functional derivatives or analogues thereof by the methods as disclosed herein have at least about a 2-fold, or at least about a 3-fold, or at least about a 4-fold, or at least about a 5-fold, or at least about a 10-fold or greater increase in DHEAS or serum testosterone, or free testosterone levels as compared to the highest range value of the normal value for DHEAS (195.4 µg/dl), serum testosterone (51.5 ng/dl), free testostereone (1.51 pg/ml).

DHEAS can be measured by one of ordinary skill in the art using a kit from by Diagnostic Products Corporation of Los Angeles, Calif., USA. Cross-reactivity has previously been determined as being 100% for DHEAS and 0.121% with androstenedione, 15% with 9-hydroxyandrostenedione, 0.046% with estrone 3 sulfate, 0.55% with androsterone sulfate, 0.5% with DHEA and negligible for all other steroids tested. Free Testosterone can be measured by one of ordinary skill in the art using was measured using the Coat a Count Kits of Diagnostic Products Corporation, Los Angeles, Calif., USA. Cross-reactivity has previously been determined to be 0.41% for dihydrotestosterone, 0.01% for androstenedione, 0.10% for methyl testosterone ando0.01% for all other steroids tested. Total serum testosterone levels can be measured by one of ordinary skill in the art using with the Immunochem serum testosterone kit of ICN Biomedicals Inc., Diagnostic Division of Costa Mesa, Calif., USA.

The assays to determine serum pregnenolone and 17-hydroxypregnenolone can be performed by one of ordinary skill in the art from the kit from Quest Laboratory in Tarzana, Calif., USA. Free Androgen Index (FAI) can be calculated using the following formula:

$$(\text{Total testosterone ng/dl} \times 0.0347)/(\text{SHBG nmol/l}) \times 100 = \text{FAI}$$

Assay for Identifying MIS Mimetics

In another aspect, the present invention is the first high throughput quantitative assay directed to methods of screening for agents or molecules that function as a mimetic of MIS or activate the MISRII or activate MISRII-mediated signaling. In some embodiments, the present invention provides methods an assay, wherein the agent is contacted with a cell comprising a nucleic acid construct comprising a BMP-responsive element operatively linked to a nucleic acid encoding a reporter gene. In some embodiments, the reporter gene encodes a protein with fluorescent activity and/or chromogenic activity, for example but not limited to fluorescent proteins, for example green fluorescent protein (GFP) or variants thereof or bioluminescent proteins, for example luciferase or variants thereof. In some embodiments, the cell also comprises a nucleic acid construct comprising MISRII. In some embodiments, the agent is a small molecule, nucleic acid, nucleic acid analogue, aptamer, ribosome, peptide, protein, antibody or variants or fragments thereof. An agent that functions as a MIS mimetic or functional derivative of MIS or activates MISRII-mediated signaling will result in a change in the signal from the reporter gene, where the change is a result of contacting the cell with agent compared to when the cell is not contacted with the agent.

In some embodiments, the method involves the introduction into a cell of a nucleic acid construct encoding a reporter gene which is operatively linked to a BMP-responsive element (BME) or a fragment thereof. The BMP-responsive element on the mouse (M. mus) genome is located on chromosome 2 (Chr2) and corresponds to RefSeq No: NT_039207.6 93504644-93506272 (SEQ ID NO:1). Accordingly, the reporter gene can be operatively linked to a nucleic acid encoding a SEQ ID:1, or a fragment or derivative thereof. In some embodiments, the BMP response elements is a homologue or cognate of SEQ ID NO:1, for example but not limited to a human or other primate homologue of SEQ ID NO:1. The introduction of the nucleic acid can be by any method described commonly known by persons skilled in the art, for example vectors, viral vectors, transfection, naked DNA etc. In some embodiments, the method also involves introduction into the cells of a nucleic acid construct encoding MISRII or a homologue or fragment thereof, operatively linked to a regulatory sequence. In some embodiments, the regulatory sequence is a promoter, and in some embodiments the promoter is constitutively expressed and in alternative embodiments the promoter is an inducible promoter, a tissue specific promoter and/or a developmentally regulated promoter.

Cells from any species and any tissue can be used to carry out the methods of the invention. The cells are cultured or maintained in a conventional culture medium under suitable conditions permitting growth of the cells. For example, the cell is cultured in standard tissue culture media containing the necessary reagents to select for cells which stably retain the nucleic acid construct described above. Cells may be cultured in standard tissue culture dishes e.g. multidishes and microwell plates, or in other vessels, as desired. In some configurations, the assay can be conducted in a 96 well; 386-well or other multi-well plates.

In one embodiment, agents are added to the culture media to assess their effect on the signal produced from the reporter gene within the cell. Cells at this time may be bathed in tissue culture media (with or without serum) or balanced salt solution. The agent may be applied to the media, wherein it contacts the cell and induces its effects or it may be intracellular within the cell. In one embodiment, the agent may be a chemical or library of chemicals. These may be cell permeable and therefore added directly to the cells. Alternatively, it may be necessary to make the cells permeable using streptolysin O, tetanolysin or another permeabilizing agent known by persons skilled in the art. In another embodiment, the agent may be a protein or peptide or a nucleic acid sequence. These may be directly applied to the cells, or alternatively introduced into the cells by a vector and when expressed, these proteins and nucleic acids act as intracellular agent. In one embodiment, agents are nucleic acid sequences are individual DNA molecules having one or more genes, each operatively linked to the same or different regulatory sequences to the one operatively linked to the in. The constructs may be introduced simultaneously, or consecutively, each with the same or different markers.

In some embodiments, the cells are exposed to at least one agent. In other embodiments, the cells are exposed to more than one agent. The agent may be of the same type (i.e. chemical, procedure, protein, nucleic acid, intrinsic stimuli etc.) or may be any combination of agents. Exposure of the cells to an agent may be simultaneous, sequentially or consecutive, and in any order. Cells may be exposed to any agent once or any number of times. The time of exposure of the cells to the agent can vary, depending on the agent and the cells being used, and the level of expression of the nucleic acid construct comprising the BRE and reporter gene.

The cells used in the methods described here in may be prokaryotic, but are preferably eukaryotic, including plant, yeast, worm, insect and mammalian. In another embodiment, the cells are mammalian cells, particularly primate, human and can be associated with any animal of interest, including but not limited to, transgenic animals and domestic animals, such as equine, bovine, murine, ovine, canine, feline, etc. Among these species, various types or cells can be used, such as hematopoetic, neural, mesenchymal, cutaneous, mucosal, stromal, muscle, ovarian, spleen, reticuloendothelial, epithelial, endothelial, hepatic, kidney, gastrointestinal, pulmonary etc. Also, in another embodiment, the cells are stem cells and progenitors, such as hematopoeitic neural, stromal, muscle, ovarian, hepatic, pulmonary, gastrointestinal, etc.

In some embodiments, the reporter gene is any gene which can be detected. Examples of commonly used reporter genes are fluorescent proteins, for example GFP and GFP-like proteins and modified versions thereof, and bioluminescent enzymes, for example luciferase or modified proteins thereof. Other reporter genes can be chromogenic proteins or enzymes which catalyze a reaction to produce a substrate that is detectable. Examples of such enzymes include, for example but not limited to beta-galactosidase, beta-lactamase, beta-glucosidase, beta glucuronidase, chloramphenicol acetyl transferase. Examples of fluorescent proteins are, without limitation green fluorescent protein (GFP) or enhanced green fluorescent protein (EGFP). In alternative embodiments, the fluorescent protein is yellow fluorescent protein (YFP), an enhanced yellow fluorescent protein (EYFP), a blue fluorescent protein (BFP), an enhanced blue fluorescent protein (EBFP), a cyan fluorescent protein (CFP), an enhanced cyan fluorescent protein (ECFP) or a red fluorescent protein (dsRED) or any other natural or genetically engineered fluorescent protein of those listed above. In yet further embodiments, the reconstituted fluorescent proteins may comprise of a mixture of fragments from the same or a combination any of the above listed fluorescent proteins. Methods to detect the products from the reporter genes are commonly known by persons of ordinary skill in the art.

In some embodiments, the bioluminescent enzyme, for example luciferase, catalyzes a substrate, herein referred to as a "bioluminescence substrate" which is a compound that is oxidized in the presence of luciferase and any necessary activators, to generates light. These substrates are referred to "luciferins" herein, and are substrates that undergo oxidation in a bioluminescence reaction. These bioluminescence substrates include any luciferin or analogue thereof, or any synthetic compound that generates light. Such molecules include naturally-occurring substrates, modified forms thereof and synthetic substrates [see e.g. U.S. Pat. Nos. those described in U.S. Pat. Nos. 5,374,534 and 5,098,828 which are incorporated herein in their entirety by reference]. Exemplary luciferins include those described in U.S. Pat. No. 6,436,682, and functional derivatives thereof, analogues thereof, synthetic substrates, as well as dioxetanes [see e.g. U.S. Pat. Nos. 5,004,565 and 5,455,357 which are incorporated herein in their entirety by reference], and other compounds that are oxidized by luciferase in a light-producing reaction [see, e.g. U.S. Pat. Nos. 5,374,534, 5,098,828 and 4,950,588 which are incorporated herein in their entirety by reference]. Bioluminescence substrates, thus, include those compounds that those skilled in the art recognize as luficerins. In one embodiment, the luciferin is coelenterazine and analogues thereof, which include molecules in U.S. Pat. No. 6,436,682, and for example, see Zhao et al, (2004), Mol Imaging, 3; 43-54.

Methods to measure bioluminescence are well known to those skilled in the art. Bioluminescence reactions are also well-known to those skilled in the art, and any such reaction may be adapted for used in combination with articles of manufacture as described herein.

The term "agent" refers to any entity which is normally not present or not present at the levels being administered in the cell. Agent may be selected from a group comprising; chemicals; an action; nucleic acid sequences; proteins; peptides; or fragments thereof. A nucleic acid sequence functioning as an environmental stimuli may be RNA or DNA, and may be single or double stranded, and can be selected from a group comprising; nucleic acid encoding a protein of interest, oligonucleotides, nucleic acids, nucleic acid analogies, for example but not limited to peptide nucleic acid (PNA), pseudo-complementary PNA (pc-PNA), locked nucleic acids (LNA) and derivatives thereof etc. Nucleic acid sequence encoding environmental stimuli can also inhibit the activity of a regulatory sequence and/or constitutively active promoter. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (miRNA), antisense oligonucleotides etc. A protein and/or peptide or fragment thereof, functioning as an environmental stimuli can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell.

In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

EXAMPLES

The examples presented herein relate to the use of pyrazoloathrone and functional derivatives thereof as a MIS mimetic, and the use of pyrazoloathrone and functional derivatives thereof for the treatment of disease and disorders where MIS is effective at treating or reducing the symptoms of the disorder. The pyrazoloathrone and functional derivatives thereof can also be used in conjunction with other therapeutic agents, for example chemotherapeutic agents MIS and paclitaxel to reduce their therapeutic effective dose in the treatment of cancers. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

Small Molecule Screen.

To identify molecules that interact with the MISRII, we developed a reporter assay where binding to MISRII activates a firefly luciferase reporter driven by the BMP-responsive element (BRE) promoter kindly provided by Dr. Peter ten Dijke (The Netherlands Cancer Institute, The Netherlands) The BMP promoter region on mouse *M. mus* is located on chromosome 2 (Chr2) and corresponds to RefSeq No: NT_039207.6 93504644-93506272 (SEQ ID NO:1). The BRE-luciferase reporter (Korchynskyi and ten Dijke, 2002, Logeart-Avramoglou, 2006) has multiple optimized BMP response elements (3 SBE, 7 GC, and 4 CAGC) driving the expression of the firefly luciferase. This reporter construct together with a control *Renilla luciferase* reporter phRL-CMV (Promega, Madison Wis.) and a rat MISRII cDNA expression construct (Teixeira, 1996) were transiently transfected into COST cells and plated in 384 well plates. Primary screens were performed at the Harvard Institute of Chemistry and Cell Biology screening facility. Compounds from chosen libraries were added at a volume of 100 nl at 5 mg/ml concentration in DMSO into 30 µl cell media and cultured for 24 h at 37° C., after which the luciferase activity was measured with reagents from Promega according to the manufacturer's instructions. A hit was identified as causing a fold induction over the plate median and each compound was tested in duplicate in separate plates. MIS was used to control for intra- and inter-assay variability.

Cell Culture.

COS7 cells were cultured in DMEM supplemented with 10% female Fetal Bovine Serum (FBS) and MOVCAR7 cells were maintained in DMEM with 4% female FBS. Both cell-lines were cultured in a humidified 5% $CO_2$ incubator at 37° C. with added 2 mM L-glutamine, 100 U/ml penicillin and 100 µg/ml streptomycin.

Transfection and Reporter Assay.

COS7 cells were plated at a density of 5000 cells/well in 96-well plates for secondary screens. The day after plating cells were transfected with rat MISRII receptor or EGFP-N1 (Clontech, Mountain View Calif.) together with BRE firefly luciferase reporter construct and phRL-CMV using TransIT-LT1 transfection reagent (Mirus Bio Corporation, Madison Wis.). The following day, cells were treated with SP600125 and/or MIS at the indicated concentrations for 24 h, or as otherwise stated for the time course experiments, in 1% serum media. MOVCAR7 cells were transfected with the BRE and phRL-CMV luciferase reporters and treated with MIS and/or SP600125 at the indicated concentrations in growth media for 24 h. Results were obtained using the Dual Luciferase reporter assay according to the manufacturer's instructions (Promega). Plates were read in a Wallac Victor2 luminometer (PerkinElmer, Wellesley Mass.). BMP2 and activin were purchased from R&D Systems, Minneapolis Minn.

Proliferation Assay.

The effect of SP600125 on cell proliferation was measured by the 3-(4,5-dimethylthiazol-2-yl)-2,5-diphenyltetrazolium bromide assay (Mosmann, 1983) in a mouse ovarian cancer cell line, MOVCAR7 cells that were kindly provided by Dr. Denise Connolly, Fox Chase Cancer Center, Philadelphia Pa. (Connolly, 2003). The 4306 cells were provided by Dr. Daniela Dinulescu, Brigham and Women's (Boston) (30). Cells were plated at a density of 1000 cells/well in 96-well plates and treated 24 h later. The cell proliferation was measured after 7 days by registering the absorbance at 550 nm. Paclitaxel was manufactured by Ivax Pharmaceuticals and obtained from the MGH pharmacy.

Western Blotting.

Cells were washed in PBS and lysates were prepared in 1× Passive lysis buffer (PLB) provided with the Dual luciferase reporter assay kit (Promega). The lysates were cleared by centrifugation and the protein concentration was determined by Bradford assay (Bio-Rad, Hercules Calif.). Equal volumes of protein were loaded onto a NuPAGE 4-12% Bis-Tris gradient gel with MOPS-buffer (Invitrogen, Carlsbad Calif.) for polyacrylamide gel electrophoresis. Following transfer to a nitrocellulose by electroblotting, the membrane was blocked in 5% milk Tris-buffered saline/Tween20 (TBS-T) for 1 h at room temperature and incubated with primary antibody (pJNK, c-jun and phosph c-jun antibodies were purchased from Cell Signalling, Danvers, Mass.; amd JNK antibody was published from Santa Cruz Biotechnology, Calif.) overnight at 4° C. in 5% BSA followed by incubation with secondary horseradish peroxidase conjugated anti-rabbit antibody (Jackson ImmunoResearch, Westgrove Pa.) for 1 h. Immunoreactive proteins were detected by enhanced chemiluminescence (Pierce, Rockford Ill.). Anisomycin was purchased from Calbiochem.

MIS Preparation and Bioassay.

Recombinant human MIS was prepared from Chinese hamster ovary cells stably transfected with a construct of the human MIS gene and purified from serum-free media by serial carbohydrate affinity and ion exchange chromatography or by immunoaffinity chromatography (Lorenzo, 2002). The bioactivity of the MIS was then verified using an established organ culture assay, which grades Müllerian duct regression of the female 14.5-day gestation rat urogenital ridge (Donahoe, 1977).

Statistical Analysis.

Data were analyzed by ANOVA of the repeated experiments followed by the Tukey's posthoc test when appropriate with Prism (GraphPad Software, San Diego Calif.). When the control data was normalized to 1, this data was excluded from the statistical analyses. Synergy was calculated by two-way factorial ANOVA (Pieretti-Vanmarcke, 2006a). For all analyses, significance was assigned at $p<0.05$.

Example 1

SP600125 Activates a BMP-Responsive Promoter in Conjunction with MISRII

MIS-specific signaling absolutely requires the MIS type II receptor and knockout studies in mice show phenocopy results when either MISRII or the MIS ligand is deleted (Behringer, 1994, Mishina, 1996). This allowed the inventors to develop an exquisitely precise screen for MIS signaling so that only cells that express MISRII initiate MIS downstream signaling. The inventors used the BRE-luciferase reporter in COS cells cotransfected with an expression vector containing the rat MISRII receptor cDNA (Teixeira, 1996). Screening of 15,000 compounds resulted in several hits that activated the MISRII at levels near those caused by its native ligand, MIS, in a reporter gene assay that identifies compounds that activate the BMP-responsive element through MISRII interaction. The first suitable candidate to undergo further analysis after the primary screen was the pyrazoloathrone derivative; antra[1,9-cd]pyrazol-6(2H)-one, a JNK inhibitor II, also known as SP600125.

To characterize the activity of SP600125 and its effect on MIS signal transduction, the inventors performed experiments with increasing concentrations of SP600125 and measured BRE-luciferase activity (FIG. 1). SP600125 induced luciferase expression in a concentration-dependent manner in MISRII-transfected COS7 cells and at 25 uM reached 6-fold higher than that of vehicle-treated cells. Luciferase expression was also induced with 33.3 uM and 100 uM concentrations of added SP600125 by 15- and 25-fold, respectively, (shown with bars after the dotted line) but the *Renilla luciferase* was inhibited by approximately 60% suggesting toxic effects to the cells. Only cells transfected with MISRII showed a significant induction in luciferase activity indicating that MISRII expression was necessary for SP600125 to induce MIS signaling in these cells.

Figure 5:
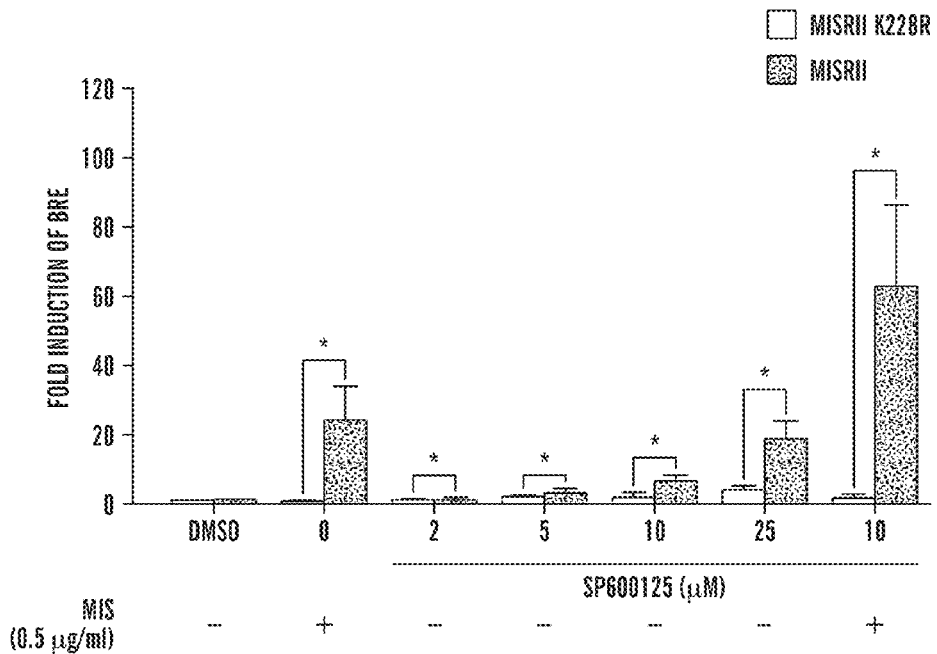
FIG. 5 shows SP600125 induces MISRII-dependent BRE-luciferase reporter expression in COS7 cells and increase MIS response to these cells. COS7 cells were transfected with normal MISRII or a kinase-deficient receptor MISRIIK228R and treated with increasing doses of SP600125 and/or MIS for 24 hrs. Results shown represent the mean values from four independent experiments performed in triplicates (Error bars represent standard error of the mean, *, P<0.05). These results demonstrate that the kinase activity of MISRII is required to observe SP600125 mediated activation of the MIS signal transduction pathway.

To further demonstrate that the activating effect of SP600125 on BRE-luciferase was MISRII specific, the inventors used a reporter construct where a conserved lysine (K228) in the ATP-binding region of the receptor was changed to an arginine (K228R), disabling the kinase activity of the receptor (4). In FIG. 5 the inventors demonstrate that neither MIS nor SP600125 activates BRE-luciferase when kinase-deficient receptor is overexpressed. In addition, the inventors demonstrated that a further increase of the activity when MUS was added in combination with SP600125, an effect that was completely abolished with the K228R, demonstrating that the serine/threonine activity of the MISRII is needed for activation of BRE-luciferase.

Figure 2A:
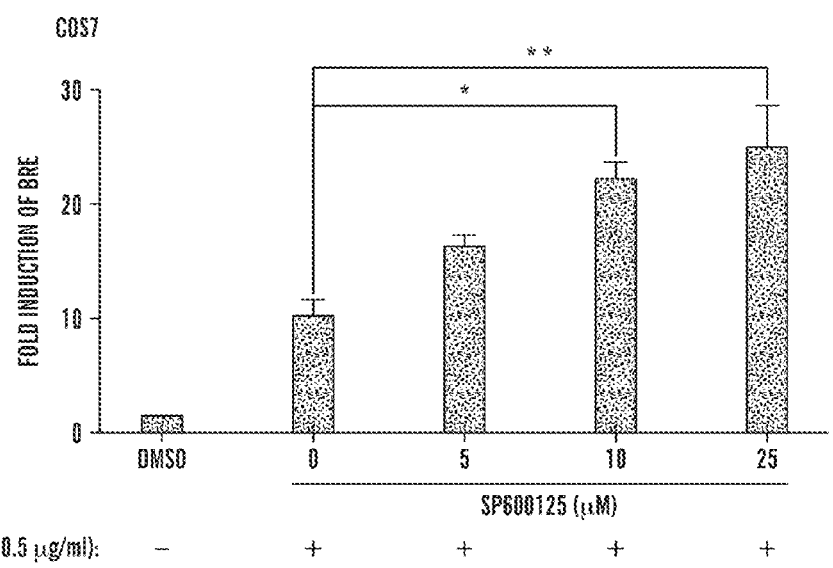
FIGS. 2A-2E shows that SP600125 exerts a synergistic effect on BRE-Luciferase induction in combination with MIS.
Figure 2B:
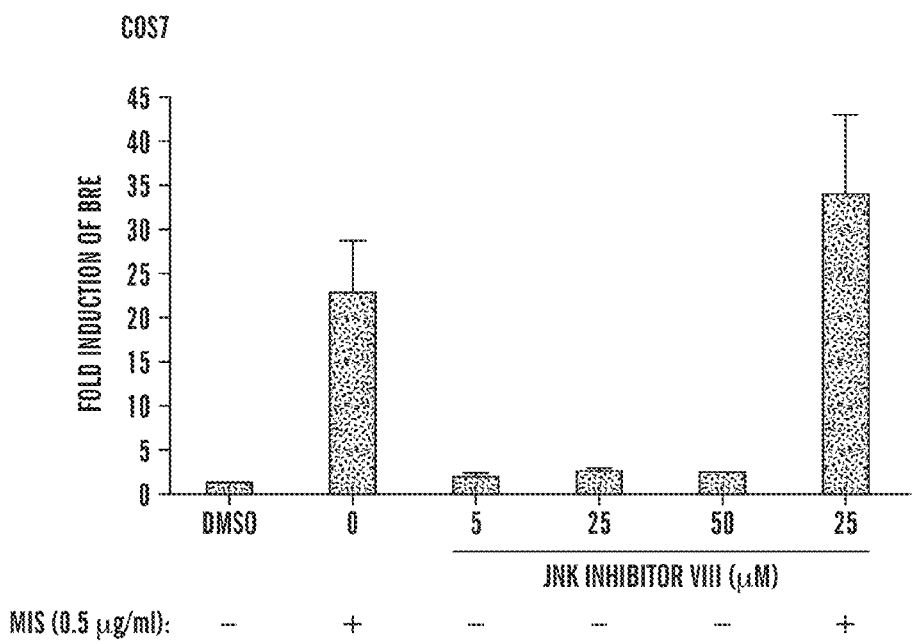
Figure 2C:
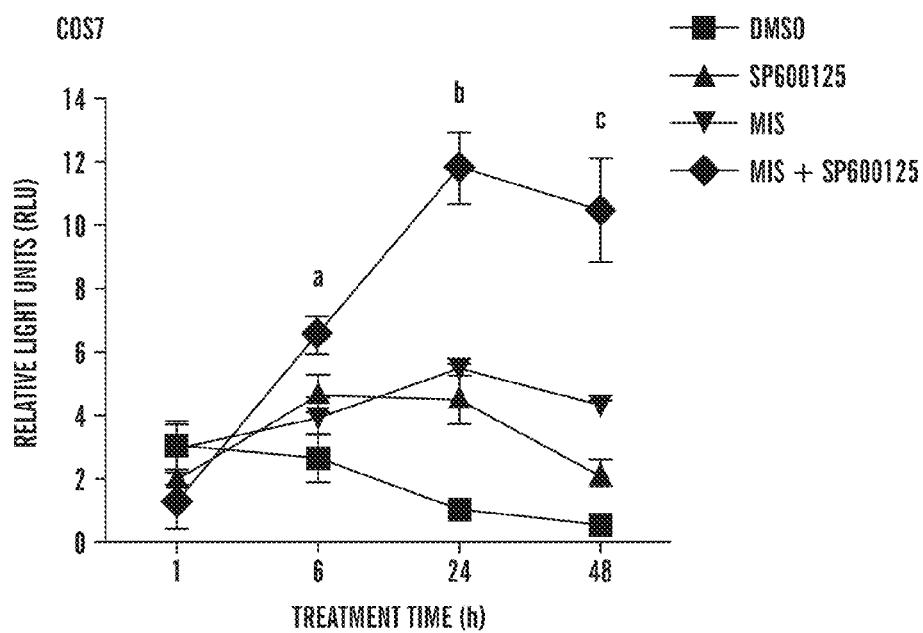
Figure 2D:
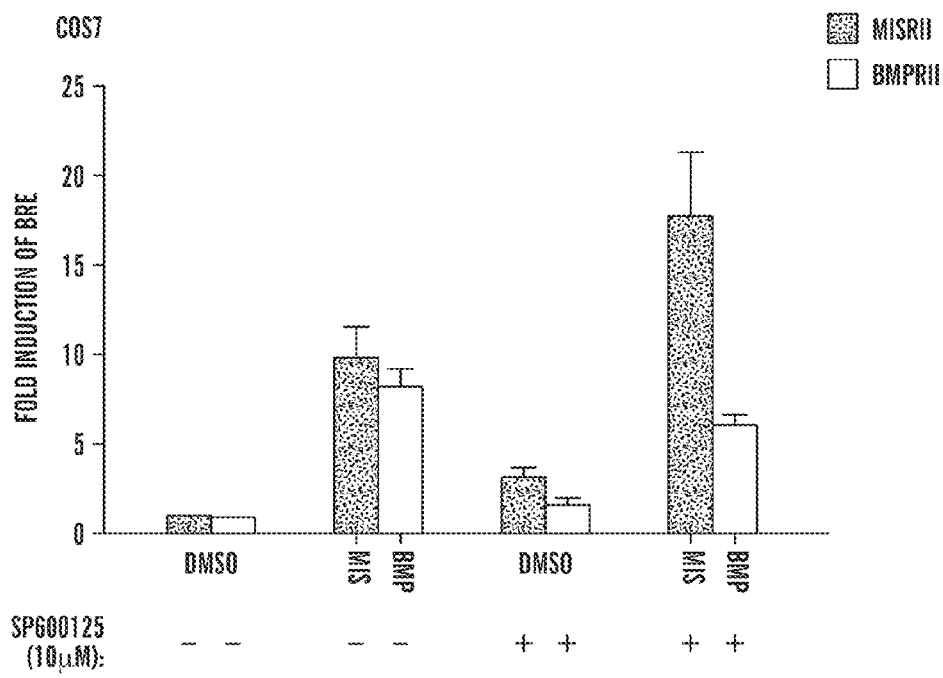

Little is known about the down-stream signaling events that follow MIS binding to its receptor. Reporters that have been used to study MIS effects include the BMP-specific reporter genes XVent2 and Tlx (Clarke, 2001b). In this study the inventors used a BMP-responsive (BRE) promoter to drive expression of firefly luciferase. This reporter is also activated by BMPs, but not by TGFβ or activin (Korchynskyi and ten Dijke, 2002). To investigate the receptor-specificity of SP600125 and exclude the possibility that this molecule activates other signaling pathways common for the TGFβ family, the inventors transfected COS7 cells with a BMP type II receptor (BMPRII) expression construct and the BRE-luciferase reporter. As expected, 25 ng/ml BMP2, a ligand for BMPRII, induced BRE-luciferase activity in cells transfected with BMPRII. However, in contrast to the synergistic induction observed with the MISRII-transfected cells treated with MIS and SP600125, cotreatment of BMPRII-transfected cells with BMP2 and 10 μM SP600125 decreased luciferase activity by 25% compared to BMP2 alone (FIG. 2D). In addition, the inventors tested whether the type II receptors for TGFβ and activin responded to SP600125 by co-transfecting the corresponding receptor with a CAGA-promoter driven luciferase reporter into COS7 cells. This reporter construct has been shown to be activated by both activin and TGFβ via the smad3 pathway (Dennler, 1998). However, SP600125 did not have any significant effect alone or in combination with the receptor-ligand (data not shown).

Example 2

Synergy with SP600125 and MIS

In the next set of experiments, the inventors assessed whether addition of MIS and SP600125 resulted in an additive or cooperated to provide a synergistic effect on BRE-luciferase activity. COS7 cells were cotransfected with the luciferase reporters and the MISRII expression construct, treated with a combination of MIS and SP600125 and compared to cells treated with MIS alone. In FIG. 2A, the inventor discovered that MIS added at a final concentration of 0.5 ug/ml induced luciferase expression greater than ten-fold. Addition of as little as 5 uM SP600125 increased the MIS-mediated induction by approximately 16-fold, equivalent to an additional six-fold over MIS alone. Increasing the concentration of SP600125 to 10 uM and 25 uM resulted in inductions of 22- and 25-fold, respectively. Statistical analyses by two-way ANOVA showed a synergistic effect on the activation of BRE-luciferase when MIS and SP600125 were combined compared with either alone. Addition of a different small molecule inhibitor of JNK, JNK inhibitor VIII, did not result in any activation of BRE-luciferase at 5, 25 or 50 µM concentration and no further effect was seen when combined with MIS (FIG. 2B). Additionally, a peptide inhibitor, JNK inhibitor III, did not result in any activation of BRE-luciferase at 1 or 5 µM concentration and no further effect was seen when combined with MIS (data not shown). The synergy of SP600125 and MIS was also tested in a time course experiment. In FIG. 2C, the inventors discovered that 10 uM SP600125 and 0.5 ug/ml MIS maintain their synergistic effect on luciferase activity after 6 h through 48 h cotreatment over that of each treatment alone.

Figure 2E:
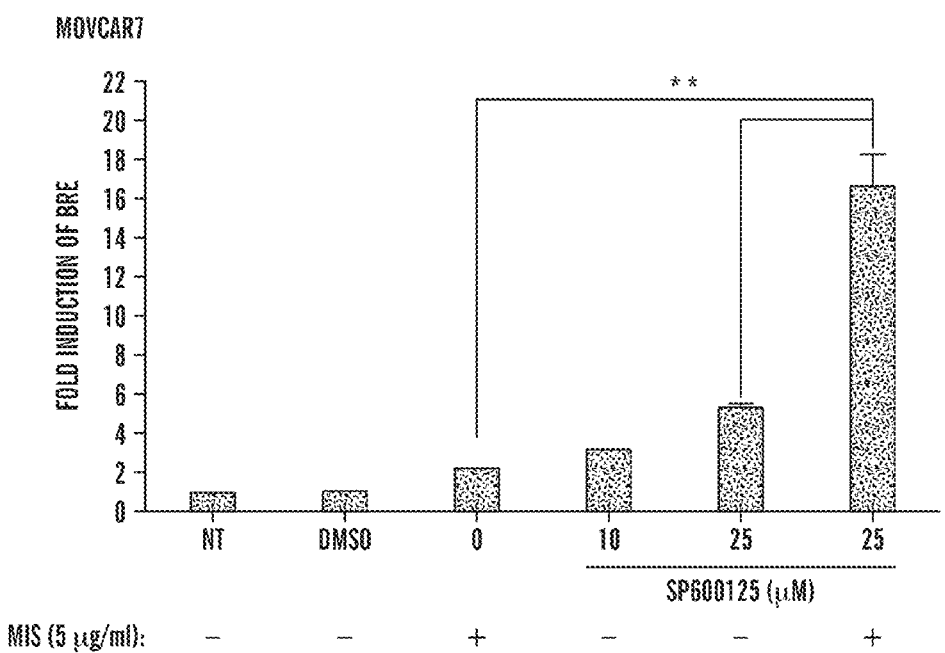

In order to rule out the possibility that BRE-Luciferase induction by SP600125 might be an artifact of MISRII overexpression in COS7 cells, the inventors transfected the luciferase reporter constructs into a mouse ovarian cancer cell line, MOVCAR7, that expresses endogenous MISRII (Pieretti-Vanmarcke, 2006b), and assayed for their response to MIS and SP600125. Treatment of the cells with 5 µg/ml MIS resulted in a 2-fold increase of BRE activity compared to untreated cells. Treatment with 25 µM SP600125 resulted in a 5-fold increase in BRE-luciferase activity compared to untreated control. The combined treatment with MIS and SP600125 gave a 16-fold increase in the BRE-response, showing a synergistic effect with more than twice the activity of each treatment alone, which was similar to that observed in COS7 cells (FIG. 2E).

Example 3

MIS does not Activate the JNK Pathway

Figure 3A:
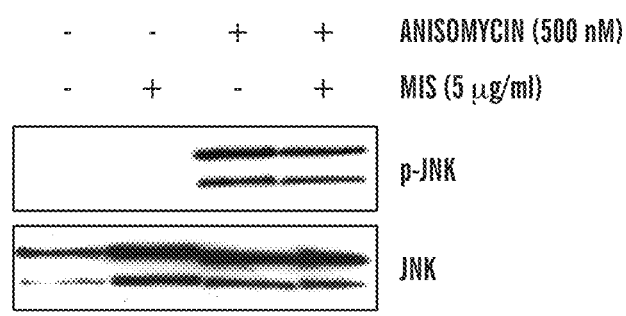
FIG. 3A-3B shows MIS does not activate the JNK-pathway.
Figure 3B:
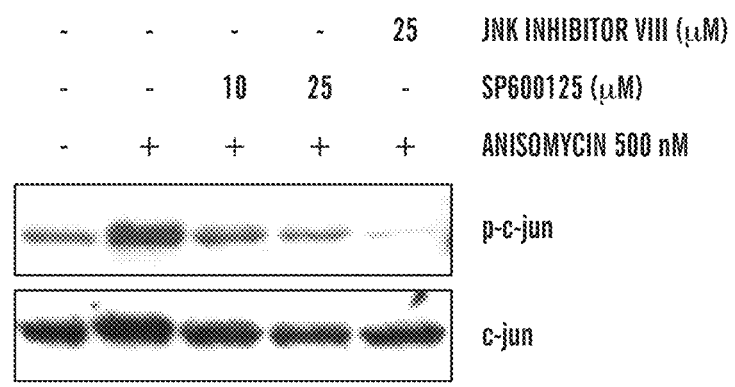

In order to test the possibility that the effects observed with SP600125 are the result of an indirect effect of MISRII-mediated activation of the JNK-pathway the inventors treated MOVCAR7 cells with 5 µg/ml MIS and measured phosphorylation of JNK by immunoblotting (FIG. 3A). The known Jun kinase activator anisomycin was used as a positive control (Hazzalin, 1998). However, no phosphorylation beyond background was observed after 30 min MIS treatment, although a strong activation was achieved with 500 nM anisomycin. Further, MIS had no effect on phosphorylation of JNK by anisomycin. To examine the effects of SP600125 on phosphorylation of c-jun, a downstream target for phosphorylation by JNK, the inventors pre-treated MOVCAR cells with SP600125 before treatment with anisomycin and assessed phospho-c-jun by western blot analysis (FIG. 3B). While the inventors observed inhibition of c-jun phosphorylation with 25 uM SP600125, at 10 uM SP600125, twice the concentration at which synergy with MIS and paclitaxel occurred (see below), the inventors did observe marginal and inconsistent inhibition of c-jun phosphorylation and therefore the inventors have discovered that the effects observed are not due to SP600125-mediated inhibition of the JNK signaling pathway.

Example 4

SP600125 Inhibits Proliferation of an Ovarian Cancer Cell Lines

Figure 4B:
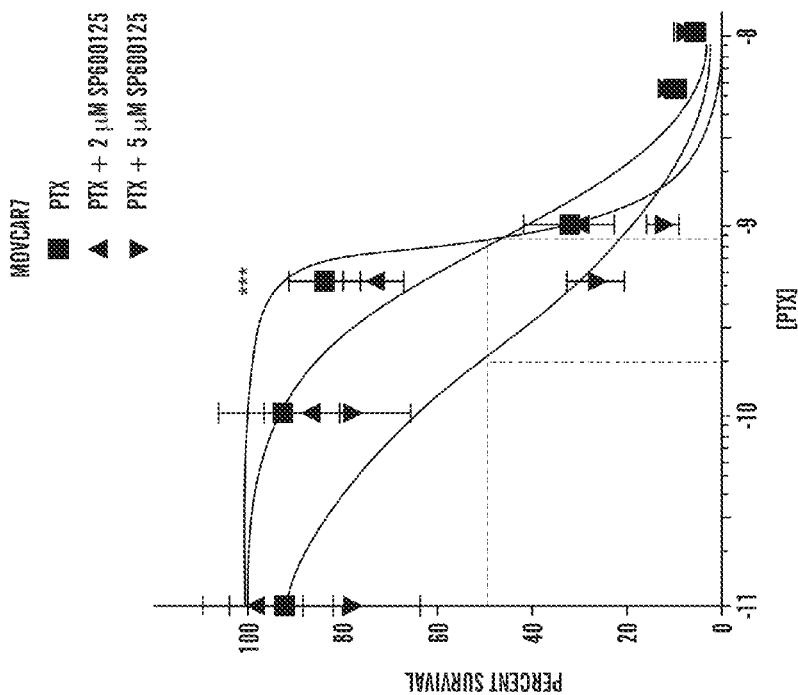
FIG. 4A-4C shows SP600125 inhibits proliferation of MOVCAR7 cells and increases the efficiency of paclitaxel-mediated inhibition of proliferation as detected in an MTT-assay. Cells were plated in 96-well plates and treated the day after. Seven days after plating the cell survival was measured using 3-(4,5-dimethylthiazol-2-yl)-2,5-diphenyltetrazolium bromide substrate and measuring the absorbance at 550 nm.
Figure 4A:
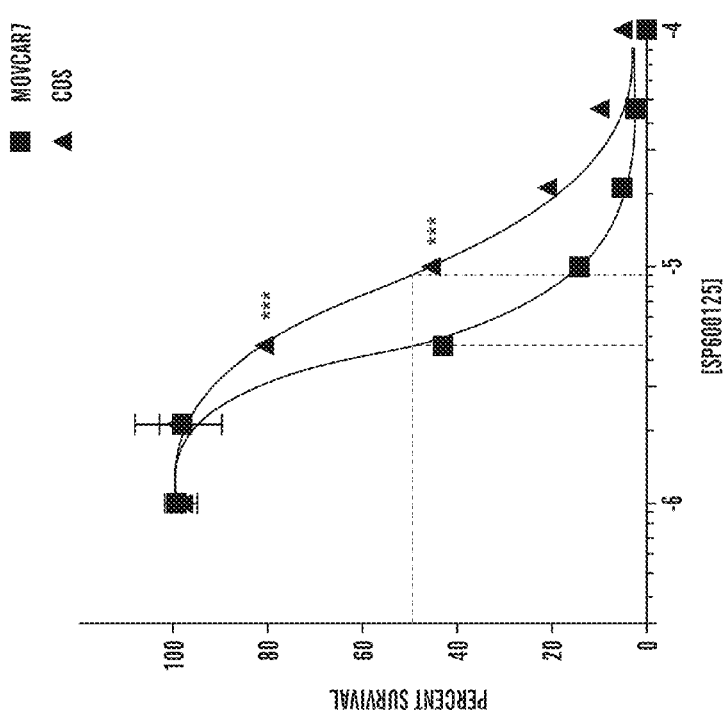

MIS inhibits both the proliferation of MOVCAR7 cells in vitro in proliferation assays and tumor growth in vivo when these cells are xenotransplanted into an immunocompromised mouse model (Pieretti-Vanmarcke, 2006b). Therefore, the inventors tested whether SP600125 had similar effects on MOVCAR7 proliferation in vitro again using the cell proliferation assay. The cells were treated for 7 days and the proliferation was measured by spectrophotometry. To exclude cytotoxic effects on the cells unrelated to MIS signal transduction, we used untransfected COS7 cells as a negative control. The results, as shown in FIG. 4A indicate that SP600125 inhibited cell proliferation in MOVCAR cells in a similar manner to MIS (Pieretti-Vanmarcke, 2006a, Pieretti-Vanmarcke, 2006b) and to a greater extent than in untransfected COS7 cells (IC50 4.5 µM vs. 9.5 µM, respectively). The inventors also investigated whether SP600125 could potentiate the effect of an agent already established in the treatment of ovarian cancer, paclitaxel (FIG. 4B). Paclitaxel is used in treatment of a wide range of tumors, but the side effects can be debilitating (Pieretti-Vanmarcke, 2006a, Pieretti-Vanmarcke, 2006b). The inventors used 2 µM and 5 µM of SP600125 with paclitaxel since these doses inhibited MOVCAR7 cells, but had minimal effect on COS7 cells of only 20% (FIG. 4A). Combining 5 µM of SP600125 with increasing doses of paclitaxel significantly shifted the curve to the left as compared with the paclitaxel alone (IC$_{50}$ 0.21 nM vs. 0.81 nM); demonstrating that adjuvant therapy with SP600125 can be beneficial for patients undergoing treatment with paclitaxel.

Figure 4C:
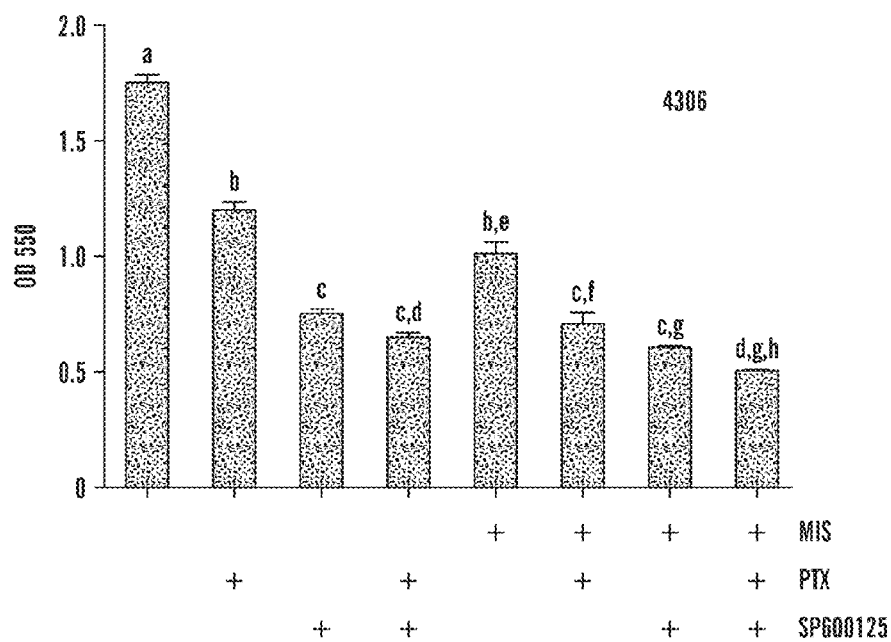

The inventors also tested whether SP600125 could inhibit the proliferation of another mouse ovarian cancer cell line that is inhibited by MIS, 4306 cells (Pieretti-Vanmarcke, 2006a, Pieretti-Vanmarcke, 2006b). In FIG. 4C, the inventors demonstrate that SP600125 at a concentration of 2 µM inhibited proliferation of 4306 cells by 50%. When combined with paclitaxel, SP600125 exerted a synergistically significant inhibition of 4306 proliferation over that of paclitaxel alone. If 2 µM SP600125 is combined with MIS or with MIS and paclitaxel, the levels of cell proliferation is also significantly inhibited and with synergy over MIS alone. These results with another MIS-responsive ovarian cancer cell line demonstrate that SP600125 is also beneficial when MIS-paclitaxel combination therapy becomes available.

Example 5

The growing evidence showing that MIS can act as an inhibitor of tumor cell growth and as a potential drug in the treatment of ovarian cancer lead the inventors to screen for a small molecule that could mimic the receptor-mediated effects of MIS for use either alone or in combination with MIS or other chemotherapeutic agents. From this screening, the inventors discovered SP600125 as a small molecule activator of the MIS type II receptor signaling and a possible candidate for a drug with MIS-like effects. The inventors have discovered that SP600125 activates signaling downstream of the MISRII in a receptor-dependent manner and that it has a synergistic effect on the cellular response to MIS.

With the growing evidence showing that MIS can act as an inhibitor of tumor cell growth and as a potential therapeutic treatment for ovarian cancer, the inventors screened for a small molecule that could mimic the receptor-mediated effects of MIS for use either alone or in combination with MIS or other chemotherapeutic agents. In this screening, the inventors identified SP600125 as a small-molecule activator of the MISRII signaling that had MIS-like effects. As disclosed herein, the inventors have demonstrated that SP600125 activates signaling downstream of the MISRII in a receptor-dependent manner that is dependent on the kinase activity of the MISRII and that it has a synergistic effect on the cellular response to MIS. A role for the JNK pathway in MISRII signaling has not yet been reported, and the inventors did not observe any phosphorylation of JNK by immunoblotting after treatment of cells with MIS.

To exclude the possibility that JNK signaling pathway exerts a negative effect on MISRII signaling, the inventors demonstrated that other inhibitors to JNK, JNK inhibit or VIII, which is also a reversible ATP-competitive inhibitor of JNK(41), and JNK inhibitor III, a jun peptide inhibitor, had no effect on activation of the BRE-luciferase with or without added MIS. Furthermore, JNK inhibitor VIII is much more effective in inhibiting phosphorylation of c-jun than is SP600125, indicating that it would have the same or greater effect on activation of MISRII-mediated signaling if the effect was mainly through inhibition of JNK. The inventors therefore discovered that SP600125 modifies MISRII signal transduction by interacting with the receptor or other molecules necessary for the activation of the receptor.

The inventors also demonstrate herein that SP600125 activates MISRII signaling in a concentration-dependent manner. This effect is specific for the MISRII and was not seen with cells that did not express MISRII or with transfection of other receptors of the TGFβ family. Preliminary studies also demonstrate that canonical Smad1/5/8 phosphorylation is not involved in SP600125-mediated signaling (data not shown).

Based on specificity which was demonstrated in the reporter assay using COS7 cells overexpressing the receptors, the inventors next examined the effect of SP600125 on the proliferation of ovarian cancer cell lines expressing the MISRII. Using MOV-CART cells in the reporter assay demonstrated a similar response pattern and was not an artifact due to MISRII overexpression. The inventors also demonstrated that SP600125 inhibited the proliferation of MOVCAR7 cells to a significantly higher degree than it did in untransfected COS7 cells, demonstrating that endogenous MISRII functions as target for SP600125, and that targeted therapeutics which target MISRII are useful to minimize cytotoxic side effects. The inhibitory effect of SP600125 on ovarian cancer cell proliferation was also observed in 4306 cells, another MIS-responsive cell line (Pieretti-Vanmarcke et al, 2006; Proc Natl Acad Sci USA 103:17426-1743116; Pieretti-Vanmarcke et al, 2006; Clin Cancer Res 12:1593-1598).

As disclosed herein, the inventors demonstrate that the inhibitory effects of SP600125 on ovarian cancer cells is mediated by MISRII signaling, and that SP600125 activates the BRE-luciferase reporter in MISRII-expressing cells (FIG. 2E), an effect that is synergistic with MIS. Additionally, the inventors discovered that MIS and SP600125 together had a greater effect on 4306 proliferation than with MIS alone (FIG. 4C). Taken together, the inventors have discovered that the inhibitory effect of SP600125 on ovarian cancer cell proliferation occurs in a manner similar to that observed with MIS (Pieretti-Vanmarcke et al, 2006; Proc Natl Acad Sci USA 103:17426-1743116; Pieretti-Vanmarcke et al, 2006; Clin Cancer Res 12:1593-1598), and the induced response of the BRE-luciferase reporter in MIS-expressing cells demonstrated that SP600125 is affecting ovarian cancer cell proliferation at least in part by activating MISRII signaling.

As SP600125 has been shown to inhibit the proliferation of human endothelial and prostate tumor cell lines both in vitro by arresting the cells in G2/M phase of the cell cycle and in vivo by inhibiting the growth of injected tumor cells and increasing the efficacy of cyclophosphamide treatment (Ennis et al., 2005; J Pharmacol Exp Ther 313:325-332). Combined with the demonstration of inhibition of MIS-expressing cancer cells as disclosed herein, SP600125 may be beneficial for the treatment of a variety of other cancers as well.

Paclitaxel has been used in the treatment of a wide range of tumors, including ovarian, breast, and prostate. It exerts its effect by targeting the microtubules and arresting the cells in G2/M phase, leading to the induction of apoptosis (Bhalla et al, 2003, Oncogene 22:9075-908645). In contrast to the inventor's discoveries as disclosed herein, previous reports have shown that SP600125 reduced the apoptotic effect of paclitaxel on prostate cancer cells in vitro (Zhang et al., 2006, Int J Cancer 118:2072-208146) and in ovarian cancer cells (Wang et al, 2006; Oncogene 25:4857-486647). Therefore, one would not expect SP600125 to increase the effect of paclitaxel on cancer cells, such as MISRII expressing cancer cells as disclosed herein. Furthermore, the inventors used lower doses of paclitaxel than the previous reports in combination with SP600125 to increase the effect paclitaxel. In fact, the inventors demonstrate that the effect of combination of paclitaxel and SP600125 treatment was optimized at a lower concentration of paclitaxel. Furthermore, the inventors demonstrated that lower concentrations of SP600125, 2-5 μM as compared with the 10-20 μM concentrations did not result in apoptosis. Additionally, paclitaxel is thought to exert a biphasic apoptosis effect through a p53-dependent pathway that induces apoptosis at lower concentrations, whereas at higher concentrations, it inhibits p53 expression in an a sopharyngeal carcinoma cell line (Tan et al., 2002; Int J Cancer 97:168-172). These data demonstrate that a concentration-dependent difference in apoptosis mediated by SP600125 alone or in combination with paclitaxel may be operative in different cells or tissues.

By using different inhibitors to JNK, a c-jun peptide inhibitor or JNK inhibitor III (Calbiochem) and another small molecule inhibitor, JNK inhibitor VIII, the inventors excluded the possibility of JNK exerting a negative effect on MISRII signaling. These inhibitors had no effect on activation of the BRE-luciferase by itself or in combination with MIS, indicating that the inventors have discovered that SP600125 modifies MISRII signal transduction not via interacting with JNK but by interacting with the receptor or other molecules necessary for the activation of the receptor.

Furthermore, the inventors have discovered that SP600125 activates MISRII signaling in a concentration-dependent manner, and also discovered that SP600125 is specific for the MIS type II receptor, and does not activate MISRII signaling in cells not expressing MISRII or with transfection of other receptors of the TGFβ family.

The inventors also discovered that SP600125 inhibited the proliferation of MOVCAR7 and 4307 cells, both ovarian cancer lines expressing MISRII to a significantly higher degree than it did in COST cells, demonstrating that endogenous MISRII is a target for pyrazoloathrones and analogues, for example SP600125.

In addition, the inventors have surprisingly discovered that SP600125 lowers the concentration of paclitaxel needed for an apoptotic effect. Paclitaxel has been used in the treatment of a wide range of tumors, including ovarian, breast, and prostate. It exerts its effect by targeting the microtubules and arresting the cells in G2/M-phase, leading to the induction of apoptosis (Bhalla, 2003). In fact, the inventors have discovered that in combination with SP600125, the optimal concentration of paclitaxal is much lower than the concentration of paclitaxel used alone. This is a surprising discovery and in stark contrast with other findings, where SP600125 was shown to reduce the apoptotic effect of paclitaxel on prostate cancer cells in vitro (Zhang, 2006) and in ovarian cancer cells (Wang, 2006).

In conclusion, the inventor have discovered a small molecule SP600125 that has the same biological activity and functions as MIS, and results in MIS receptor-mediated downstream effects. Accordingly, the inventors have demonstrated that SP600125 can result in inhibition of tumor cell proliferation, and can be used as a therapeutic agent in treatment of MISRII-positive tumors. As disclosed herein, the inventors have discovered that SP600125, a JNK inhibitor, is a small molecule that can mimic the effects of MIS in a receptor-specific manner. The inventors have also discovered that SP600125 can lower the effective concentration of MIS and can be used as a therapeutic for the treatment of ovarian cancer. The inventors have also demonstrated that SP600125 can function in concert to lower the effective therapeutic dose of already established anti-cancer therapeutic agents such as paclitaxel, as well as MIS.

REFERENCES

The references cited herein and throughout the application are incorporated herein in their entirety by reference.

ATFI, A, DJELLOUL, S, CHASTRE, E, DAVIS, R & GESPACH, C (1997) Evidence for a role of Rho-like GTPases and stress-activated protein kinase/c-Jun N-terminal kinase (SAPK/JNK) in transforming growth factor beta-mediated signaling. J Biol Chem, 272, 1429-32.

BAARENDS, W M, VAN HELMOND, M J, POST, M, VAN DER SCHOOT, P J, HOOGERBRUGGE, J W, DE WINTER, J P, UILENBROEK, J T, KARELS, B, WILMING, L G, MEIJERS, J H C & THEMMEN, A P (1994) A novel member of the transmembrane serine/threonine kinase receptor family is specifically expressed in the gonads and in mesenchymal cells adjacent to the mullerian duct. Development, 120, 189-197.

BARBIE, T U, BARBIE, D A, MACLAUGHLIN, D T, MAHESWARAN, S & DONAHOE, P K (2003) Mullerian Inhibiting Substance inhibits cervical cancer cell growth via a pathway involving p130 and p107. Proc Natl Acad Sci USA, 100, 15601-6.

BEHRINGER, R R, FINEGOLD, M J & CATE, R L (1994) Mullerian-inhibiting substance function during mammalian sexual development. Cell, 79, 415-25.

BHALLA, K N (2003) Microtubule-targeted anticancer agents and apoptosis. Oncogene, 22, 9075-86.

CLARKE, T R, HOSHIYA, Y, YI, S E, LIU, X, LYONS, K M & DONAHOE, P K (2001a) Mullerian Inhibiting Substance signaling uses a BMP-like pathway mediated by ALK2 and Induces Smad6 Expression. Mol Endocrinol, 15, 946-959.

CLARKE, T R, HOSHIYA, Y, YI, S E, LIU, X, LYONS, K M & DONAHOE, P K (2001b) Mullerian inhibiting substance signaling uses a bone morphogenetic protein (BMP)-like pathway mediated by ALK2 and induces SMAD6 expression. Mol Endocrinol, 15, 946-59.

CONNOLLY, D C, BAO, R, NIKITIN, A Y, STEPHENS, K C, POOLE, T W, HUA, X, HARRIS, S S, VANDERHYDEN, B C & HAMILTON, T C (2003) Female mice chimeric for expression of the simian virus 40 TAg under control of the MISHR promoter develop epithelial ovarian cancer. Cancer Res, 63, 1389-97.

DENNLER, S, ITOH, S, VIVIEN, D, TEN DIJKE, P, HUET, S & GAUTHIER, J M (1998) Direct binding of Smad3 and Smad4 to critical TGF beta-inducible elements in the promoter of human plasminogen activator inhibitor-type 1 gene. Embo J, 17, 3091-100.

DI CLEMENTE, N, WILSON, C, FAURE, E, BOUSSIN, L, CARMILLO, P, TIZARD, R, PICARD, J Y, VIGIER, B, JOSSO, N & CATE, R (1994) Cloning, expression, and alternative splicing of the receptor for anti-Müllerian hormone. Mol Endocrinol, 8, 1006-1020.

DONAHOE, P K, ITO, Y & HENDREN, W H (1977) A graded organ culture assay for the detection of Mullerian inhibiting substance. J Surg Res, 23, 141-148.

GUPTA, V, CAREY, J L, KAWAKUBO, H, MUZIKANSKY, A, GREEN, J E, DONAHOE, P K, MACLAUGHLIN, D T & MAHESWARAN, S (2005) Mullerian inhibiting substance suppresses tumor growth in the C3(1)T antigen transgenic mouse mammary carcinoma model. Proc Natl Acad Sci USA, 102, 3219-24.

H A, T U, SEGEV, D L, BARBIE, D, MASIAKOS, P T, TRAN, T T, DOMBKOWSKI, D, GLANDER, M, CLARKE, T R, LORENZO, H K, DONAHOE, P K & MAHESWARAN, S (2000) Müllerian inhibiting substance inhibits ovarian cell growth through an Rb-independent mechanism. J Biol Chem, 275, 37101-37109.

HAZZALIN, C A, LE PANSE, R, CANO, E & MAHADEVAN, L C (1998) Anisomycin selectively desensitizes signalling components involved in stress kinase activation and fos and jun induction. Mol Cell Biol, 18, 1844-54.

HE, W W, GUSTAFSON, M L, HIROBE, S & DONAHOE, P K (1993) Developmental expression of four novel serine/threonine kinase receptors homologous to the activin/transforming growth factor-beta type II receptor family. Dev Dyn, 196, 133-142.

HOSHIYA, Y, GUPTA, V, SEGEV, D L, HOSHIYA, M, CAREY, J L, SASUR, L M, TRAN, T T, H A, T U & MAHESWARAN, S (2003) Mullerian Inhibiting Substance induces NFκB signaling in breast and prostate cancer cells. Mol Cell Endocrinol, 211, 43-9.

JAMIN, S P, ARANGO, N A, MISHINA, Y, HANKS, M C & BEHRINGER, R R (2002) Requirement of Bmpr1a for Mullerian duct regression during male sexual development. Nat Genet, 32, 408-10.

KORCHYNSKYI, O & TEN DIJKE, P (2002) Identification and functional characterization of distinct critically important bone morphogenetic protein-specific response elements in the Id1 promoter. J Biol Chem, 277, 4883-91.

LEMONNIER, J, GHAYOR, C, GUICHEUX, J & CAVERZASIO, J (2004) Protein kinase C-independent activation of protein kinase D is involved in BMP-2-induced activation of stress mitogen-activated protein kinases JNK and p38 and osteoblastic cell differentiation. J Biol Chem, 279, 259-64.

LOGEART-AVRAMOGLOU, D, BOURGUIGNON, M, OUDINA, K, TEN DUKE, P & PETITE, H (2006) An assay for the determination of biologically active bone morphogenetic proteins using cells transfected with an inhibitor of differentiation promoter-luciferase construct. Anal Biochem, 349, 78-86.

LORENZO, H K, TEIXEIRA, J, PAHLAVAN, N, LAURICH, V M, DONAHOE, P K & MACLAUGHLIN, D T (2002) New approaches for high-yield purification of Mullerian inhibiting substance improve its bioactivity. J Chromatogr B Analyt Technol Biomed Life Sci, 766, 89-98.

MASSAGUE, J & WOTTON, D (2000) Transcriptional control by the TGF-beta/Smad signaling system. Embo J, 19, 1745-54.

MISHINA, Y, REY, R, FINEGOLD, M J, MATZUK, M M, JOSSO, N, CATE, R L & BEHRINGER, R R (1996) Genetic analysis of the Mullerian-inhibiting substance signal transduction pathway in mammalian sexual differentiation. Genes Dev, 10, 2577-87.

MOSMANN, T (1983) Rapid colorimetric assay for cellular growth and survival: application to proliferation and cytotoxicity assays. J Immunol Methods, 65, 55-63.

PARK, J I, LEE, M G, CHO, K, PARK, B J, CHAE, K S, BYUN, D S, RYU, B K, PARK, Y K & CHI, S G (2003) Transforming growth factor-beta1 activates interleukin-6 expression in prostate cancer cells through the synergistic collaboration of the Smad2, p38-NF-kappaB, JNK, and Ras signaling pathways. Oncogene, 22, 4314-32.

PERLMAN, R, SCHIEMANN, W P, BROOKS, M W, LODISH, H F & WEINBERG, R A (2001) TGF-beta-induced apoptosis is mediated by the adapter protein Daxx that facilitates JNK activation. Nat Cell Biol, 3, 708-14.

PIERETTI-VANMARCKE, R, DONAHOE, P K, PEARSALL, L A, DINULESCU, D M, CONNOLLY, D C, HALPERN, E F, SEIDEN, M V & MACLAUGHLIN, D T (2006a) Mullerian Inhibiting Substance enhances subclinical doses of chemotherapeutic agents to inhibit human and mouse ovarian cancer. Proc Natl Acad Sci USA, 103, 17426-31.

PIERETTI-VANMARCKE, R, DONAHOE, P K, SZOTEK, P, MANGANARO, T, LORENZEN, M K, LORENZEN, J, CONNOLLY, D C, HALPERN, E F & MACLAUGHLIN, DT (2006b) Recombinant human Mullerian inhibiting substance inhibits long-term growth of MIS type II receptor-directed transgenic mouse ovarian cancers in vivo. Clin Cancer Res, 12, 1593-8.

RENAUD, E J, MACLAUGHLIN, D T, OLIVA, E, RUEDA, B R & DONAHOE, P K (2005) Endometrial cancer is a receptor-mediated target for Mullerian Inhibiting Substance. Proc Natl Acad Sci USA, 102, 111-6.

SEGEV, D L, H A, T U, TRAN, T T, KENNEALLY, M, HARKIN, P, JUNG, M, MACLAUGHLIN, D T, DONAHOE, P K & MAHESWARAN, S (2000) Mullerian inhibiting substance inhibits breast cancer cell growth through an NFkappa B-mediated pathway. J Biol Chem, 275, 28371-9.

SOWA, H, KAJI, H, YAMAGUCHI, T, SUGIMOTO, T & CHIHARA, K (2002) Activations of ERK1/2 and INK by transforming growth factor beta negatively regulate Smad3-induced alkaline phosphatase activity and mineralization in mouse osteoblastic cells. J Biol Chem, 277, 36024-31.

STEPHEN, A E, PEARSALL, L A, CHRISTIAN, B P, DONAHOE, P K, VACANTI, J P & MACLAUGHLIN, D T (2002) Highly purified mullerian inhibiting substance inhibits human ovarian cancer in vivo. Clin Cancer Res, 8, 2640-6.

SUZUKI, A, GHAYOR, C, GUICHEUX, J, MAGNE, D, QUILLARD, S, KAKITA, A, ONO, Y, MIURA, Y, OISO, Y, ITOH, M & CAVERZASIO, J (2006) Enhanced expression of the inorganic phosphate transporter Pit-1 is involved in BMP-2-induced matrix mineralization in osteoblast-like cells. J Bone Miner Res, 21, 674-83.

TAKAHASHI, M, HAYASHI, M, MANGANARO, T F & DONAHOE, P K (1986) The ontogeny of mullerian inhibiting substance in granulosa cells of the bovine ovarian follicle. Biol Reprod, 35, 447-53.

TEIXEIRA, J, H E, W W, SHAH, P C, MORIKAWA, N, LEE, M M, CATLIN, E A, HUDSON, P L, WING, J, MACLAUGHLIN, D T & DONAHOE, P K (1996) Developmental expression of a candidate mullerian inhibiting substance type II receptor. Endocrinology, 137, 160-5.

TEIXEIRA, J, MAHESWARAN, S & DONAHOE, P K (2001) Mullerian inhibiting substance: an instructive developmental hormone with diagnostic and possible therapeutic applications. Endocr Rev, 22, 657-74.

TRAN, D, PICARD, J Y, CAMPARGUE, J & JOSSO, N (1987) Immunocytochemical detection of anti-mullerian hormone in Sertoli cells of various mammalian species including human. J Histochem Cytochem, 35, 733-43.

TRAN, T T, SEGEV, D L, GUPTA, V, KAWAKUBO, H, YEO, G, DONAHOE, P K & MAHESWARAN, S (2006) Mullerian Inhibiting Substance Regulates Androgen-Induced Gene Expression and Growth in Prostate Cancer Cells through a Nuclear Factor-{kappa}B-Dependent Smad-Independent Mechanism. Mol Endocrinol, 20, 2382-91.

VISSER, J A, OLASO, R, VERHOEF-POST, M, KRAMER, P, THEMMEN, A P & INGRAHAM, H A (2001) The serine/threonine transmembrane receptor ALK2 mediates Müllerian inhibiting substance signaling. Mol Endocrinol, 15, 936-945.

WANG, P Y, KOISHI, K, MCGEACHIE, A B, KIMBER, M, MACLAUGHLIN, D T, DONAHOE, P K & MCLENNAN, IS (2005) Mullerian inhibiting substance acts as a motor neuron survival factor in vitro. Proc Natl Acad Sci USA, 102, 16421-5.

WANG, T H, CHAN, Y H, CHEN, C W, KUNG, W H, LEE, Y S, WANG, S T, CHANG, T C & WANG, H S (2006) Paclitaxel (Taxol) upregulates expression of functional interleukin-6 in human ovarian cancer cells through multiple signaling pathways. Oncogene, 25, 4857-66.

ZHANG, X, LING, M T, WANG, X & WONG, Y C (2006) Inactivation of Id-1 in prostate cancer cells: A potential therapeutic target in inducing chemosensitization to taxol through activation of JNK pathway. Int J Cancer, 118, 2072-81

SEQUENCES

SEQ ID NO: 1: NT_039207.6 93504644-93506272
SEQ ID NO: 2: NM_000479
  1 gcatgttgac acatcaggcc cagctctatc actggggagg gagataggct gccagggaca 61 gaaagggctc tttgagaagg ccactctgcc tggagtgggg gcgccgggca ctgtccccca -continued

```
 121 aggtcgcggc agaggagata ggggtctgtc ctgcacaaac accccacctt ccactcggct
 181 cacttaaggc aggcagccca gcccctggca gcacccacga tgcgggacct gcctctcacc
 241 agcctggccc tagtgctgtc tgccctgggg gctctgctgg ggactgaggc cctcagagca
 301 gaggagccag ctgtgggcac cagtggcctc atcttccgag aagacttgga ctggcctcca
 361 ggcagcccac aagagcctct gtgcctggtg cactgggcg gggacagcaa tggcagcagc
 421 tcccccctgc gggtggtggg ggctctaagc gcctatgagc aggccttcct ggggccgtg
 481 cagagggccc gctggggccc ccgagacctg gccaccttcg gggtctgcaa caccggtgac
 541 aggcaggctg ccttgccctc tctacggcgg ctggggccct ggctgcggga ccctgggggg
 601 cagcgcctgg tggtcctaca cctggaggaa gtgacctggg agccaacacc ctcgctgagg
 661 ttccaggagc ccccgcctgg aggagctggc ccccagagc tggcgctgct ggtgctgtac
 721 cctgggcctg gccctgaggt cactgtgacg agggctgggc tgccgggtgc ccagagcctc
 781 tgccctcccc gagacacccg ctacctggtg ttagcggtgg accgcctgc gggggcctgg
 841 cgcggctccg ggctggcctt gaccctgcag ccccgcggag aggactcccg gctgagtacc
 901 gcccggctgc aggcactgct gttcggcgac gaccaccgct gcttcacacg gatgaccccg
 961 gccctgctcc tgctgccgcg gtccgagccc gcgccgctgc ctgcgcacgg ccagctggac
1021 accgtgccct tccgccgcc caggccatcc gcggaactcg aggagtcgcc acccagcgca
1081 gaccccttcc tggagacgct cacgcgcctg gtgcgggcgc tgcgggtccc ccggcccgg
1141 gcctccgcgc cgcgcctggc cctggatccg gacgcgctgg ccggcttccc gcagggccta
1201 gtcaacctgt cggaccccgc ggcgctggag cgcctactcg acggcgagga gccgctgctg
1261 ctgctgctga ggcccactgc ggccaccacc ggggatcctg cgcccctgca cgaccccacg
1321 tcggcgccgt gggccacggc cctggcgcgc gcgtggctg ctgaactgca agcggcggct
1381 gccgagctgc gaagcctccc gggtctgcct ccggccacag ccccgctgct ggcgcgcctg
1441 ctcgcgctct gcccaggtgg ccccggcggc ctcggcgatc ccctgcgagc gctgctgctc
1501 ctgaaggcgc tgcagggcct gcgcgtggag tggcgcgggc gggatccgcg cgggccgggt
1561 cgggcacagc gcagcgcggg ggccaccgcc gccgacgggc cgtgcgcgct gcgcgagctc
1621 agcgtagacc tccgcgccga gcgctccgta ctcatccccg agacctacca ggccaacaat
1681 tgccagggcg tgtgcggctg gcctcagtcc gaccgcaacc cgcgctacgg caaccacgtg
1741 gtgctgctgc tgaagatgca ggcccgtggg gccgccctgg cgcgccacc ctgctgcgtg
1801 cccaccgcct acgcgggcaa gctgctcatc agcctgtcgg aggagcgcat cagcgcgcac
1861 cacgtgccca acatggtggc caccgagtgt ggctgccggt gacccctgcg ccgcgcggac
1921 tcctgccccg agggtccgga cgcgcccag ctcgcgcccc ttcccatatt tattcggacc
1981 ccaagcatcg ccccaataaa gaccagcaag caaccggcaa aaaaaaaaa aaaaaaaaa
2041 aaaaaaaaaa aaaaaaaaa aaaaa
```

SEQ ID NO: 3
KO3474

```
   1 cacatcaggc ccagctctat cactgggag ggagataggc tgccagggac agaaagggct
  61 ctttgagaag gccactctgc ctggagtggg ggcgccgggc actgtccccc aaggtcgcgg
 121 cagaggagat aggggtctgt cctgcacaaa caccccacct tccactcggc tcacttaagg
 181 caggcagccc agcccctggc agcacccacg atgcgggacc tgcctctcac cagcctggcc
 241 ctagtgctgt ctgccctggg ggctctgctg gggactgagg ccctcagagc agaggagcca
 301 gctgtgggca ccagtggcct catcttccga gaagacttgg actggcctcc aggcatccca
```

```
 361 caagagcctc tgtgcctggt ggcactgggc ggggacagca atggcagcag ctcccccctg
 421 cgggtggtgg gggctctaag cgcctatgag caggccttcc tgggggccgt gcagagggcc
 481 cgctggggcc cccgagacct ggccaccttc ggggtctgca acaccggtga caggcaggct
 541 gccttgccct ctctacggcg gctgggggcc tggctgcggg accctggggg gcagcgcctg
 601 gtggtcctac acctggagga aggtatgtgg ggcccagccc caagcttggc accgccgtct
 661 tccttcaggt gggccgggtc ctcctaggga agatcagggg ctggcagagc ccccaccctg
 721 ggcagggagg ctgtggtctt gttcctagga ctgggttgcg ggtccgtggc ctggaaggtg
 781 ggcaccacac tctgtcctgt ccccgaagcc cagctcttag acttgcccct gcctcggtgc
 841 cagggagaga gctgctgcct tctccccacc cctgaagacg acgcagggct cggggccagt
 901 ggaacccttc ttcccacagc cccagcctgt tctcagggcc gctggcctaa gatactccct
 961 gcggggaagg ggcttcatcg ggcaccccaa cccagagacc ccagggcggc agccccaccc
1021 acagcctcag acgcagcccc tgcctgcccc tgccgtcacc gctccctggc tgcaggaagg
1081 cagctaagag gggcacccct tgtcccccgct tgaggtcccc tgcacagtgg ccagagcggc
1141 agggacagat cccaaagatt cccggggggt gtggccttca atggctcagg cgtcccctgc
1201 tgtcccggct gcagtgacct gggagccaac accctcgctg aggttccagg agccccgcc
1261 tggaggagct ggccccccag agctggcgct gctggtgctg taccctgggc ctggccctga
1321 ggtcactgtg acgagggctg ggctgccggg tgcccaggta ccaggagtt gcatggggca
1381 gtgcccgggc cgtggcgggg ggcatgaatt tgttgcaggg tctgcagtac tgagaacagc
1441 gtagaaccag tggcgatggg aggaagggga ccggtagagc ggggctgggt aagcctccat
1501 ccagccgggc tgagccctgg tctccgcaga gcctctgccc ctcccgagac accgctacc
1561 tggtgttagc ggtggaccgc cctgcggggg cctggcgcgg ctccgggctg gccttgaccc
1621 tgcagccccg cggagagggt aggtccgcgt ggagagggac ggggagccgg gtcgactgcc
1681 cccgggcccc cagcccctga ccagccgcg tgcccaccca ccgcagactc ccggctgagt
1741 accgcccggc tgcaggcact gctgttcggc gacgaccacc gctgcttcac acggatgacc
1801 ccggccctgc tcctgctgcc gcggtccgag cccgcgccgc tgcctgcgca cggccagctg
1861 gacaccgtgc ccttcccgcc gcccaggtgc gcgcaggcac cgggacacgg ggcaggagcg
1921 ggcggggcg gcgtggcctc gtggccgctc tcaactcctc caattgcggg ttccaggcca
1981 tccgcggaac tcgaggagtc gccacccagc gcagacccct tcctggagac gctcacgcgc
2041 ctggtgcggg cgctgcgggt cccccgggcc cgggcctccg cgccgcgcct ggccctggat
2101 ccggacgcgc tggccggctt cccgcagggc ctagtcaacc tgtcggaccc cgcggcgctg
2161 gagcgcctac tcgacggcga ggagccgctg ctgctgctgc tgaggccac tgcggccacc
2221 accggggatc ctgcgcccct gcacgacccc acgtcggcgc cgtgggccac ggccctggcg
2281 cgccgcgtgg ctgctgaact gcaagcggcg gctgccgagc tgcgaagcct cccgggtctg
2341 cctccggcca cagccccgct gctggcgcgc ctgctcgcgc tctgcccagg aggcccggc
2401 ggcctcggcg atcccctgcg agcgctgctg ctcctgaagg cgctgcaggg cctgcgcgtg
2461 gagtggcgcg ggcgggatcc gcgcgggccg ggtcgggcac agcgcagcgc gggggccacc
2521 gccgccgacg ggccgtgcgc gctgcgcgag ctcagcgtag acctccgcgc cgagcgctcc
2581 gtactcatcc ccgagaccta ccaggccaac aattgccagg gcgtgtgcgg ctggcctcag
2641 tccgaccgca acccgcgcta cggcaaccac gtggtgctgc tgctgaagat gcaggcccgt
2701 ggggccgccc tggcgcgccc accctgctgc gtgcccaccg cctacgcggg caagctgctc
2761 atcagcctgt cggaggaacg catcagcgcg caccacgtgc ccaacatggt ggccaccgag
```

-continued

```
2821 tgtggctgcc ggtgacccct gcgccgcgcg gactcctgcc ccgagggtcc ggacgcgccc 2881 cagctcgcgc cccttcccat atttattcgg accccaagca tcgccccaat aaagaccagc 2941 aagcaaccgg ctggggtgtc cgtgcgtgtt aggggggcccg tgggacctcc cttgccgtct 3001 ctcctcgcgc acggcccggg tccgccctgt agcgctcgct gtctctcccc tgcctgaagc 3061 gccccaccac cgtctttcag gccccggact tggtgccggg
```

SEQ ID NO: 4
NM_020547

```
   1 atctgaagaa agatttggcc aggggcagct gtgctggctt atgctcttct ccttctgctg 61 ctgccatcct ccagcaagat gctagggtct ttggggcttt gggcattact tcccacagct 121 gtggaagcac cccaaacag gcgaacctgt gtgttctttg aggcccctgg agtgcgggga 181 agcacaaaga cactgggaga gctgctagat acaggcacag agctccccag agctatccgc 241 tgcctctaca gccgctgctg ctttgggatc tggaacctga cccaagaccg ggcacaggtg 301 gaaatgcaag gatgccgaga cagtgatgag ccaggctgtg agtccctcca ctgtgaccca 361 agtccccgag cccaccccag ccctggctcc actctcttca cctgctcctg tggcactgac 421 ttctgcaatg ccaattacag ccatctgcct cctccaggga gccctgggac tcctggctcc 481 cagggtcccc aggctgcccc aggtgagtcc atctggatgg cactggtgct gctggggctg 541 ttcctcctcc tcctgctgct gctgggcagc atcatcttgg ccctgctaca gcgaaagaac 601 tacagagtgc gaggtgagcc agtgccagag ccaaggccag actcaggcag ggactggagt 661 gtggagctgc aggagctgcc tgagctgtgt ttctcccagg taatccggga aggaggtcat 721 gcagtggttt gggccgggca gctgcaagga aaactggttg ccatcaaggc cttcccaccg 781 aggtctgtgg ctcagttcca agctgagaga gcattgtacg aacttccagg cctacagcac 841 gaccacattg tccgatttat cactgccagc cggggggggtc ctggccgcct gctctctggg 901 cccctgctgg tactgaaact gcatcccaag ggctccctgt gccactactt gacccagtac 961 accagtgact ggggaagttc cctgcggatg gcactgtccc tggcccaggg cctggcattt 1021 ctccatgagg agcgctggca gaatggccaa tataaaccag gtattgccca ccgagatctg 1081 agcagccaga atgtgctcat cgggaagat ggatcgtgtg ccattggaga cctgggcctt 1141 gccttggtgc tccctggcct cactcagccc cctgcctgga cccctactca accacaaggc 1201 ccagctgcca tcatggaagc tggcacccag aggtacatgg caccagagct cttggacaag 1261 actctggacc tacaggattg gggcatggcc ctccgacgag ctgatattta ctctttggct 1321 ctgctcctgt gggagatact gagccgctgc ccagatttga ggcctgacag cagtccacca 1381 cccttccaac tggcctatga ggcagaactg ggcaatagccc ctacctctga tgagctatgg 1441 gccttggcag tgcaggagag gaggcgtccc tacatcccat ccacctggcg ctgctttgcc 1501 acagaccctg atgggctgag ggagctccta aaagactgtt gggatgcaga cccagaagca 1561 cggctgacag ctgagtgtgt acagcagcgc ctggctgcct tggcccatcc tcaagagagc 1621 caccccttc cagagagctg tccacgtggc tgcccacctc tctgcccaga agactgtact 1681 tcaattcctg cccctaccat cctccccctgt aggcctcagc ggagtgcctg ccacttcagc 1741 gttcagcaag gcccttgttc caggaatcct cagcctgcct gtacccttc tcctgtgtaa 1801 atatgcagtt tatgtgtcat caatgtacat gccaacataa atatggcgat tgtat
```

SEQ ID NO: 5
AF172932

```
   1 ggcacgaggg cagctgtgct ggcttatgct cttctccttc tgctgctgcc atcctccagc 61 aagatgctag ggtctttggg gctttgggca ttacttccca cagctgtgga agcaccccca
```

```
121  aacaggcgaa cctgtgtgtt ctttgaggcc cctggagtgc ggggaagcac aaagacactg 181  ggagagctgc tagatacagg cacagagctc cccagagcta tccgctgcct ctacagccgc 241  tgctgctttg ggatctggaa cctgacccaa gacccgggcac aggtggaaat gcaaggatgc 301  cgagacagtg atgagccagg ctgtgagtcc ctccactgtg acccaagtcc ccgagcccac 361  cccagccctg gctccactct cttcacctgc tcctgtggca ctgacttctg caatgccaat 421  tacagccatc tgcctcctcc agggagccct gggactcctg gctcccaggg tccccaggct 481  gccccaggtg agtccatctg gatggcactg gtgctgctgg ggctgttcct cctcctcctg 541  ctgctgctgg gcagcatcat cttggccctg ctacagcgaa agaactacag agtgcgaggt 601  gagccagtgc cagagccaag gccagactca ggcagggact ggagtgtgga gctgcaggag 661  ctgcctgagc tgtgtttctc ccaggtaatc cgggaaggag gtcatgcagt ggtttgggcc 721  gggcagctgc aaggaaaact ggttgccatc aaggccttcc caccgaggtc tgtggctcag 781  ttccaagctg agagagcatt gtacgaactt ccaggcctac agcacgacca cattgtccga 841  tttatcactg ccagccgggg gggtcctggc cgcctgctct ctgggcccct gctggtactg 901  gaactgcatc ccaagggctc cctgtgccac tacttgaccc agtacaccag tgactgggga 961  agttccctgc ggatggcact gtccctggcc cagggcctgg catttctcca tgaggagcgc 1021 tggcagaatg ccaatataaa accaggtatt gcccaccgag atctgagcag ccagaatgtg 1081 ctcattcggg aagatggatc atgtgccatt ggagacctgg ccttgccttt ggtgctccct 1141 ggcctcactc agccccctgc ctggacccct actcaaccac aaggcccagc tgccatcatg 1201 gaagctggca cccagaggta catggcacca gagctcttgg acaagactct ggacctacag 1261 gattggggca tggccctccg acgagctgat atttactctt tggctctgct cctgtgggag 1321 atactgagcc gctgcccaga tttgaggcct gacagcagtc caccacccctt ccaactggcc 1381 tatgaggcag aactgggcaa taccccctacc tctgatgagc tatgggcctt ggcagtgcag 1441 gagaggaggc gtccctacat cccatccacc tggcgctgct tgccacaga ccctgatggg 1501 ctgagggagc tcctagaaga ctgttgggat gcagacccag aagcacggct gacagctgag 1561 tgtgtacagc agcgcctggc tgccttggcc catcctcaag agagccaccc ctttccagag 1621 agctgtccac gtggctgccc acctctctgc ccagaagact gtacttcaat tcctgcccct 1681 accatcctcc cctgtaggcc tcagcggagt gcctgccact tcagcgttca gcaaggccct 1741 tgttccagga atcctcagcc tgcctgtacc cttctcctg tgtaaatatg cagtttatgt 1801 gtcatcaatg tacatgccaa cataaatatg gcgattgtat agctgt
```

The invention claimed is:

1. A method of decreasing the dose of a chemotherapeutic agent for the treatment of cancer expressing Mullerian Inhibiting Substance Receptor II (MISRII), the method comprising administering to the subject a therapeutically effective amount of a pyrazoloanthrone compound and at least one or a combination of chemotherapeutic agents selected from the group consisting of: paclitaxel, cisplatin, doxorubicin, rapamycin, Mullerian Inhibiting Substance (MIS) or recombinant human MIS (rhMIS), wherein the therapeutically effective dose of the chemotherapeutic agent for an apoptotic effect on a cancer cell expressing MISRII in the presence of the pyrazoloanthrone compound is lower as compared to the therapeutically effective dose of the chemotherapeutic agent for the same apoptotic effect on a cancer cell expressing MISRII in the absence of the pyrazoloanthrone compound.

2. The method of claim 1, wherein the pyrazoloanthrone compound is anthrapyrazol-6(2H)-one or derivative or analogue of anthrapyrazol-6(2H)-one which has the structure of formula (I) and which activates MISRII signaling or interacts with the MISRII receptor, wherein formula (I) is as follows:

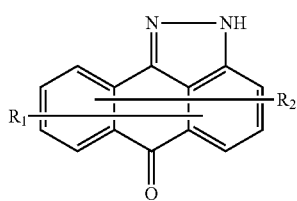

wherein:

R₁ and R₂ are optional substituents that are the same or different and independently represent alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono- or di-alkylaminoalkoxy, or a group represented by formula (a), (b), (c) or (d):

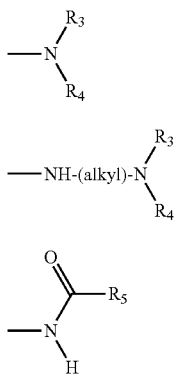

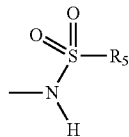

R₃ and R₄ taken together represent alkylidene or a heteroatom-containing alkylidene, or R₃ and R₄ are the same or different and independently represent hydrogen, alkyl, cycloalkyl, aryl, arylalkyl, cycloalkylalkyl, aryloxyalkyl, alkoxyalkyl, alkoxyamino, or alkoxy(mono- or di-alkylamino); and R₅ represents hydrogen, alkyl, cycloalkyl, aryl, arylalkyl, cycloalkylalkyl, alkoxy, amino, mono- or di-alkylamino, arylamino, arylalkylamino, cycloalkylamino, or cycloalkylalkylamino.

3. The method of claim 1, wherein the Mullerian Inhibiting Substance (MIS) or rhMIS is a MIS molecule having at least 95% sequence identity to SEQ ID NO: 2, and has substantially the same biological activity as the MIS protein encoded by SEQ ID NO:2.

4. The method of claim 1, wherein the pyrazoloanthrone compound is administered at the same time, or prior to, or following administration of a chemotherapeutic agent.

5. The method of claim 1, wherein the cancer is ovarian cancer or prostate cancer.

6. The method of claim 1, wherein the pyrazoloanthrone compound is administered in a pharmaceutically acceptable carrier.

7. The method of claim 6, wherein the pharmaceutically acceptable carrier comprises an emulsifying agent.

\* \* \* \* \*